US012622719B2

(12) United States Patent
Inagaki et al.

(10) Patent No.: US 12,622,719 B2
(45) Date of Patent: May 12, 2026

(54) MEDICAL SYSTEM, OPERATION METHOD FOR MEDICAL SYSTEM, AND INFORMATION STORAGE MEDIUM

(71) Applicant: OLYMPUS CORPORATION, Tokyo (JP)

(72) Inventors: Genri Inagaki, Fuchu (JP); Masayasu Chida, Yokohama (JP); Yuji Sakamoto, Kunitachi (JP); Makoto Ishikake, Hachioji (JP); Seiichiro Sakaguchi, Akishima (JP); Shohei Hemmi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 327 days.

(21) Appl. No.: 18/196,089

(22) Filed: May 11, 2023

(65) Prior Publication Data

US 2023/0363777 A1     Nov. 16, 2023

Related U.S. Application Data

(60) Provisional application No. 63/347,656, filed on Jun. 1, 2022, provisional application No. 63/341,515, filed on May 13, 2022.

(51) Int. Cl.
| | |
|---|---|
| *A61B 17/221* | (2006.01) |
| *A61B 17/00* | (2006.01) |
| *A61B 17/22* | (2006.01) |

(52) U.S. Cl.
CPC ...... *A61B 17/221* (2013.01); *A61B 17/00234* (2013.01); *A61B 2017/00022* (2013.01); *A61B 2017/00296* (2013.01); *A61B 2017/22072* (2013.01)

(58) Field of Classification Search
CPC ............ A61B 17/221; A61B 17/00234; A61B 2017/00022; A61B 2017/00296; A61B 2017/22072; A61B 6/481; A61B 18/24; A61B 2090/064; A61B 2017/00818
See application file for complete search history.

(56) References Cited

U.S. PATENT DOCUMENTS

| | | | | |
|---|---|---|---|---|
| 2007/0185377 A1* | 8/2007 | Murakami | ....... | A61B 17/32056 |
| | | | | 600/106 |
| 2015/0366571 A1* | 12/2015 | Navve | ..................... | A61B 5/201 |
| | | | | 606/128 |
| 2022/0096108 A1* | 3/2022 | Baker | .............. | A61B 17/22012 |

* cited by examiner

*Primary Examiner* — Kathleen S Holwerda
*Assistant Examiner* — James R McGinnity
(74) *Attorney, Agent, or Firm* — Scully, Scott, Murphy & Presser, P.C.

(57) ABSTRACT

The medical system includes a basket treatment tool a processor. The processor determines, one or more of: a first determination, based on a transmissive image including the biliary duct, of whether a size of a gallstone allows the basket treatment tool to remove the gallstone from the papillary orifice, or a second determination, based on a resistance when the basket treatment tool is pulled, of whether the resistance allows the basket treatment tool to remove the gallstone from the papillary orifice; and controls the basket treatment tool to remove the gallstone from the papillary orifice when one or more of the first determination or the second determination determines that the gallstone is removable from the papillary orifice.

18 Claims, 40 Drawing Sheets

Figure 21:
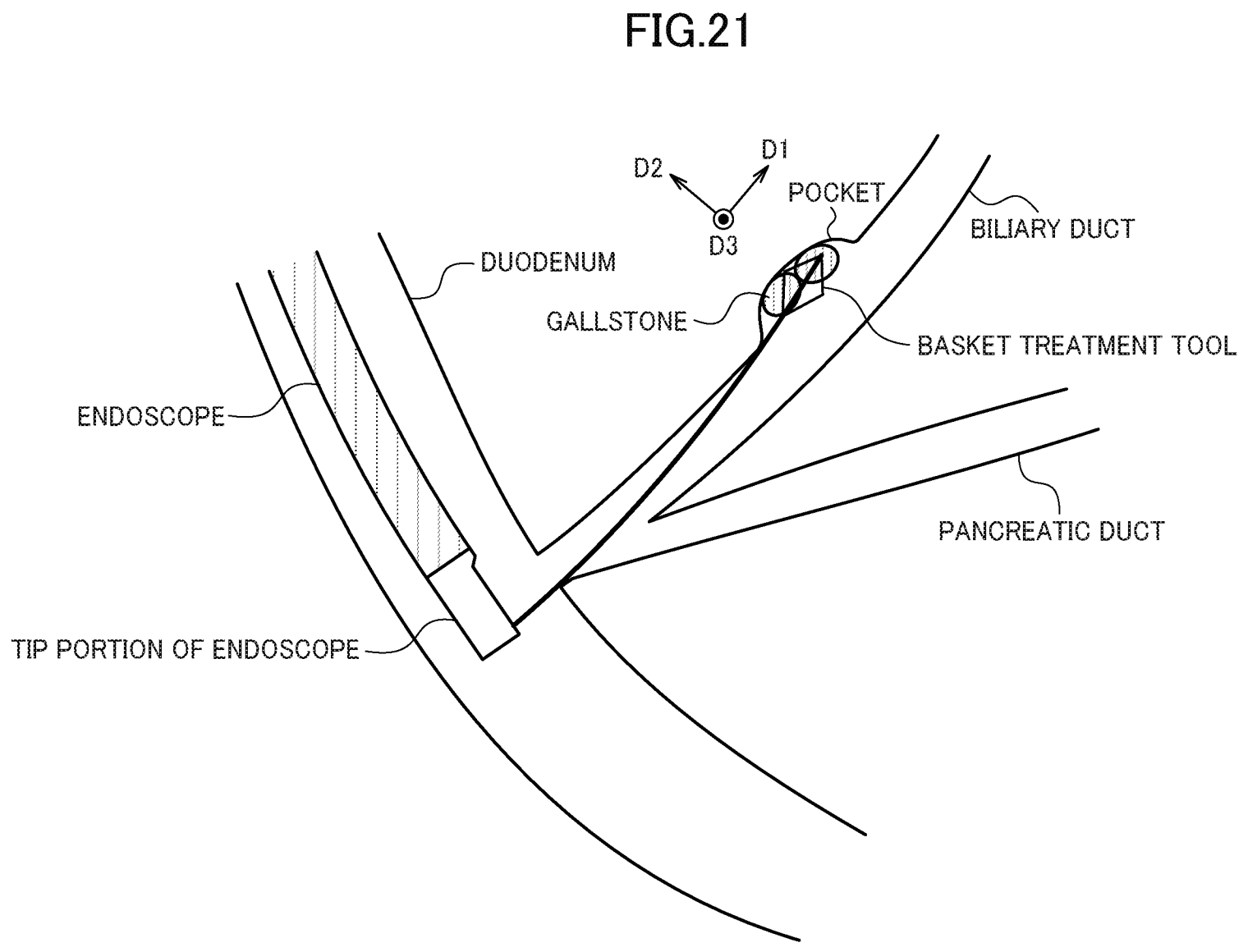

BILIARY DUCT

BASKET TREATMENT TOOL

PANCREATIC DUCT

POCKET

D1

D3

D2

DUODENUM

GALLSTONE

ENDOSCOPE

TIP PORTION OF ENDOSCOPE

Figure 27:
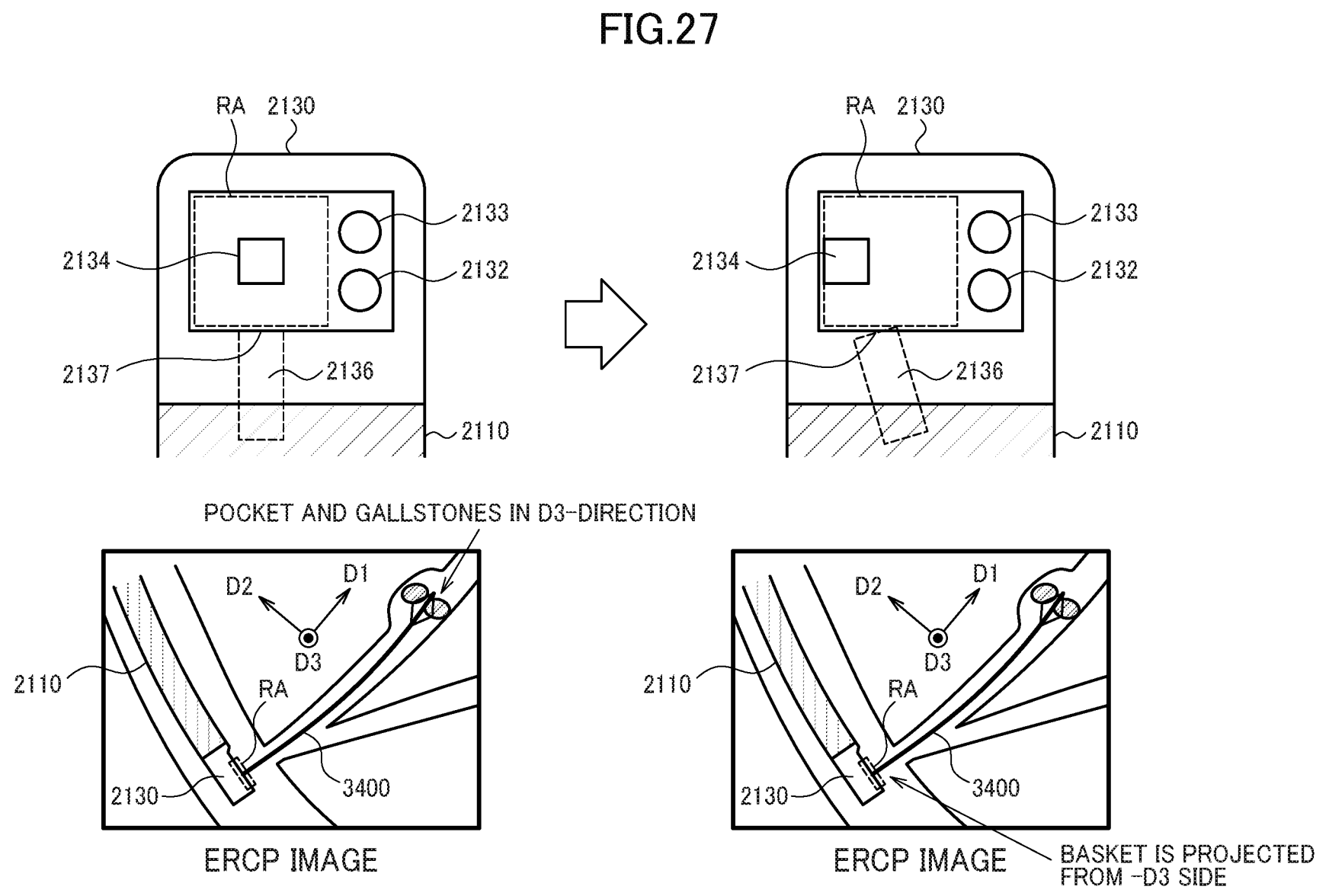

POCKET AND GALLSTONES IN D3-DIRECTION

D1
D3
D2
RA
3400
2130
2110
ERCP IMAGE

BASKET IS PROJECTED FROM −D3 SIDE

D1
D3
D2
RA
3400
2130
2110
ERCP IMAGE

MEDICAL SYSTEM, OPERATION METHOD FOR MEDICAL SYSTEM, AND INFORMATION STORAGE MEDIUM

RELATED APPLICATION DATA

This application is based on and claims priority under 37 U.S.C. § 119 to U.S. Provisional Application No. 63/341, 515 filed on May 13, 2022, and U.S. Provisional Application No. 63/347,656 filed on Jun. 1, 2022, the entire contents of each of which are incorporated herein by reference.

BACKGROUND

Known is a medical system that remotely performs electric control of a main body of an endoscope inserted into a body cavity and various types of treatment tools each inserted through a forceps channel. The specification of United States Patent Application Publication No. 2007/0185377 discloses a method of advancing/retreating and opening/closing a basket forceps in accordance with an embedded program.

SUMMARY

In accordance with one of some aspect, there is provided a medical system comprising:
    a basket treatment tool configured to be inserted into a biliary duct from a papillary orifice and configured to be driven to for open/close and advance/retreat; and
    a processor comprising hardware, the processor being configured to:
        determine, one or more of:
            a first determination, based on a transmissive image including the biliary duct, of whether a size of a gallstone allows the basket treatment tool to remove the gallstone from the papillary orifice, or
            a second determination, based on a resistance when the basket treatment tool is pulled, of whether the resistance allows the basket treatment tool to remove the gallstone from the papillary orifice; and
        control the basket treatment tool to remove the gallstone from the papillary orifice when one or more of the first determination or the second determination determines that the gallstone is removable from the papillary orifice.
In accordance with one of some aspect, there is provided an operation method for a medical system, the operation method comprising:
    determining one or more of:
        a first determination, based on a transmissive image including the biliary duct, of whether a size of a gallstone allows the basket treatment tool to remove the gallstone from the papillary orifice, or
        a second determination, based on a resistance when the basket treatment tool is pulled, of whether the resistance allows the basket treatment tool to remove the gallstone from the papillary orifice; and
    control a basket treatment tool configured to be inserted into a biliary duct from a papillary orifice and configured to be driven to open/close and advance/retreat to remove the gallstone from the papillary orifice using the basket treatment tool when one or more of the first determination or the second determination determines that the gallstone is removable from the papillary orifice.

In accordance with one of some aspect, there is provided a control apparatus comprising:
    a processor configured to:
        determine one or more of:
            a first determination, based on a transmissive image including the biliary duct, of whether a size of a gallstone allows the basket treatment tool to remove the gallstone from the papillary orifice, or
            a second determination, based on a resistance when the basket treatment tool is pulled, of whether the resistance allows the basket treatment tool to remove the gallstone from the papillary orifice; and
        control a basket treatment tool configured to be inserted into a biliary duct from a papillary orifice and configured to be driven to open/close and advance/retreat to remove the gallstone from the papillary orifice using the basket treatment tool when one or more of the first determination or the second determination determines that the gallstone is removable from the papillary orifice.

BRIEF DESCRIPTION OF THE DRAWINGS

FIG. 20 is a diagram illustrating a pocket case of a gallstone.

FIG. 21 is a diagram illustrating a method of removing a gallstone in a pocket.

FIG. 23 is a diagram for describing step S2.

FIG. 25 is a diagram for determining the projection position.

FIG. 26 illustrates a first example of automatic control.

FIG. 27 illustrates a second example of automatic control.

FIG. 35 is a diagram for describing extraction of a stone using the basket treatment tool.

FIG. 39 is a diagram for describing an issue in the manipulation of removing the kidney stone.

DESCRIPTION OF EXEMPLARY EMBODIMENTS

Figure 1:
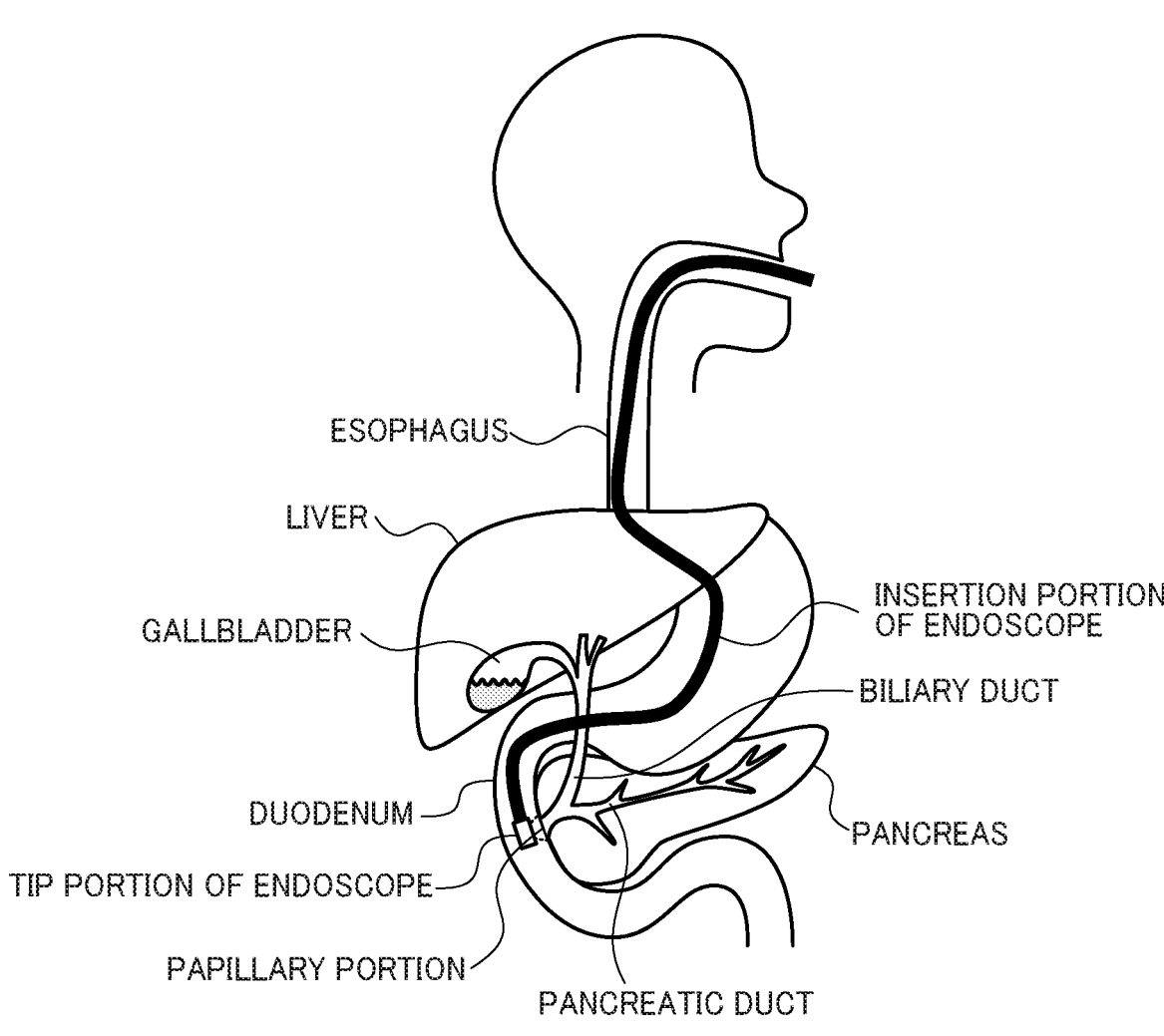
FIG. 1 is a diagram illustrating organs and tissues that are related to manipulation of endoscopic retrograde cholangiopancreatography (ERCP).

The following disclosure provides many different embodiments, or examples, for implementing different features of the provided subject matter. These are, of course, merely examples and are not intended to be limiting. In addition, the disclosure may repeat reference numerals and/or letters in the various examples. This repetition is for the purpose of simplicity and clarity and does not in itself dictate a relationship between the various embodiments and/or configurations discussed. Further, when a first element is described as being "connected" or "coupled" to a second element, such description includes embodiments in which the first and second elements are directly connected or coupled to each other, and also includes embodiments in which the first and second elements are indirectly connected or coupled to each other with one or more other intervening elements in between.

The present embodiment relates to automatic control performed when treatment in accordance with endoscopic retrograde cholangiopancreatography (ERCP) and a content of medical treatment is performed with use of an electrically driven medical system. The ERCP is an abbreviation for endoscopic retrograde cholangiopancreatography.

First, a content of manipulation of the ERCP is described. FIG. 1 illustrates organs and tissues that are related to the manipulation of the ERCP. Note that an organ has a unique structure in which a plurality of types of tissues gathers together, and has a specific function. In FIG. 1, the liver, the gallbladder, the pancreas, the esophagus, the stomach, and the duodenum correspond to the organs. The tissues are formed by related cells being coupled to each other, such as blood vessels, muscles, and skin. In FIG. 1, the biliary duct and the pancreatic duct correspond to the tissues.

The object of the treatment by the ERCP is the biliary duct. The biliary duct is a duct line for flowing biliary created by the liver to the duodenum. To approach the biliary duct with an endoscope, a treatment tool that is inserted through a channel of the endoscope is inserted from the papillary portion of the duodenum to the biliary duct while the endoscope remains to be held at a position of the duodenum. The papillary portion of the duodenum is hereinafter simply referred to as the papillary portion. The papillary portion is a region including an orifice in which luminal tissues open to the duodenum, and not only the orifice but also a structure in the periphery of the orifice is referred to as the papillary portion. The orifice of the luminal tissues is a portion, in which a common duct in which the biliary duct and the pancreatic duct join together, opens to the duodenum.

Figure 2:
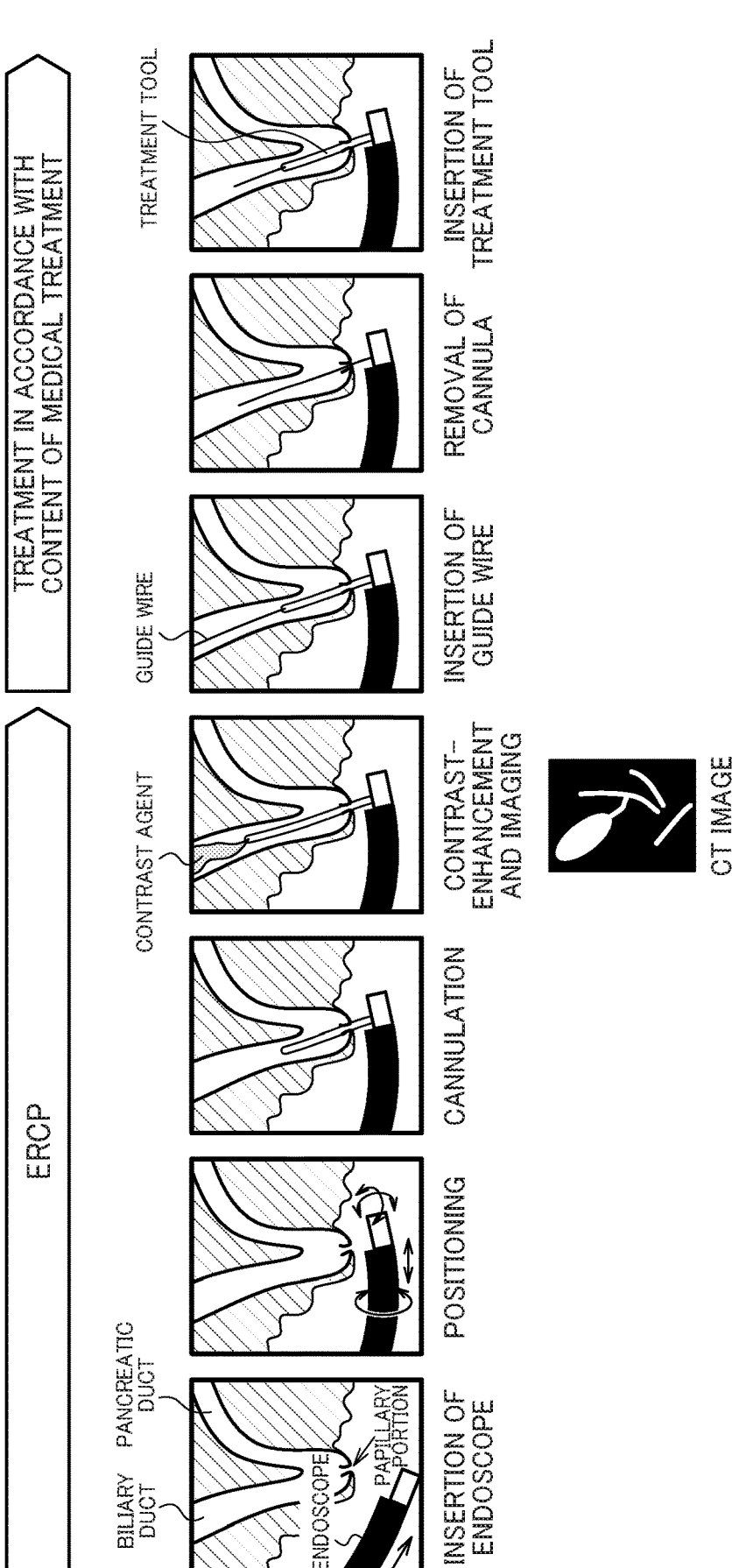
FIG. 2 illustrates the flow of manipulation of the ERCP.

FIG. 2 illustrates the flow of treatment in accordance with the ERCP and a content of medical treatment. A side-view-type endoscope provided with a camera, a illumination lens, and an opening of a treatment tool channel on a side surface of the tip portion of the endoscope is used for the ERCP. Note that the camera is also referred to as an imaging device or imaging sensor.

In an endoscope insertion step, an insertion portion of the endoscope is inserted from the mouth, by way of the esophagus and the stomach, into the duodenum. At this time, the insertion portion is inserted to a position where the papillary portion is roughly seen in a visual field of the endoscope. Subsequently, in a positioning step, the endoscope is aligned with the papillary portion. Specifically, the position of the tip portion of the endoscope is adjusted so that the papillary portion is within an imaging range of the camera of the endoscope. Alternatively, the position of the tip portion of the endoscope is adjusted so that the camera of the endoscope is at a correct position with respect to the papillary portion and is seen at the center of the field view.

Subsequently, in a cannulation step, a cannula is inserted from the papillary portion to the biliary duct. Specifically, the cannula is inserted into the treatment tool channel of the endoscope to project the cannula from a channel opening in the tip portion of the endoscope, a tip of the cannula is put in an orifice of the common duct and inserted into the common duct, and furthermore, the cannula is inserted from a joint portion of the biliary duct and the pancreatic duct toward a direction of the biliary duct. Note that the cannulation is insertion of the cannula into the body. The cannula is a medical tube that is inserted into the body and used for a medical purpose.

Subsequently, in a contrast-enhancement and imaging step, a contrast agent is injected into the cannula and is poured from the tip of the cannula into the biliary duct. X-ray imaging or computed tomography (CT) imaging is performed in this state, whereby an X-ray image or a CT image, in which the biliary duct, the gallbladder, and the pancreatic duct are seen, is acquired. This is the manipulation of the ERCP, and thereafter various kinds of treatment are performed in accordance with results of diagnosis based on the X-ray image or the CT image. One example of the treatment will be described below.

In a guide wire insertion step, a guide wire is inserted into the cannula to project the guide wire from the tip of the cannula, and the guide wire is inserted into the biliary duct. In a cannula removal step, the cannula is removed while the guide wire is left inside the biliary duct. This leads to a state where only the guide wire projects from the tip of the endoscope and is left inside the biliary duct. Subsequently, in a treatment tool insertion step, the treatment tool is inserted into the biliary duct along the guide wire. The treatment tool is, for example, the basket treatment tool exemplified in the present embodiment, but may be a stent or the like. Note that the stent is a treatment tool that is inserted into a narrowed part of the biliary duct to expand the narrowed part, and is left after insertion to maintain an expanded state of the narrowed part.

Figure 3:
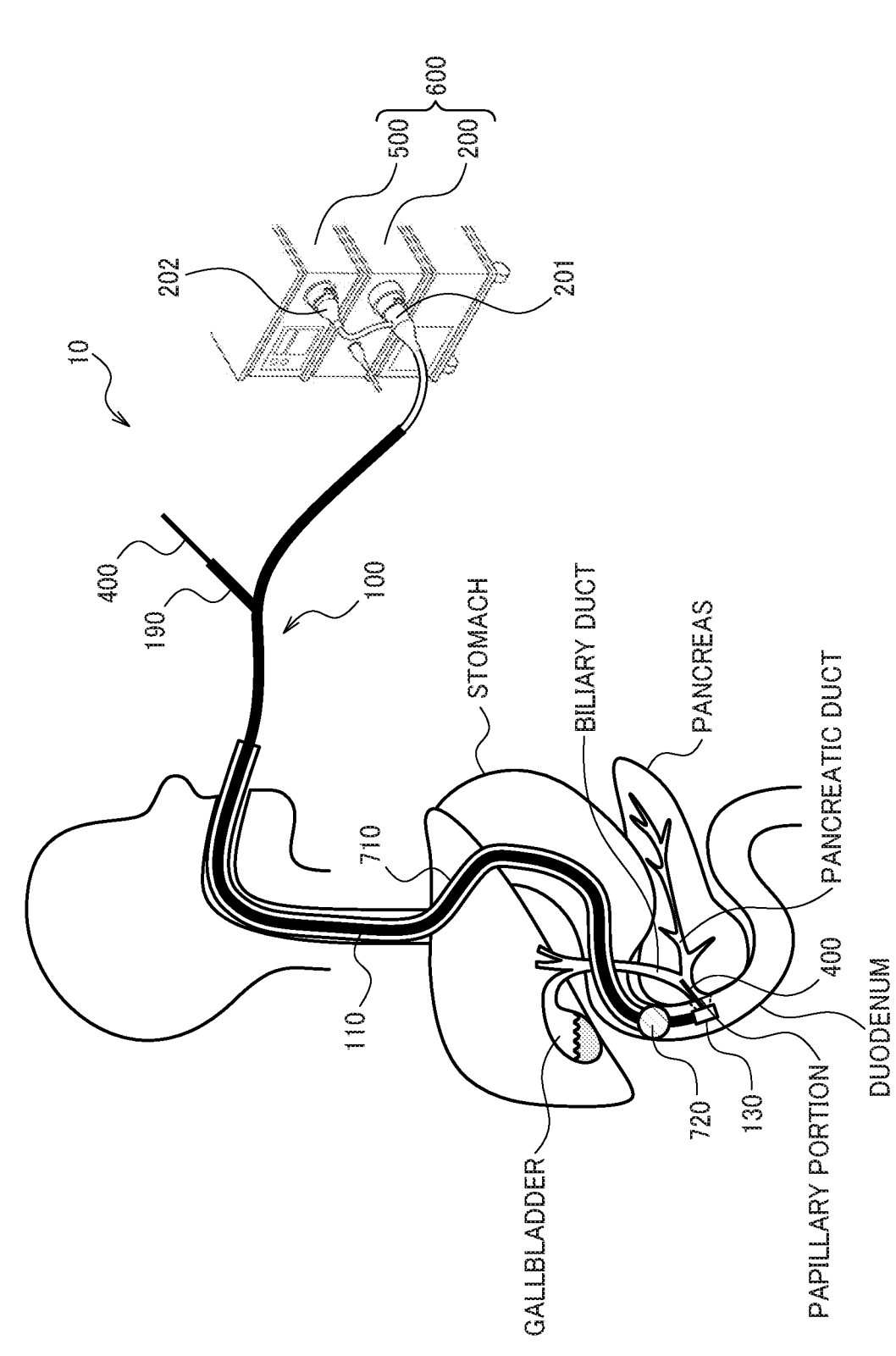
FIG. 3 is a diagram for describing a configuration example of a medical system.

FIG. 3 illustrates a configuration example of a medical system 10 in accordance with the present embodiment. The medical system 10 includes an endoscope 100, a treatment tool 400, and a control device 600. The control device 600 includes a drive control device 200 to which a connector 201 is connected, and a video control device 500 to which a connector 202 is connected. The endoscope 100 is detachably connected to the control device 600 by the connectors 201 and 202.

Note that the medical system 10 is also referred to as an endoscope system. Additionally, in a case where the endoscope 100 is of an electrically driven type, the medical system 10 can be also referred to as an electrically driven endoscope system. While FIG. 3 exemplifies the medical system 10 using the endoscope 100 of the electrically driven type, the medical system 10 may use the endoscope 100 of a manual operation type.

The control device 600 controls each section of the drive control device 200, the video control device 500, and the like, and plays a main role in performing the processing flow that will be described later with reference to FIG. 8 or subsequent drawings. The control device 600 includes the following hardware. The hardware can include at least one of a circuit that processes a digital signal or a circuit that processes an analog signal. For example, the hardware can include one or more circuit devices mounted on a circuit board, or one or more circuit elements. The one or more circuit devices are, for example, integrated circuits (ICs), field-programmable gate array (FPGA) circuits, or the like. The one or more circuit elements are, for example, resistors, capacitors, or the like.

In addition, the control device 600 is implemented by inclusion of at least one of the following processors. The control device 600 includes a memory that stores information, and a processor that operates based on the information stored in the memory. The information is, for example, a program, various kinds of data, and the like. The processor includes hardware. Note that various kinds of processors such as a central processing unit (CPU), a graphics processing unit (GPU), and a digital signal processor (DSP) can be used. The memory may be a semiconductor memory such as a static random-access memory (SRAM) and a dynamic random-access memory (DRAM). The memory may be a register. The memory may be a magnetic storage device such as a hard disk drive (HDD). The memory may be an optical storage device such as an optical disk device. For example, the memory stores a computer-readable instruction. The instruction is executed by the processor, whereby part or all of functions of each section of the control device 600 is implemented as processing. The instruction mentioned herein may be an instruction of an instruction set that is included in a program, or may be an instruction that instructs a hardware circuit included in the processor to operate. Furthermore, all or part of each section of the control device 600 can be implemented by cloud computing, and each processing described later with reference to FIG. 8 or the like can be executed on the cloud computing.

The drive control device 200 controls electric driving of the endoscope 100 through the connector 201. The drive control device 200 can be implemented by including a processor similar to the above-mentioned processor. Although not illustrated in FIG. 3, an operation device for manually operating electric driving may be connected to the drive control device 200.

The video control device 500 receives an image signal from the camera arranged in a tip portion 130 of the endoscope 100 through the connector 202, generates a display image from the image signal, and performs processing of displaying the display image on a display device, which is not illustrated. The video control device 500 can be implemented by including a processor similar to the above-mentioned processor.

Note that the drive control device 200 and the video control device 500 are illustrated as individual devices in FIG. 3, but may be configured as an integrated device. In this case, the connectors 201 and 202 may be integrated as one connector. The following description will be given assuming that the control device 600, the drive control device 200, the video control device 500 each include an individual processor, but the configuration is not limited thereto. For example, a processor or the like of the control device 600 may fulfill a function as the drive control device 200, and a processor or the like of the control device 600 may fulfill a function as the drive control device 200 and the video control device 500.

The endoscope 100 includes an insertion portion 110. The insertion portion 110 is a portion inserted into a lumen of a patient, and is configured to be flexible in a long and thin shape. Note that details of the endoscope 100 including a configuration other than the insertion portion 110 will be described later. An insertion opening 190 of the treatment tool is arranged on the base end side of the insertion portion 110, and the treatment tool channel for passing the treatment tool 400 from the insertion opening 190 to the opening of the tip portion 130 is arranged inside the insertion portion 110. The insertion opening 190 of the treatment tool is also referred to as a forceps opening, but the treatment tool to be used is not limited to a forceps.

Note that a configuration example of the medical system 10 in accordance with the present embodiment is limited to the above-mentioned examples, and the medical system 10 may further include, for example, an overtube 710 and a balloon 720 as illustrated in FIG. 3.

The overtube 710 is a tube that covers the insertion portion 110 of the endoscope 100 and that is variable in hardness. In a state where the endoscope 100 and the overtube 710 are inserted into the body, at least a bending portion of the insertion portion 110 is in an exposed state from a tip of the overtube 710. The bending portion is a portion configured to be bent at an angle in accordance with a bending operation in the vicinity of the tip of the insertion portion 110. In addition, a base end of the overtube 710 is outside the body, and the base end side of the insertion portion 110 is exposed from the base end of the overtube 710.

The balloon 720 is arranged in the vicinity of the outside tip of the overtube 710. For example, an operator performs an operation of inflating the balloon 720 arranged in the vicinity of the tip of the overtube 710 to fix the tip of the overtube 710 to the duodenum with the balloon 720. This can fix the position of the tip of the overtube 710.

The operator then performs, for example, an operation of hardening the overtube 710. With this operation, the insertion portion 110 is held and an insertion path of the insertion portion 110 is thereby fixed. As a result, the insertion path of the insertion portion 110 can be held. Note that a method of hardening the overtube 710 is publicly known and thus a description thereof is omitted.

Figure 4:
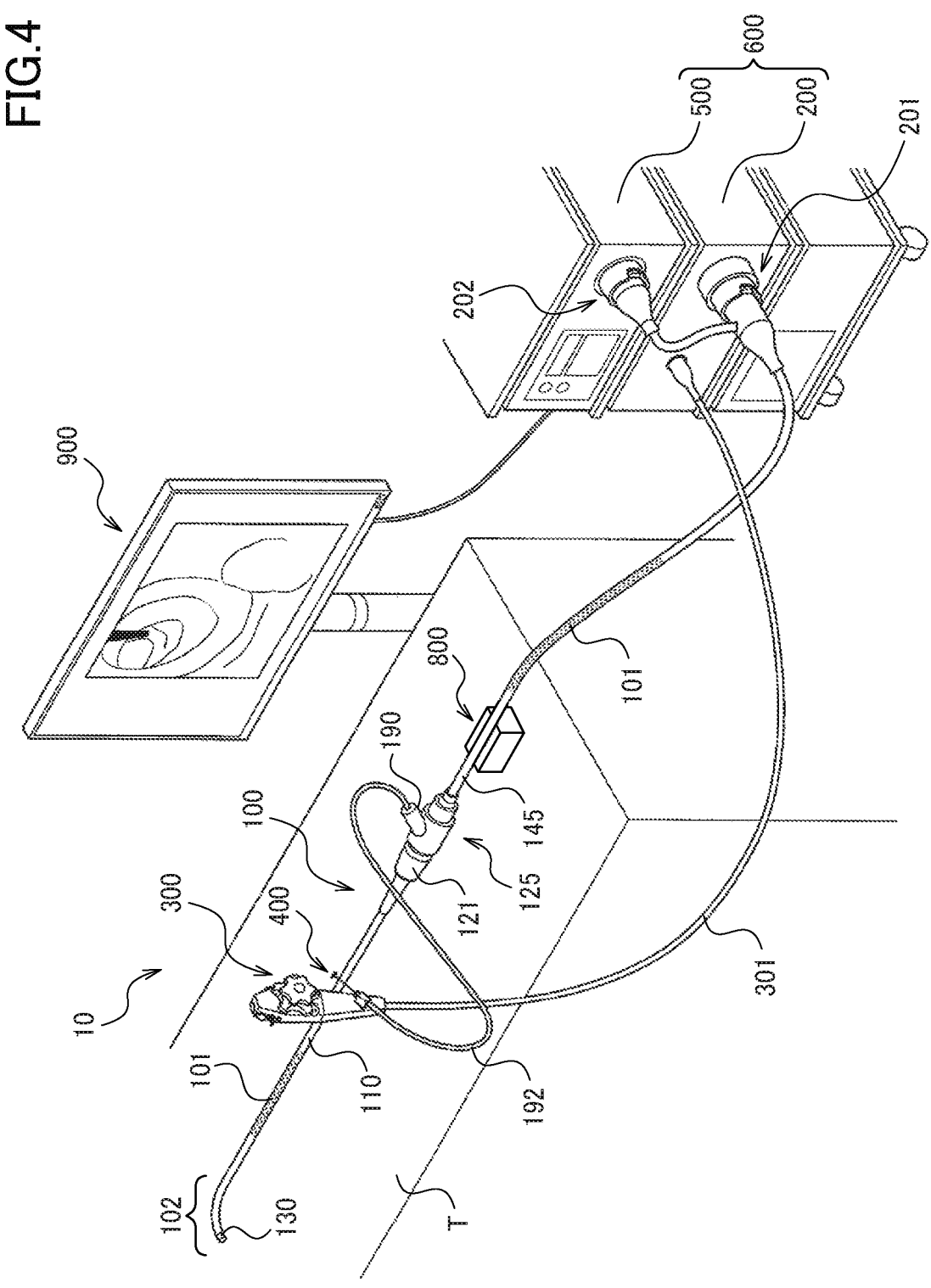
FIG. 4 is a diagram for describing a more detailed configuration example of the medical system.

The medical system 10 in accordance with the present embodiment may be implemented as a configuration example of observing or performing treatment on the inside of the body of the patient lying on an operating table T, as illustrated in FIG. 4. The medical system 10 in FIG. 4 includes the endoscope 100, the control device 600, an operation device 300, the treatment tool 400, an advancing/retreating driving device 800, and a display device 900.

The endoscope 100 is a device that is inserted into the lumen of the patient for observation of a diseased part. In the present embodiment, an insertion side of the endoscope 100 into the lumen of the patient is referred to as a "tip side", and a mounting side of the endoscope 100 to the control device 600 is referred to as a "base end side". The tip end side of the treatment tool 400 in the lumen may be referred to as an "upstream side", and the base end side of the treatment tool 400 may be referred to as a "downstream side. In addition, movement of the treatment tool 400 or the like toward the upstream side may be referred to as "advancing", movement of the treatment tool 400 or the like toward the downstream side may be referred to as "retreating", and advancing and retreating may be simply referred to as "advancing/retreating".

The endoscope 100 includes the insertion portion 110 described above with reference to FIG. 3, a coupling element 125, an extracorporeal flexible portion 145, and the connectors 201 and 202. The insertion portion 110, the coupling element 125, the extracorporeal flexible portion 145, and the connectors 201 and 202 are connected to one another in this order from the tip side.

The insertion portion 110 includes a bending portion 102, an extracorporeal flexible portion that connects a base end of the bending portion 102 and the coupling element 125 to each other, and the tip portion 130 arranged at the tip of the bending portion 102. An internal path 101 is arranged inside the insertion portion 110, the coupling element 125, and the extracorporeal flexible portion 145, and a bending wire that passes through the internal path 101 is connected to the bending portion 102. The drive control device 200 drives the wire through the connector 201 to perform a bending operation of the bending portion 102. A wire for the raising base to be connected to the raising base arranged in the tip portion 130 passes through the internal path 101 and is connected to the connector 201. The drive control device 200 drives the wire for the raising base to change a rising angle of the treatment tool 400 that projects from the side surface of the tip portion 130. The camera, the illumination lens, and the opening of the treatment tool channel are arranged on the side surface of the tip portion 130. An image signal line that connects the camera and the connector 202 to each other is arranged on the internal path 101, and an image signal is transmitted from the camera to the video control device 500 through the image signal line. The video control device 500 displays an endoscope image generated from the image signal on the display device 900.

The insertion opening 190 of the treatment tool and a roll operating portion 121 are arranged in the coupling element 125. The treatment tool channel is arranged on the internal path 101, one end of the treatment tool channel opens in the tip portion 130, and the other end thereof opens in the insertion opening 190 of the treatment tool. An extension tube 192 that extends from the insertion opening 190 to the operation device 300 is connected to the insertion opening 190. The treatment tool 400 is inserted from an opening of the extension tube 192 on the operation device 300 side, passes through the insertion opening 190 and the treatment tool channel, and projects from the opening of the tip portion 130. Note that the extension tube 192 may be omitted and the treatment tool 400 may be inserted from the insertion opening 190. The roll operating portion 121 is attached to the coupling element 125 to be rotatable about an axis line direction of the insertion portion 110. A rotating operation of the roll operating portion 121 rolls the insertion portion 110. Note that the roll operating portion 121 may be driven by a manual operation, or may be capable of being electrically driven.

The advancing/retreating driving device 800 is a driving device that electrically drives the insertion portion 110 to advance/retreat the insertion portion 110. For example, the extracorporeal flexible portion 145 is detachable from the advancing/retreating driving device 800, and the advancing/retreating driving device 800 slides the extracorporeal flexible portion 145 in the axis line direction in a state where the extracorporeal flexible portion 145 is mounted on the advancing/retreating driving device 800, whereby the insertion portion 110 advances/retreats. While FIG. 4 illustrates an example in which the extracorporeal flexible portion 145 and the advancing/retreating driving device 800 are detachable, the configuration is not limited thereto, and the coupling element 125 and the advancing/retreating driving device 800 may be configured to be detachable.

The operation device 300 is detachably connected to the drive control device 200 through an operation cable 301. The operation device 300 may perform wireless communication with the drive control device 200 instead of wired communication. When the operator operates the operation device 300, a signal of the operation input is transmitted to the drive control device 200 through the operation cable 301, and the drive control device 200 electrically drives the endoscope 100 so as to perform an endoscope operation in accordance with the operation input based on the signal of the operation input. The operation device 300 includes five or more channels of operation input sections corresponding to advancing/retreating of the endoscope 100, a bending operation in two directions, rolling, and an operation of the raising base. Note that in a case where there is a non-electrically driven operation among these operations, an operation input section for the operation may be omitted. Each operation input section includes, for example, a dial, a joy stick, an arrow key, a button, and a switch, a touch panel, and/or the like.

The drive control device 200 drives a built-in motor based on an operation input to the operation device 300 to electrically drive the endoscope 100. Alternatively, in a case where the motor is an external motor outside the drive control device 200, the drive control device 200 transmits a control signal to the external motor based on the operation input to the operation device 300 and controls electric driving. In addition, the drive control device 200 may drive a built-in pump or the like based on the operation input to the operation device 300 and cause the endoscope 100 to perform air supply/suction. The air supply/suction is performed through an air supply/suction tube arranged on the internal path 101. One end of the air supply/suction tube opens in the tip portion 130 of the endoscope 100, and the other end thereof is connected to the drive control device 200 through the connector 201. Note that the treatment tool channel may be extended to the connector 201, and the treatment tool channel may also serve as the air supply/suction tube.

Figure 5:
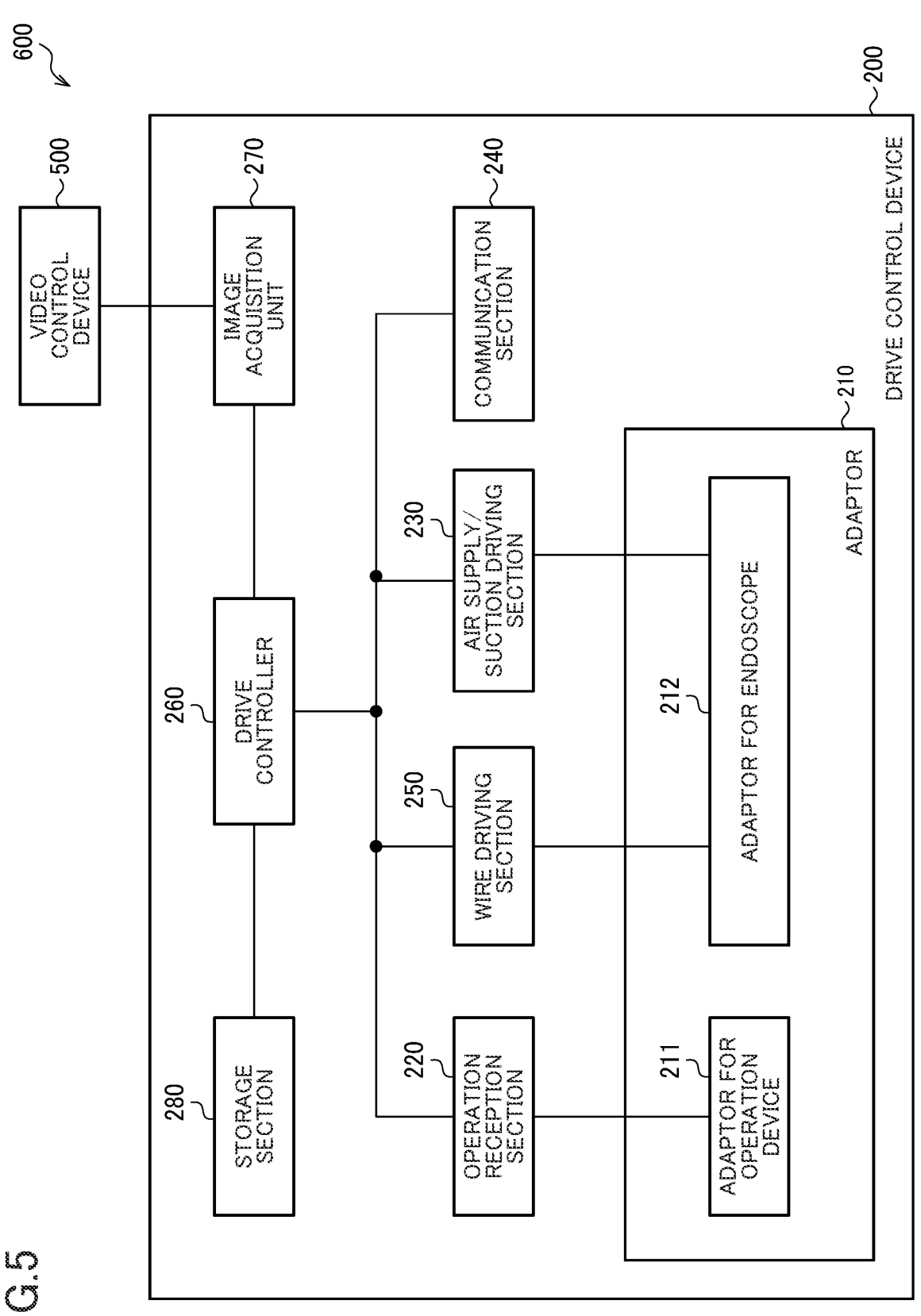
FIG. 5 is a diagram for describing a configuration example of a drive control device.

A block diagram in FIG. 5 illustrates a detailed configuration example of the drive control device 200. The drive control device 200 includes an image acquisition section 270, a storage section 280, a drive controller 260, an operation reception section 220, a wire driving section 250, an air supply/suction driving section 230, a communication section 240, and an adaptor 210.

The adaptor 210 includes an adaptor for the operation device 211 to which the operation cable 301 is detachably connected and an adaptor for the endoscope 212 to which the connector 201 of the endoscope 100 is detachably connected.

The wire driving section 250 performs driving for the bending operation of the bending portion 102 of the endoscope 100 or the operation of the raising base of the treatment tool 400, based on a control signal from the drive controller 260. The wire driving section 250 includes a motor unit for the bending operation that drives the bending portion 102 of the endoscope 100 and a motor unit for the raising base that drives the raising base. The adaptor for the endoscope 212 has a coupling mechanism for the bending operation for coupling to the bending wire on the endoscope 100 side. The motor unit for the bending operation drives the coupling mechanism, whereby driving force of the driving is transmitted to the bending wire on the endoscope 100 side. The adaptor for the endoscope 212 has a coupling mechanism for the raising base for coupling to the wire for the raising base on the endoscope 100 side. The motor unit for the raising base drives the coupling mechanism, whereby driving force of the driving is transmitted to the wire for the raising base on the endoscope 100 side.

The air supply/suction driving section 230 performs driving for air supply/suction of the endoscope 100 based on the control signal from the drive controller 260. The air supply/suction driving section 230 is connected to the air supply/suction tube of the endoscope 100 through the adaptor for the endoscope 212. The air supply/suction driving section 230 is provided with a pump or the like, supplies the air to the air supply/suction tube, and sucks the air from an air supply/suction tube 172.

The communication section 240 performs communication with a driving device arranged outside the drive control device 200. Communication may be either wireless communication or wired communication. The driving device arranged outside is the advancing/retreating driving device 800 that performs advancing/retreating or a roll driving device that performs rolling, but may be an overtube driving device that changes hardness of the overtube 710, a balloon driving device that changes a diameter of the balloon 720, or the like.

The drive controller 260 controls the advancing/retreating of the endoscope 100, the bending operation and the rolling, the rising angle of the treatment tool 400 formed by the raising base, and the air supply/suction by the endoscope 100. In a case where control of the hardness of the overtube 710 or the diameter of the balloon 720 is performed by means of electric driving, the drive controller 260 performs the control. The drive controller 260 can be implemented by, for example, the above-mentioned processor. For example, the storage section 280, which will be described later, stores a computer-readable program. The program is executed by the processor, whereby functions of the drive controller 260 are implemented as processing.

The image acquisition section 270 is a communication interface that receives image data of the endoscope image from the video control device 500 through wired communication or wireless communication. The image acquisition section 270 outputs the received image data of the endoscope image to the drive controller 260.

In addition, the image acquisition section 270 acquires image data of a transmissive image of the abdomen of the patient. The image data is used in a first determination (step S50), which will be described later with reference to FIG. 9. The transmissive image is, for example, an ERCP image captured by an X-ray imaging device for surgery or a CT device, or a magnetic resonance cholangiopancreatography (MRCP) image captured by a magnetic resonance imaging (MRI) device. MRCP is an abbreviation for magnetic resonance cholangiopancreatography. The transmissive image is captured at least when the first determination (step S50) is performed, but may be captured in real time after the contrast-enhancement illustrated in FIG. 2.

The storage section 280 stores information of a program and the like regarding drive control of the endoscope 100. The storage section 280 can be implemented by a storage device such as the semiconductor memory and the magnetic storage device that have been described above. Note that the storage section 280 may store part or the whole of the program regarding the flow described in FIG. 8 or the subsequent drawings.

Additionally, the drive controller 260 may be capable of performing control in a plurality of types of operation modes. Examples of the operation modes include a manual mode in which the operator manually operates electric driving of the endoscope 100 or the like, and an automatic mode in which electric driving of the endoscope 100 or the like is automatically controlled based on the endoscope image. For example, the positioning step described above with reference to FIG. 2 may be performed in the automatic mode. This enables automation of the positioning step. Note that in the automatic mode, at least one of the advancing/retreating of the endoscope 100, the bending operation, or the rolling is only required to be automated. That is, part of the rising angle of the treatment tool 400 formed by the raising base, the control of the hardness of the overtube 710, the control of the diameter of the balloon 720, the air supply/suction of the endoscope 100, the advancing/retreating of the endoscope 100, the bending operation, or rolling may be manually operated.

Figure 6:
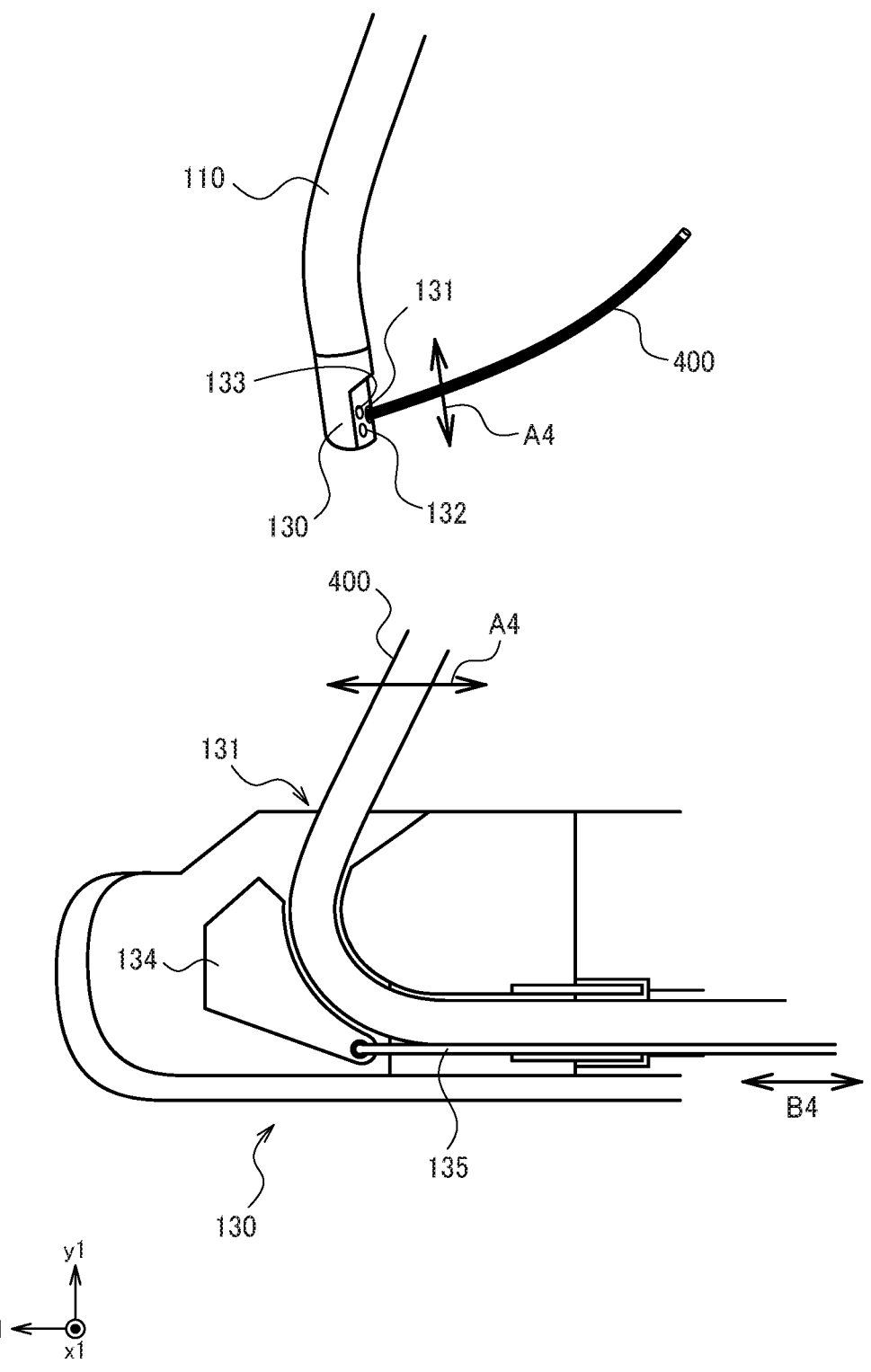
FIG. 6 is a diagram for describing an example of a tip portion of an endoscope, the tip portion including a raising base of a treatment tool.

FIG. 6 illustrates a detailed configuration example of the tip portion 130 of the endoscope including the raising base of the treatment tool 400. The upper drawing is an external view of the tip portion 130. An opening 131 of the treatment tool channel, a camera 132, and an illumination lens 133 are arranged on the side surface of the tip portion 130. As illustrated in the lower drawing, assume that a direction that is parallel to the axis line direction of the tip portion 130 is a z1-direction, a direction that is parallel to a line-of-sight direction of the camera 132 is a y1-direction, and a direction orthogonal to the z1- and y1-directions is an x1-direction. The lower drawing is a cross-sectional view of the tip portion 130 in a plane that is parallel to a y1-z1 plane of the treatment tool channel and that passes through the opening 131 of the treatment tool channel.

The tip portion 130 includes a raising base 134 and a wire for the raising base 135. The raising base 134 can pivotally move about an axis that is parallel to the x1-direction. One end of the wire for the raising base 135 is connected to the raising base 134, and the other end thereof is connected to the drive control device 200 through the connector 201. The wire driving section 250 of the drive control device 200 presses/pulls the wire for the raising base 135 as indicated in B4, whereby the raising base 134 pivotally moves, and the rising angle of the treatment tool 400 changes as indicated in A4. The rising angle is an angle of the treatment tool 400 that projects from the opening 131, and can be defined by, for example, an angle formed between the treatment tool 400 that projects from the opening 131 and the z1-direction.

In addition, the drive controller 260 may control the endoscope operation or the rising angle of the treatment tool 400 so that the tip of the treatment tool 400 faces a direction of the orifice of the luminal tissues based on the endoscope image. Alternatively, the drive controller 260 may control the endoscope operation or the rising angle of the treatment tool 400 so that the tip of the treatment tool 400 faces a traveling direction of the biliary duct based on the endoscope image. For example, assuming that information of the traveling direction of the biliary duct is added to a criterion image, the drive controller 260 may perform control so that the tip of the treatment tool 400 faces the traveling direction of the biliary duct based on the information. Note that the traveling direction mentioned herein is a two-dimensional direction on the endoscope image. That is, on the endoscope image, the drive controller 260 controls the endoscope operation or the rising angle of the treatment tool 400 so that the traveling direction of the biliary duct and the direction the treatment tool 400 faces become substantially parallel. However, in a case where three-dimensional information of the traveling direction of the biliary duct can be obtained from a CT image or the like, the drive controller 260 may perform control so that the traveling direction of the biliary duct and the direction the treatment tool 400 faces to be substantially parallel.

Figure 7:
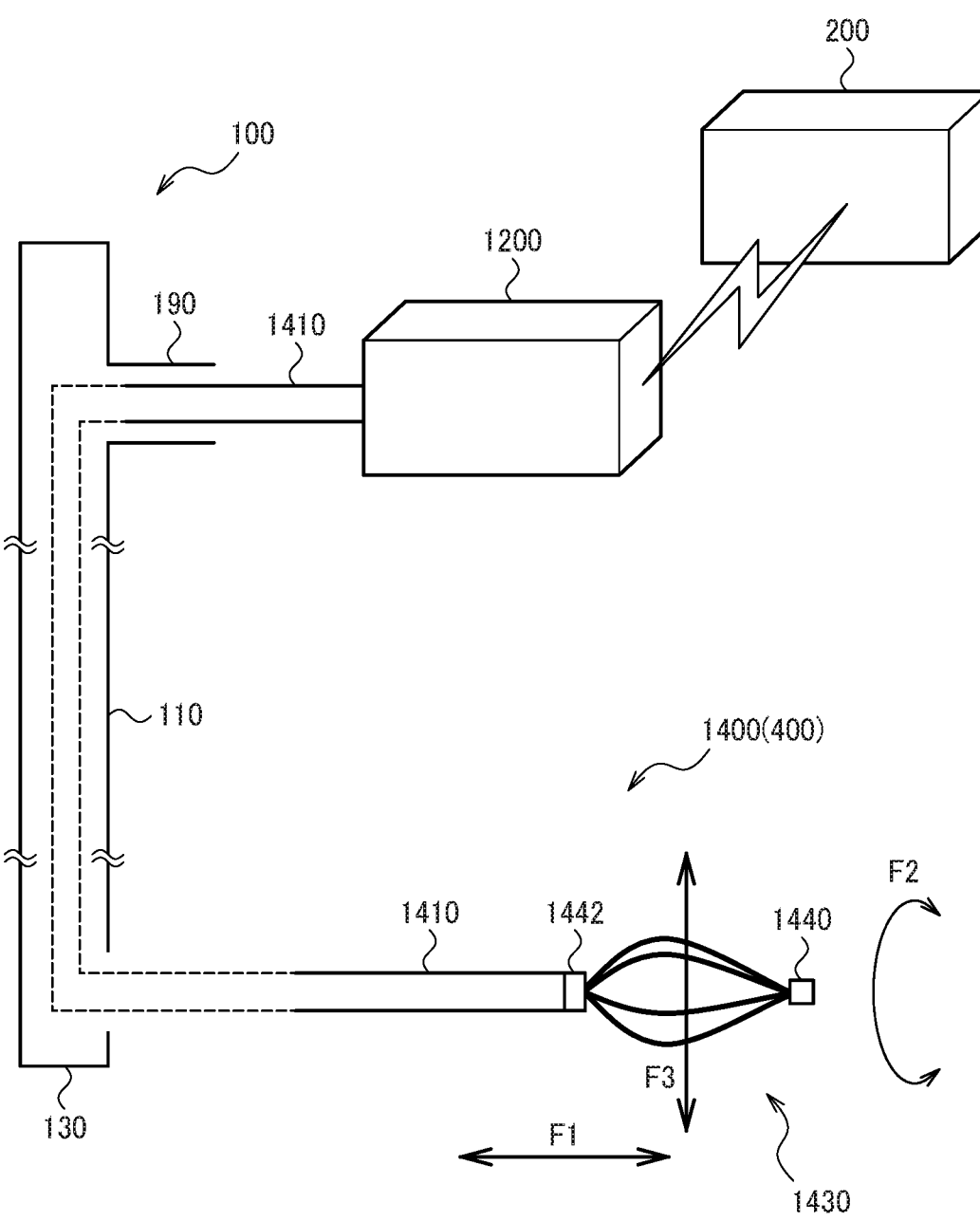
FIG. 7 is a diagram for describing an example of control of a basket treatment tool.

FIG. 7 exemplifies drive control of a basket treatment tool 1400 as an example of the treatment tool 400 in accordance with the present embodiment. Note that the above-mentioned cannula or the like for performing the ERCP is also an example of the treatment tool 400 that can be used for treatment in accordance with the present embodiment, but is configured using publicly known features, so that a description thereof is omitted.

Note that in the endoscope 100 in FIG. 7, a configuration other than the insertion opening 190, the insertion portion 110, and the tip portion 130 is not illustrated. The endoscope 100 in FIG. 7 is illustrated for conceptually indicating the insertion opening 190, the insertion portion 110, and the tip portion 130, and does not limit a structure or the like of the endoscope 100 in any way. For example, FIG. 7 illustrates that the rising angle of the treatment tool 400 serving as the basket treatment tool 1400 is 90 degrees, but this does not limit the rising angle of the treatment tool 400 in accordance with the present embodiment to 90 degrees.

The basket treatment tool 1400 includes, for example, a first sheath 1410 and a basket 1430, and is electrically driven by a basket driving device 1200. Note that the basket treatment tool 1400 may be, for example, configured to include a plurality of sheathes, and details thereof will be described later with reference to FIG. 14. For example, the basket treatment tool 1400 for a purpose of extraction of a stone and the basket treatment tool 1400 for a purpose of crushing of a stone are configured to be used differently, and the respective basket treatment tools 1400 may be projectable from the tip portion 130.

The basket driving device 1200 includes, for example, a mechanism such as a motor and a rack-and-pinion. This enables a configuration of a slide mechanism for advancing/retreating an operation wire 1444 or the like using rotative force of the motor. The slide mechanism will be described later. Accordingly, the basket driving device 1200 can control the advancing/retreating of the basket 1430. The basket driving device 1200 may use a similar mechanism to perform control for advancing/retreating the first sheath 1410 in a direction indicated in F1. Note that a detailed structure of a motor or the like included in the basket driving device 1200 is publicly known, and thus illustration thereof is omitted.

The basket driving device 1200 is connected to the drive control device 200 through the communication section 240 illustrated in FIG. 5. The connection mentioned herein is a wireless communication connection illustrated in FIG. 7, but may be a wired communication connection.

The drive control device 200 controls an operation of the basket driving device 1200 through the communication connection. For example, the drive control device 200 automatically controls crushing of a gallstone G using the basket treatment tool 1400, pulling of the basket treatment tool 1400, or the like. That is, the drive control device 200 may control the basket treatment tool 1400 with the above-mentioned automatic mode. In the automatic mode, part of a drive mechanism of the basket treatment tool 1400 is only required to be automated.

As the above-mentioned manual mode, the operator may be able to manually operate the basket treatment tool 1400. That is, the drive control device 200 may further include an operation input section for the basket treatment tool with which the operator can operate the basket treatment tool 1400. The operation input section for the basket treatment tool may be integrated with the operation device 300 in FIG. 4, or may be configured as another controller aside from the operation device 300.

The operation input section for the basket treatment tool may be arranged in the basket driving device 1200. The operation input section for the basket treatment tool includes, for example, a dial, a joy stick, an arrow key, a button, and a switch, a touch panel, and/or the like. This allows, for example, the operator to advance/retreat the operation wire 1444 at a predetermined distance. Note that an outer appearance of the operation input section for the basket treatment tool is publicly known, so that illustration thereof is omitted.

In addition, part of functions of the basket driving device 1200 may be integrated with those of the drive control device 200. For example, a wire driving section 250 illustrated in FIG. 5 and the like may be capable of controlling drive of the operation wire 1444 of the basket treatment tool 1400.

The basket 1430 includes a plurality of elastic wires. The elastic wires on the tip side are tied together with a tip member 1440, and the elastic wires on the base end side are tied together with a coupling member 1442. Note that the number of elastic wires is not limited to four, and is determined as appropriate. For example, the number of elastic wires of the basket treatment tool 1400 for the purpose of extraction of the stone may be made larger than the number of elastic wires of the basket treatment tool 1400 for the purpose of crushing of the stone.

The elastic wires of the basket 1430 are self-urged so as to be bending outward in substantially identical shapes. In addition, the elastic wires are arranged at equal angular intervals when viewed from a direction from the tip member

1440 toward the first sheath 1410. With this configuration, the basket 1430 is formed in a contracted state while being pulled into the first sheath 1410, and is formed in a substantially basket shape in a state of projecting from the first sheath 1410.

The coupling member 1442 is arranged at the tip of the operation wire 1444, which is not illustrated in FIG. 7. For example, in a case of an operation in the manual mode, the operator inserts the first sheath 1410 into the biliary duct at a desired position through the tip portion 130 in a state where the basket 1430 is pulled into the first sheath 1410. The operator then performs an operation of pushing the operation wire 1444 toward the tip side. With this operation, the basket 1430 is projected from the first sheath in a direction indicated in F1, and the basket 1430 is formed in the substantially basket shape.

Note that the basket 1430 is illustrated in FIG. 7 in a substantially basket shape formed of bending lines, but the shape is not limited thereto. The basket 1430 may be, for example, in a substantially basket shape formed of folding points and straight lines. Various shapes have been proposed as publicly known shapes. Note that in the present embodiment, the shape of the basket 1430 is assumed to be optimized for extraction or the like of the gallstone G.

Note that the basket driving device 1200 may further include a mechanism of, after projection of the basket 1430 from the first sheath 1410, further contracting the substantially basket shape and expanding the basket 1430 again. For example, in the case of the operation in the manual mode, the operator performs an operation of sliding the operation wire 1444 toward the base end side and partially fetching the coupling member 1442 and part of the basket 1430 in the first sheath 1410, and can thereby contract/expand the basket 1430 in a direction indicated in F3.

In addition, the basket driving device 1200 may be provided with, for example, a mechanism for rotating the coupling member 1442 and the operation wire 1444 about an axis of the guide wire. For example. the tip member 1440 is inserted through the guide wire, which is not illustrated in FIG. 7, and a handle or the like that rotates the operation wire 1444 about the guide wire is arranged. In the case of the operation in the manual mode, the operator operates the handle or the like, and can thereby rotate the basket 1430 in a direction indicated in F2. This configuration facilitates fetching of the gallstone G in the basket 1430.

Additionally, the basket treatment tool 1400 in accordance with the present embodiment may couple part of the plurality of elastic wires to a rotary shaft of the coupling member 1442. The rotary shaft is not illustrated. With this configuration, for example, rotating the operation wire 1444 temporarily changes the shape of the basket 1430, and can facilitate fetching of the gallstone G.

In this manner, for example, in the case of the operation in the manual mode, the operator uses the basket driving device 1200 to perform advancing/retreating, opening/closing, rotation, or the like of the basket 1430 until the gallstone G is fetched in the basket 1430, while observing the transmissive image displayed on the display device 900. After the gallstone G is fetched in the basket 1430, the operator uses the basket driving device 1200 to perform an operation of pulling out the basket treatment tool 1400 from the biliary duct, and can thereby remove the gallstone G from the papillary orifice.

While the above description has been given of the example in a case where the basket treatment tool 1400 is operated in the manual mode, the operations may be performed in the automatic mode. The specification of United States Patent Application Publication No. 2007/0185377 discloses an example of advancing/retreating and opening/closing a basket forceps in accordance with an embedded program.

However, when the gallstone has a large size, it is difficult to pull the basket treatment tool 1400 and remove the gallstone G from the papillary orifice. If each of advancing/retreating, opening/closing, and removal is automatically performed by an embedded program in a mechanical manner, there is a possibility for applying a load to the vicinity of the papillary orifice, and a possibility for failure to remove the gallstone G completely. Addition of treatment for enlarging the vicinity of the papillary orifice complicates the manipulation, and increases a burden on the operator. This increases a burden on the patient. In addition, it is difficult for the operator to accurately determine whether the size of the gallstone G fetched in the basket 1430 is a size that allows the gallstone G to easily pass through the papillary orifice.

A processing example regarding removal of the gallstone in accordance with the present embodiment is described with reference to FIG. 8. The control device 600 performs contrast-enhancement processing (step S10). Specifically, the control device 600 performs a series of processing regarding the flow of the ERCP described above with reference to FIG. 2. Thereafter, the control device 600 performs gallstone removal processing (step S20). Although not illustrated in FIG. 8, it is possible to implement a processing example of performing the gallstone removal processing (step S20) after performing the processing of fetching the gallstone G in the basket 1430, but it is also possible to implement a processing example of including the processing of fetching the gallstone G in the basket 1430 in the gallstone removal processing (step S20). Details thereof will be described later.

Figure 8:
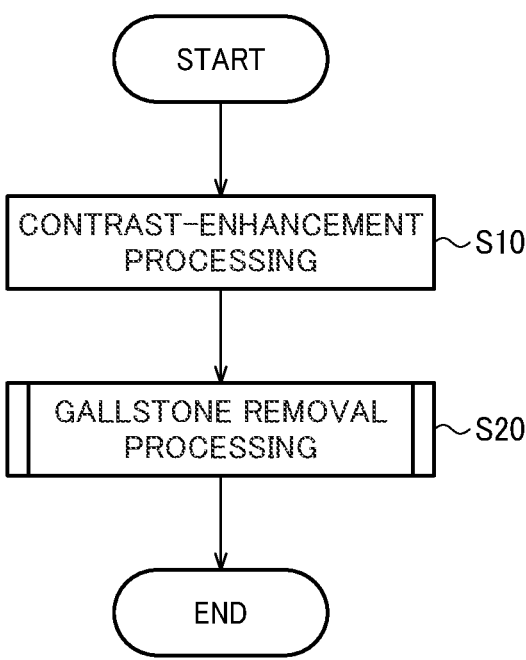
FIG. 8 is a flowchart describing a processing example of a method in accordance with the present embodiment.

Note that the flow in FIG. 8 can be modified in various manners. For example, while it is described that the flow in FIG. 8 is completed at one time, the flow may be repeatedly performed on a periodic basis by, for example, timer interruption processing or the like. In this case, the control device 600 may perform only imaging processing as the contrast-enhancement processing (step S10) for the second or subsequent times, and the control device 600 may repeatedly perform the gallstone removal processing (step S20) while the operator observes the captured transmissive image.

Subsequently, the gallstone removal processing (step S20) is described in detail. The control device 600 performs the first determination (step S50) or a second determination (step S50) in the gallstone removal processing (step S20). Note that the control device 600 may perform both the first determination (step S50) and the second determination (step S60), and may perform, for example, in such a manner as a processing example described in FIG. 9.

Figure 9:
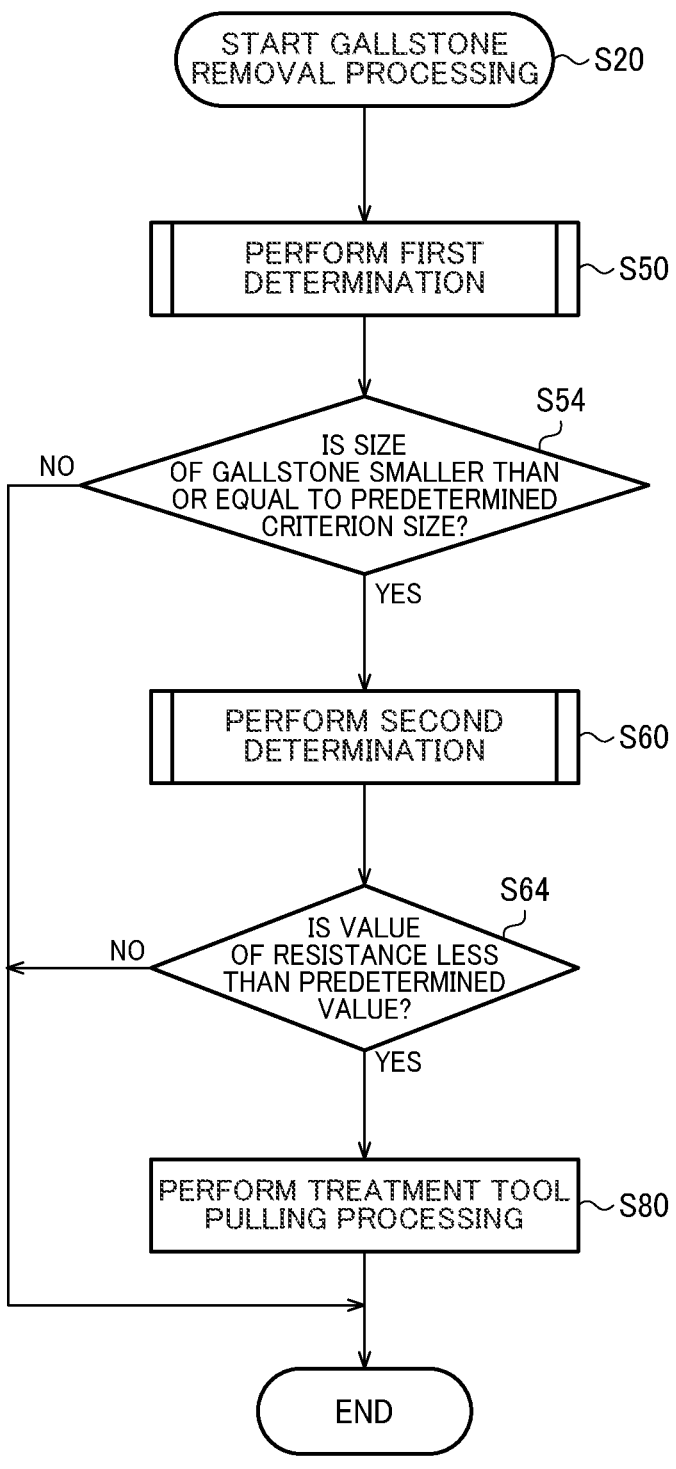
FIG. 9 is a flowchart describing a processing example of gallstone removal processing.

Note that details of each processing of the gallstone removal processing (step S20) will be described below along the flowchart in FIG. 9 for the purpose of convenience, but not all the processing in FIG. 9 needs be performed. That is, which of the processing in FIG. 9 is included in the gallstone removal processing (step S20) is only required to be determined by the operator or the like as appropriate. For example, in a case where the gallstone removal processing (step S20) is performed using the first determination (step S50), the operator or the like is only required to install software based on the flowchart that omits the second determination (step S60) and step S64 in the control device 600 or the like. Similarly, for example, in a case where the gallstone removal processing (step S20) is performed using the second determination (step S60), the operator or the like is only required to install software based on the flowchart that omits the first determination (step S50) and step S54 in the control device 600 or the like.

The control device 600 first performs the first determination (step S50). The control device 600 then performs processing of determining whether or not the size of the gallstone G as a result of the first determination (step S50) is smaller than or equal to a predetermined criterion size (step S54). Details of the first determination (step S50) and the predetermined criterion size in step S54 will be described later with reference to FIG. 10 and the like.

When it is determined that the size of the gallstone G is smaller than or equal to the predetermined criterion size (YES in step S54), the control device 600 performs the second determination (step S60), which will be described later.

Figure 10:
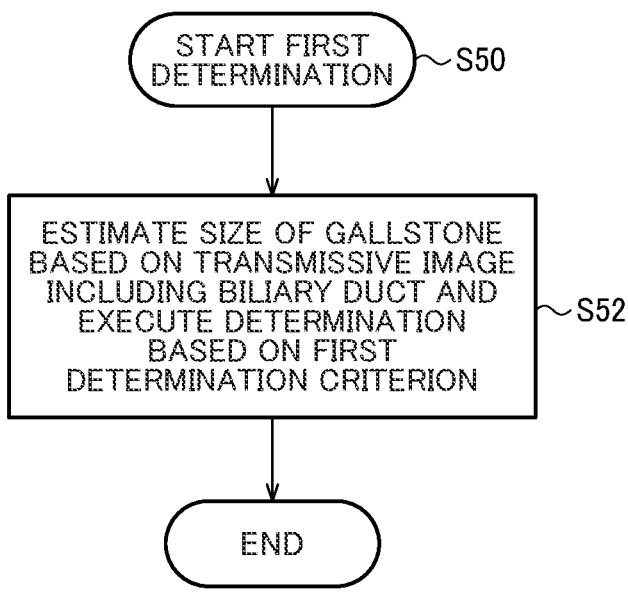
FIG. 10 is a flowchart describing an example of a first determination.

Details of the first determination (step S50) and the like are now described with reference to FIGS. 10 and 11. The control device 600 estimates the size of the gallstone G based on the transmissive image including the biliary duct and performs processing of executing a determination based on a first determination criterion (step S52), and ends the flow of the first determination (step S50).

Figure 11:
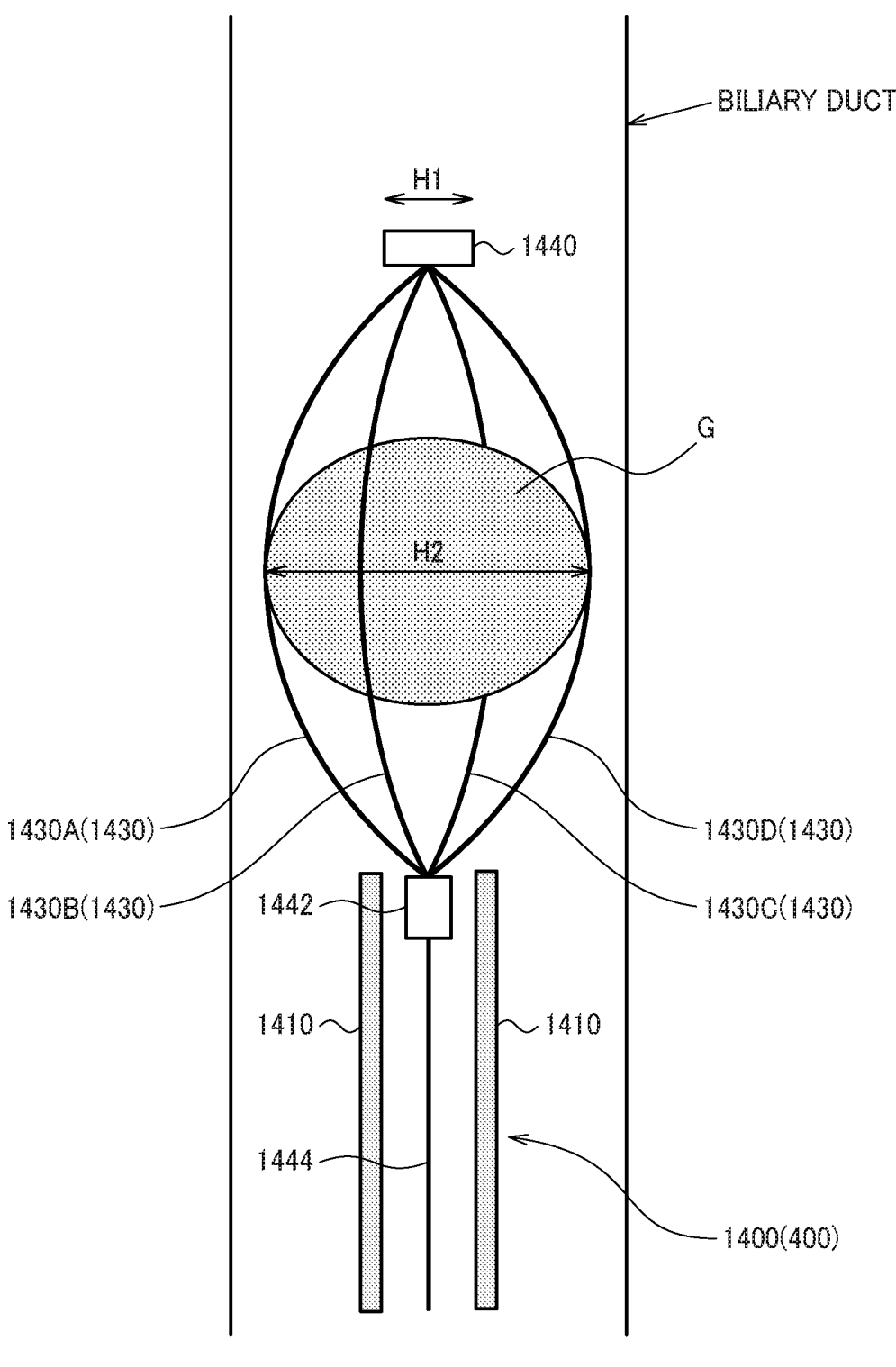
FIG. 11 is a diagram for describing an example of a first determination criteria.

For example, as illustrated in FIG. 11, assume a situation where the operator can grasp that the gallstone G has been fetched in the basket treatment tool 1400 from the transmissive image or the like. A radiopaque marker is preliminarily added to the tip member 1440 of the basket treatment tool 1400 in accordance with the present embodiment. The radiopaque marker is a material including, for example, barium sulfate, tungsten, bismuth oxide, gold, platinum, or the like. This allows the operator to clearly recognize the tip member 1440 in the transmissive image.

The first determination criterion is determined, for example, based on whether or not the size of the gallstone G indicated in H2 exceeds the predetermined criterion size. The predetermined criterion size is, for example, a size obtained by multiplying a size indicated in H1 by a predetermined coefficient. The predetermined coefficient is a constant that is preliminarily set by the operator or the like, but may be changed as appropriate. For example, the control device 600 performs processing of extracting each of an image portion of the tip member 1440 and an image portion of the gallstone G from the captured endoscope image, processing of estimating the size indicated in H2 based on the image portion of the tip member 1440 and the image portion of the gallstone G, and processing of determining whether the size indicated in H2 satisfies the first determination criterion. For example, equalizing the size indicated in H1 and the known size of the tip member 1440 allows the control device 600 to estimate the size indicated in H2. With this configuration, the control device 600 can determine whether the size indicated in H2 satisfies the first determination criterion.

Note that in the basket treatment tool 1400 illustrated in FIG. 11, the basket 1430 includes four elastic wires 1430A, 1430B, 1430C, and 1430D, but a configuration of the basket 1430 is not limited to the configuration illustrated in FIG. 11 as described above.

A part to which the radiopaque marker is added is not limited to the tip member 1440, and may be, for example, the first sheath 1410, the coupling member 1442, the elastic wires 1430A to 1430D of the basket 1430, or the guide wire, and the control device 600 is only required to specifically grasp the size.

Back to FIG. 9, the description continues. In step S54, the control device 600 determines whether the estimated size of the gallstone G is smaller than or equal to the predetermined criterion size. In other words, in step S54, the control device 600 determines whether the estimated size of the gallstone G satisfies the first determination criterion. When it is determined that the size of the gallstone G is larger than the predetermined criterion size (NO in step S54), the control device 600 ends the flow without performing treatment tool pulling processing (step S80), which will be described later. This is because the determination as NO in step S54 by the control device 600 means that the size of the gallstone G present in the biliary duct is too large with respect to a size of the papillary orifice, and it is not appropriate to perform the treatment tool pulling processing (step S80) under this situation.

On the other hand, when it is determined that the size of the gallstone G is smaller than or equal to the predetermined criterion size (YES in step S54), the control device 600 performs the second determination (step S60). The control device 600 then performs processing of determining whether or not resistance as a result of the second determination (step S60) is less than a predetermined value (step S64).

Figure 12:
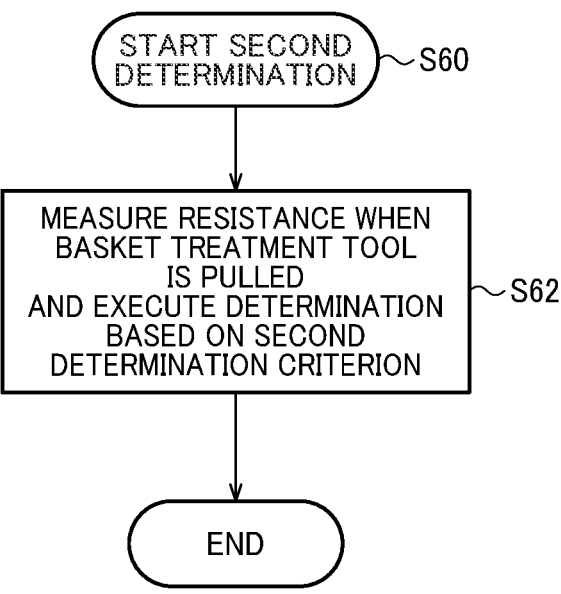
FIG. 12 is a flowchart describing an example of a second determination.

The second determination (step S60) is now described in more detail with reference to FIG. 12. The control device 600 measures force when the basket treatment tool 1400 is pulled, performs processing of executing a determination based on a second determination criterion (step S62), and ends the flow of the second determination (step S60).

The second determination criterion is determined based on whether a value of resistance shown when the basket treatment tool 1400 is pulled to the vicinity of the papillary orifice at a predetermined speed in a state where the gallstone G is fetched in the basket 1430 is less than a predetermined value. That is, the second determination (step S60) is on the premise that the gallstone G has been fetched in the basket 1430. The value of resistance is a value based on a measured value measured by a strain gauge that is attached to the basket treatment tool 1400 at a predetermined position of the basket treatment tool 1400 and that is not illustrated, but is not limited thereto, and may be, for example, a value based on a measured value of torque of a motor included in the basket driving device 1200. The value of resistance may be the measured value itself measured by the strain gauge or the like. The measured value may be converted to another value. The operator or the like can set the measured value as appropriate. Another value is, for example, a value obtained by staging measured values measured by the strain gauge or the like for every predetermined measured range.

In step S64, the control device 600 then determines whether the value of resistance is less than a predetermined value. In other words, in step S64, the control device 600 determines whether the value of resistance satisfies the second determination criterion.

Back to FIG. 9, the description continues. When it is determined that resistance is less than the predetermined value (YES in step S64), the control device 600 performs the treatment tool pulling processing (step S80), and ends the flow.

The treatment tool pulling processing (step S80) is, for example, control for transmitting, to the basket driving device 1200 through the drive control device 200, an instruction for electrically retreating the first sheath 1410 and the operation wire 1444 to a base bottom side in a state where the gallstone G is fetched in the basket 1430. Note that the control device 600 may perform processing of notifying the operator of an instruction for pulling out the basket treatment tool 1400 from the biliary duct in the state where the gallstone G is fetched in the basket 1430.

On the other hand, when it is determined that resistance is greater than or equal to the predetermined value (NO in step S64), the control device 600 ends the flow without performing the treatment tool pulling processing (step S80). This is because, for example, in a case where the value of resistance is greatly elevated when the basket treatment tool 1400 is pulled to the vicinity of the papillary orifice, a reason such as the size of the gallstone G present in the biliary duct being too large with respect to the size of the papillary orifice can be assumed, and it is not appropriate to perform the treatment tool pulling processing (step S80). With this processing, pulling out the basket 1430 including the oversize gallstone G can prevent a load from being applied to the papillary portion or the like. Note that the control device 600 may perform processing of issuing a predetermined error.

In this manner, the medical system 10 in accordance with the present embodiment includes the basket treatment tool 1400 and the control device 600. The basket treatment tool 1400 is inserted into the biliary duct from the papillary orifice and capable of performing driving for opening/ closing and advancing/retreating. The control device 600 controls the driving of the basket treatment tool 1400. The control device 600 performs the first determination (step S50) or the second determination (step S60). The first determination (step S50) is to determine, based on the transmissive image including the biliary duct, whether the size of the gallstone G allows the basket treatment tool 1400 to remove the gallstone G from the papillary orifice. The second determination (step S60) is to determine, based on resistance when the basket treatment tool 1400 is pulled, whether the resistance allows the basket treatment tool 1400 to remove the gallstone G from the papillary orifice. When it is determined in the first determination (step S50) or the second determination (step S60) that the gallstone G is removable from the papillary orifice (YES in step S54 or YES in step S64), the control device 600 performs control for removing the gallstone G from the papillary orifice using the basket treatment tool 1400 (step S80).

With the inclusion of the basket treatment tool 1400 and the control device 600, the medical system 10 in accordance with the present embodiment can insert the basket treatment tool 1400 from the papillary orifice into the biliary duct and perform driving for opening/closing and advancing/retreating, and can thereby perform treatment for removing the gallstone G in the biliary duct. The control device 600 can perform the first determination (step S50) or the second determination (step S60), and thereby enables structuring of the medical system 10 capable of determining whether the size of the gallstone G fetched in the basket treatment tool 1400 enables removal of the gallstone G from the papillary orifice. The control device 600 controls the basket treatment tool 1400 to remove the gallstone G from the papillary orifice only when it is determined that the size of the gallstone G fetched in the basket treatment tool 1400 makes the gallstone G removable from the papillary orifice, and can thereby perform safe treatment on the patient. The method of determining whether the size of the gallstone G enables removal of the gallstone G from the papillary orifice has not been proposed so far.

The present embodiment may be implemented as an operation method for the medical system 10 as follows. That is, the operation method for the medical system 10 in accordance with the present embodiment includes a step of causing the basket treatment tool 1400 to perform driving for opening/closing and advancing/retreating. The basket treatment tool 1400 is inserted into the biliary duct from the papillary orifice and capable of performing driving for opening/closing and advancing/retreating. The operation method for the medical system 10 includes a step of performing the first determination (step S50) or the second determination (step S60). The first determination (step S50) is to determine, based on the transmissive image including the biliary duct, whether the size of the gallstone G allows the basket treatment tool 1400 to remove the gallstone G from the papillary orifice. The second determination (step S60) is to determine, based on resistance when the basket treatment tool 1400 is pulled, whether the resistance allows the basket treatment tool 1400 to remove the gallstone G from the papillary orifice. The operation method for the medical system 10 includes a step of, when it is determined in the first determination (step S50) or the second determination (step S60) that the gallstone G is removable from the papillary orifice (YES in step S54 or YES in step S64), performing control for removing the gallstone G from the papillary orifice using the basket treatment tool 1400 (step S80). This enables obtaining of an effect that is similar to the above-mentioned effect.

The method in accordance with the present embodiment may be implemented as a non-transitory information storage medium as follows. That is, the non-transitory information storage medium in accordance with the present embodiment stores a program that causes a computer to execute the step of causing the basket treatment tool 1400 to perform driving for opening/closing and advancing/retreating. The basket treatment tool 1400 is inserted into the biliary duct from the papillary orifice and capable of performing driving for opening/closing and advancing/retreating. The non-transitory information storage medium stores a program that causes the computer to execute the first determination or the second determination (step S50 or step S60). The first determination (step S50) is to determine, based on the transmissive image including the biliary duct, whether the size of the gallstone G allows the basket treatment tool 1400 to remove the gallstone G from the papillary orifice. The second determination (step S60) is to determine, based on resistance when the basket treatment tool 1400 is pulled, whether the resistance allows the basket treatment tool 1400 to remove the gallstone G from the papillary orifice. When it is determined in the first determination (step S50) or the second determination (step S60) that the gallstone G is removable from the papillary orifice (YES in step S54 or YES in step S64), the non-transitory information storage medium stores a program that causes the computer to execute the step of performing control for removing the gallstone G from the papillary orifice using the basket treatment tool 1400 (step S80). This enables obtaining of an effect that is similar to the above-mentioned effect.

The method in accordance with the present embodiment is not limited to the above-mentioned method, and can be modified in various manners. In the following description, assume that the control device 600 is capable of electrically driving the basket treatment tool 1400 through the drive control device 200. That is, in the medical system 10 in accordance with the present embodiment, assume that he control device 600 controls the driving of the basket treatment tool 1400 by means of electric driving. This enables structuring of the medical system 10 that electrically drives the basket treatment tool 1400.

In the following description, assume that the transmissive image is an ERCP image or an MRCP image. That is, in the medical system 10 in accordance with the present embodiment, the transmissive image is the ERCP image or the MRCP image. This enables structuring of the medical system 10 using the ERCP image or the MRCP image.

Figure 13:
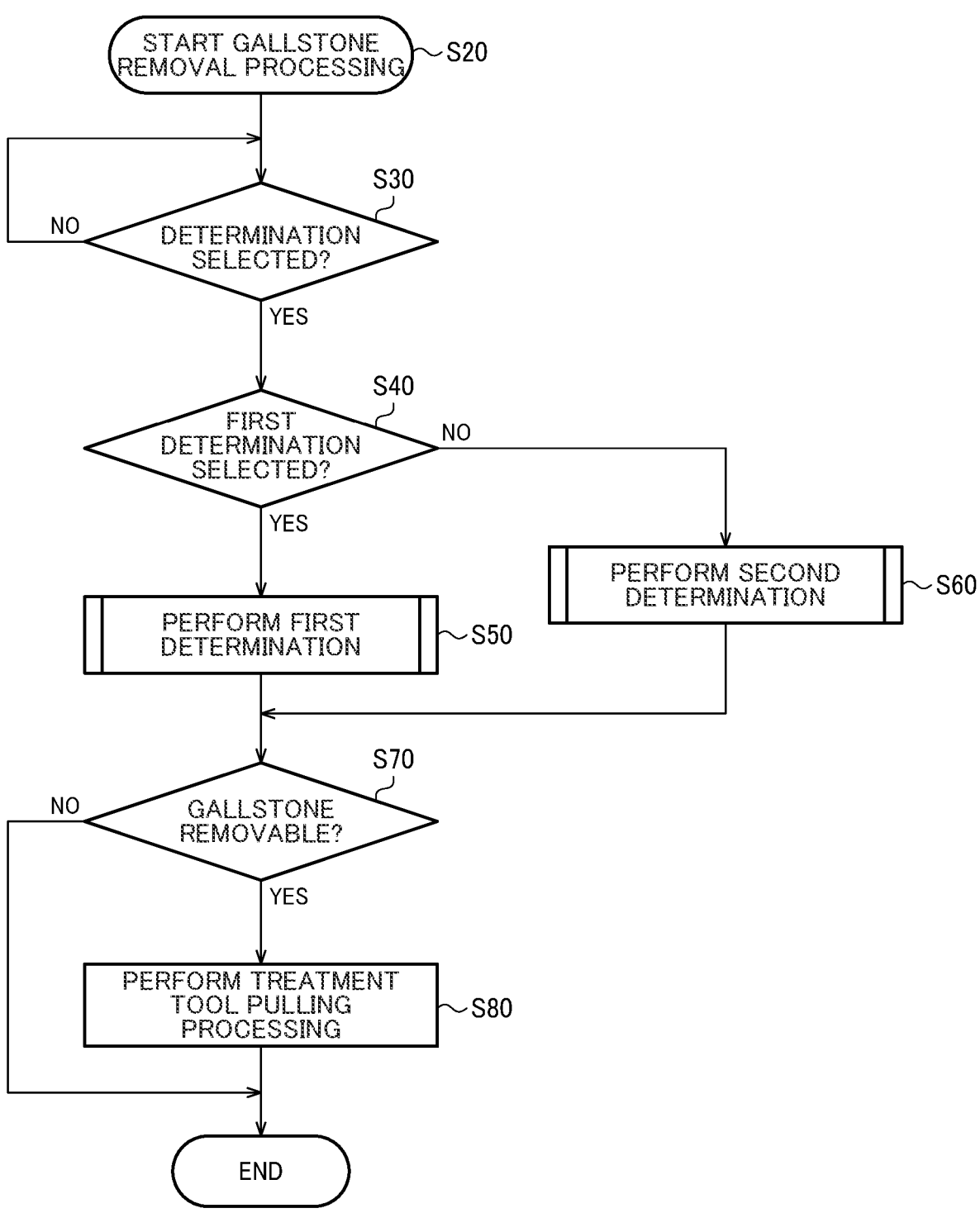
FIG. 13 is a flowchart describing another modification of the gallstone removal processing.

The gallstone removal processing (step S20) in accordance with the present embodiment may be implemented as a processing example as indicated in a flowchart in FIG. 13 as a modification. Note that in FIG. 13, a description of processing or the like overlapping with that in FIG. 9 is omitted as appropriate.

The control device 600 performs processing of determining whether or not the determination has been selected (step S30). The determination in step S30 is the first determination (step S50) and the second determination (step S60) described above. When the determination is not selected (NO in step S30), the control device 600 performs step S30 again. Although not illustrated, the control device 600 makes a notification to make the operator select the first determination (step S50) or the second determination (step S60). The notification may be made by, for example, a dedicated notification device, or may be displayed on the display device 900, and various methods can be adopted. In other words, the gallstone removal processing (step S20) does not proceed unless the operator selects the first determination (step S50) or the second determination (step S60).

On the other hand, when the determination is selected (YES in step S30), the control device 600 performs processing of determining whether or not the first determination (step S50) is selected (step S40). When the first determination is selected (YES in step S40), the control device 600 first performs the first determination (step S50). On the other hand, when the first determination (step S50) is not selected (NO in step S40), the control device 600 performs the second determination (step S60).

The control device 600 performs the first determination (step S50) or the second determination (step S60), and thereafter performs processing of determining whether or not the gallstone G is removable (step S70). A criterion regarding the determination in step S70 is the first determination criterion described in step S52 in FIG. 10 or the second determination criterion described in step S62 in FIG. 12.

When it is determined that the gallstone G is removable (YES in step S70), the control device 600 performs the treatment tool pulling processing (step S80), and ends the flow of the gallstone removal processing (step S20). On the other hand, when it is determined that the gallstone G is not removable (NO in step S70), the, control device 600 ends the flow without performing the treatment tool pulling processing (step S80).

As described above, the gallstone removal processing (step S20) in accordance with the present embodiment is processing of performing either the first determination (step S50) or the second determination (step S60), but may be processing of performing the second determination (step S60) after the first determination (step S50) as described in FIG. 9. That is, in the medical system 10 in accordance with the present embodiment, the control device 600 performs the first determination based on the transmissive image, and, when it is determined in the first determination (step S50) that the size of the gallstone G is smaller than or equal to the predetermined criterion size (YES in step S54), performs the second determination (step S60). This enables more appropriate determination as to whether the gallstone G is removable. Since the gallstone G cannot be observed from one direction in the first determination (step S50), there is a possibility that the size of the gallstone G is partially larger than the predetermined criterion size. There is a possibility that performing the treatment tool pulling processing (step S80) in such a case applies a load to the vicinity of the papillary orifice. In this regard, by application of the method in accordance with the present embodiment, the value of resistance as a result of the second determination (step S60) becomes a higher value than the predetermined value in such a case. Thus, it is determined as NO in step S64 is NO, and the treatment tool pulling processing (step S80) is not performed. Consequently, since the treatment tool pulling processing (step S80) is performed under a situation where the gallstone G is certainly removable, a burden on the patient can be reduced.

While FIG. 9 describes the processing example in which the control device 600 performs the first determination (step S50) before the second determination (step S60), a processing example of performing the second determination (step S60) before the first determination (step S50) may be employed. Accordingly, when it is determined as YES in step S64 due to, for example, occurrence of an unexpected malfunction in equipment used for measurement of resistance, the control device 600 performs the first determination (step S50) without immediately proceeding with the treatment tool pulling processing (step S80), and can thereby perform the treatment tool pulling processing (step S80) under a more certain situation.

Figure 14:
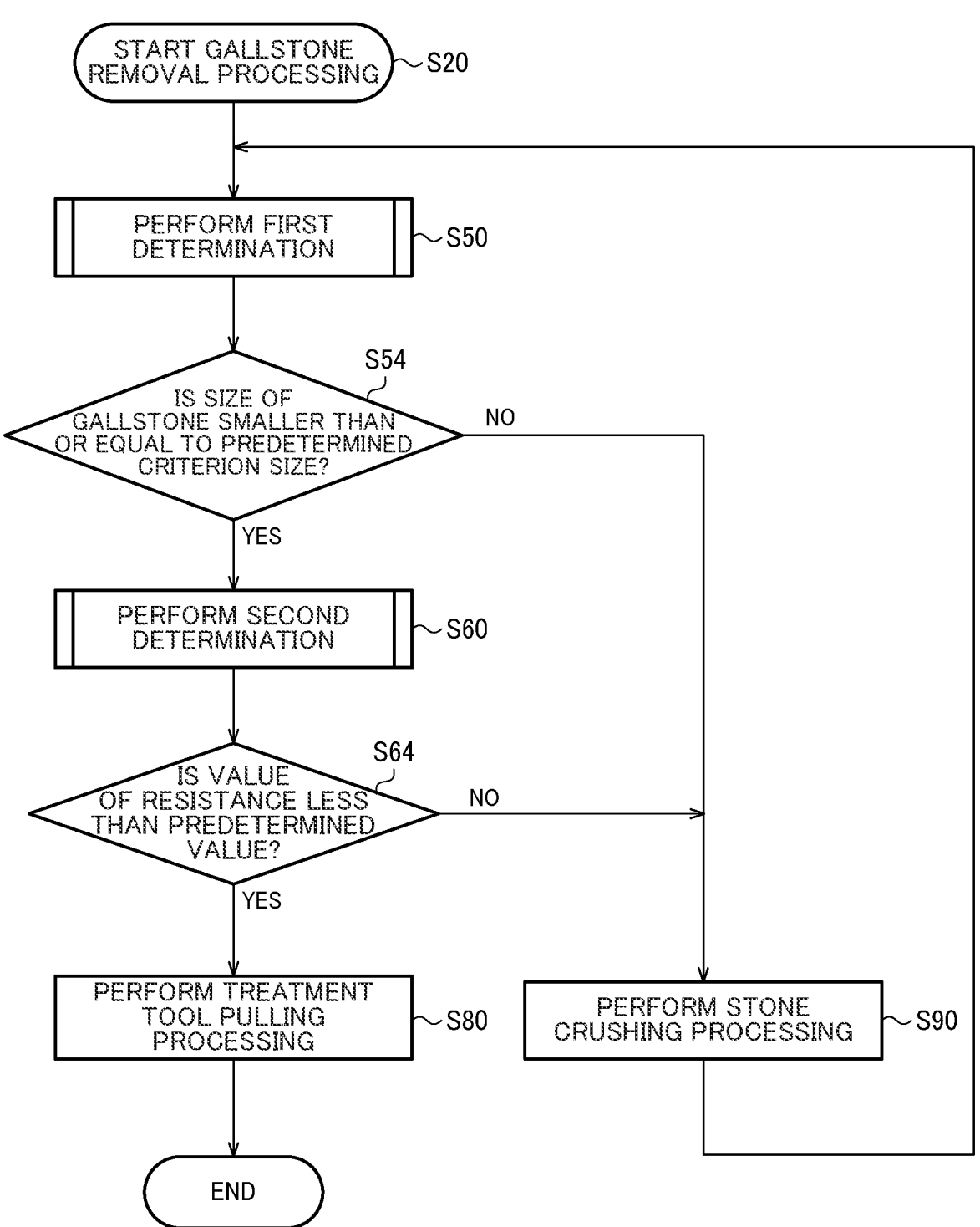
FIG. 14 is a flowchart describing another modification of the gallstone removal processing.

For example, the gallstone removal processing (step S20) described in FIG. 9 may be implemented as a processing example described in a flowchart in FIG. 14. The processing example in FIG. 14 is different from the processing example in FIG. 9 is that the control device 600 performs stone crushing processing (step S90) when it is determined as NO in step S54 described above or when it is determined as NO in step S64 described above. That is, in the medical system 10 in accordance with the present embodiment, when it is determined in the first determination (step S50) or the second determination (step S60) that the gallstone G is not removable from the papillary orifice (NO in step S54 or NO in step S64), the control device 600 performs control for crushing the gallstone (step S90). This can reduce the size of the gallstone G that makes it difficult for the gallstone G to be removed from the papillary orifice. Note that in FIG. 14, a description of processing overlapping with that in FIG. 9 is omitted as appropriate.

The stone crushing processing (step S90) is now described. For example, the control device 600 performs control for crushing the gallstone G with a laser device, which is not illustrated. A laser fiber of the laser device is inserted through the first sheath 1410 of the basket treatment tool 1400, and the control device 600 performs control for emitting a pulse laser from a tip of the laser fiber toward the gallstone G. The laser fiber is not illustrated. With this control, the gallstone G reaches high temperatures locally, and is crushed due to distortion caused by a difference in temperature, or the like. Note that a laser source appropriate for crushing the gallstone G is, for example, a neodymium-yttrium-aluminum-garnet (Nd-YAG) laser, a dye laser, or the like, but the operator can select a laser source as appropriate.

Additionally, the control device 600 may perform control for crushing the gallstone G with an electrohydraulic shock wave device, which is not illustrated. For example, a coaxial bipolar probe of the electrohydraulic shock wave device is inserted through the first sheath 1410 of the basket treatment tool 1400, and the control device 600 presses a tip of the probe against the gallstone G fetched in the basket 1430 to discharge an electrical current. With this control, shock waves are generated with vaporization of moisture in the vicinity of an electrode at the tip of the probe, and the gallstone G is crushed by the shock waves.

In the medical system 10 in accordance with the present embodiment, for example, the gallstone G may be crushed by the basket treatment tool 1400 itself. The basket treatment tool 1400 includes a second sheath 1420 that fulfills a function of crushing the gallstone G. This will be described in detail later with reference to FIG. 16. Note that the opening/closing operation of the basket 1430 described above with reference to FIG. 7 may be added to the stone crushing processing (step S90). Alternatively, the stone crushing processing (step S90) may be performed by only the opening/closing operation of the basket 1430. In this manner, in the medical system 10 in accordance with the present embodiment, the control device 600 performs control for crushing the gallstone G using the basket treatment tool 1400 (step S90). This eliminates the need for inclusion of the laser device or the electrohydraulic shock wave device described above, and can thereby simplify the configuration of the treatment tool for crushing the gallstone G.

Note that also in the processing example indicated in FIG. 14, not all the processing needs to be performed similarly to the above-mentioned processing example in FIG. 9. For example, the control device 600 may perform processing in which the second determination (step S60) and step S64 in FIG. 14 are omitted. That is, the control device 600 may perform, when it is determined as YES in step S54, control for performing the treatment tool pulling processing (step S80), and perform, when it is determined as NO in step S54, the stone crushing processing (step S90). That is, in the medical system 10 in accordance with the present embodiment, the control device 600, when it is determined in the first determination (step S50) that the size of the gallstone G is larger than the predetermined criterion size (NO in step S54), performs control for crushing the gallstone G (step S90). With this control, it is possible to grasp, through the transmissive image, that the gallstone G needs to be crushed to remove the gallstone G without applying a load to the vicinity of the papillary orifice.

The control device 600 then performs the first determination (step S50) again after the stone crushing processing (step S90). When it is determined as YES in step S54 after execution of the first determination (step S50) again, the control device 600 performs the treatment tool pulling processing (step S80) for the first time. That is, in the medical system 10 in accordance with the present embodiment, when it is determined in the first determination (step S50) that the size of the gallstone G is smaller than or equal to the predetermined criterion size (YES in step S54), the control device 600 performs control for removing the gallstone G (step S80). This control can prevent a load from being applied to the vicinity of the papillary orifice when the basket treatment tool 1400 is pulled to remove the gallstone G through observation of the transmissive image.

For example, the control device 600 may perform processing in which the first determination (step S50) and step S54 in FIG. 14 are omitted. That is, the control device 600 may perform control for performing the treatment tool pulling processing (step S80) when it is determined as YES in step S64, and performing the stone crushing processing (step S90) when it is determined as NO in step S64. That is, in the medical system 10 in accordance with the present embodiment, when it is determined in the second determination (step S60) that the value of resistance is greater than or equal to the predetermined value (NO in step S64), the control device 600 performs the control for crushing the gallstone G (step S90). With this control, it is possible to grasp, through the grasping of the value of resistance, that the gallstone G needs to be crushed to remove the gallstone G without applying a load to the vicinity of the papillary orifice.

Although not described in the flowchart, for example, processing of fetching the gallstone G in the basket 1430 may be added to the gallstone removal processing (step S20). For example, when performing the gallstone removal processing (step S20) using the second determination (step S60), the control device 600 may perform, before the second determination (step S60), first predetermined processing of performing advancing/retreating, opening/closing, rotation, or the like of the basket 1430 a predetermined number of times and second predetermined processing of causing the operator to confirm that the gallstone G has been fetched in the basket 1430. Note that the first predetermined processing is a known technique, and thus a description thereof is omitted.

The control device 600 performs the second determination (step S60), for example, when detecting a predetermined signal in the second predetermined processing. The predetermined signal is a signal that is output to the control device 600 in response to the operator's input operation to an operation input section, which is not illustrated, when the operator or the like determines that the gallstone G has been fetched in the basket 1430 through observation of the transmissive image. Note that the control device 600, when being unable to detect the predetermined signal in a certain period, may additionally perform control for performing the first predetermined processing again. Additionally, the second predetermined processing may be, for example, processing of the control device 600 to determine that the gallstone G has been fetched in the basket 1430 through image recognition of the transmissive image. For example, the control device 600 may perform the first predetermined processing and the second predetermined processing before the first determination (step S50).

Figure 15:
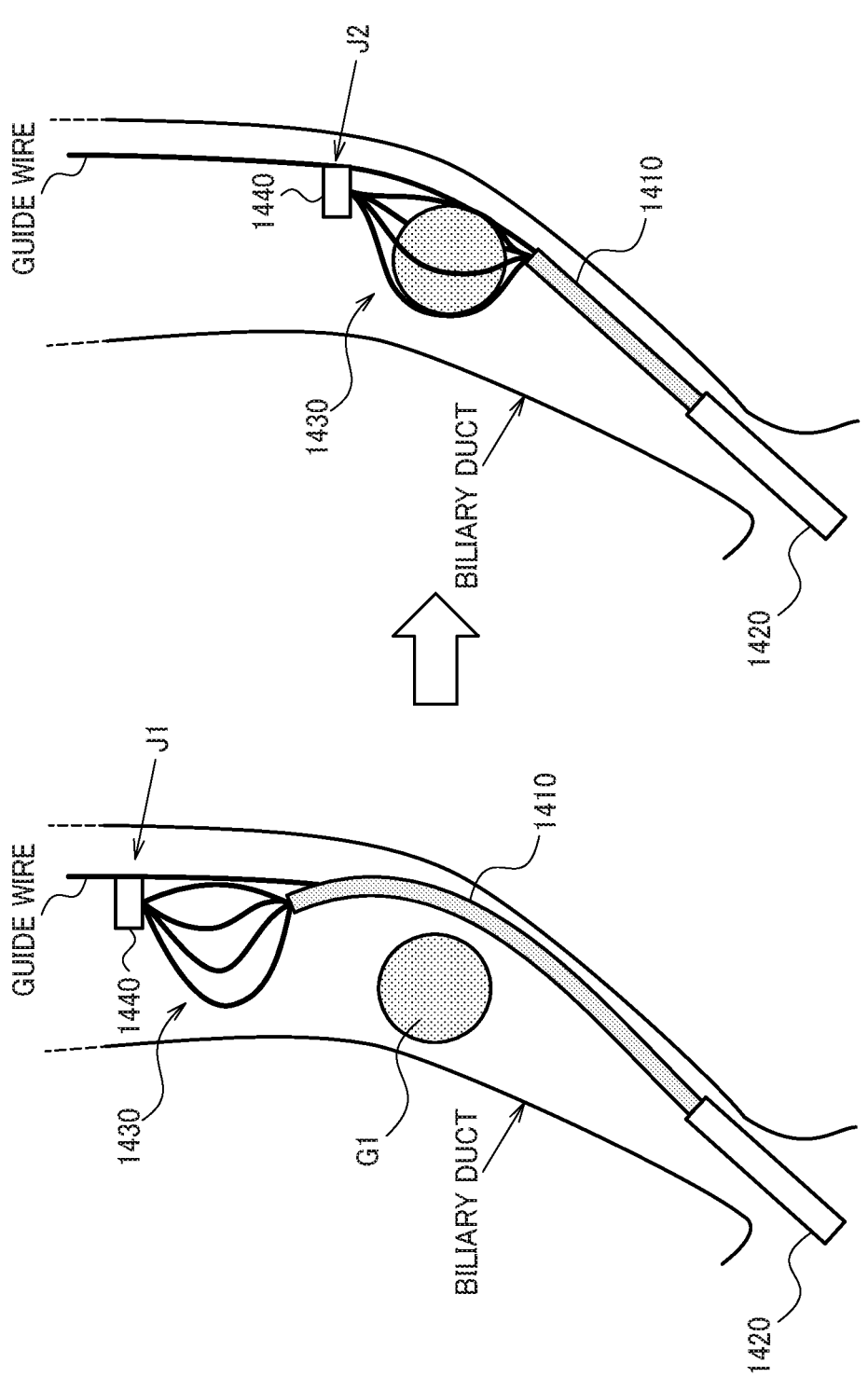
FIG. 15 is a diagram for describing control or the like of fetching a gallstone.
Figure 16:
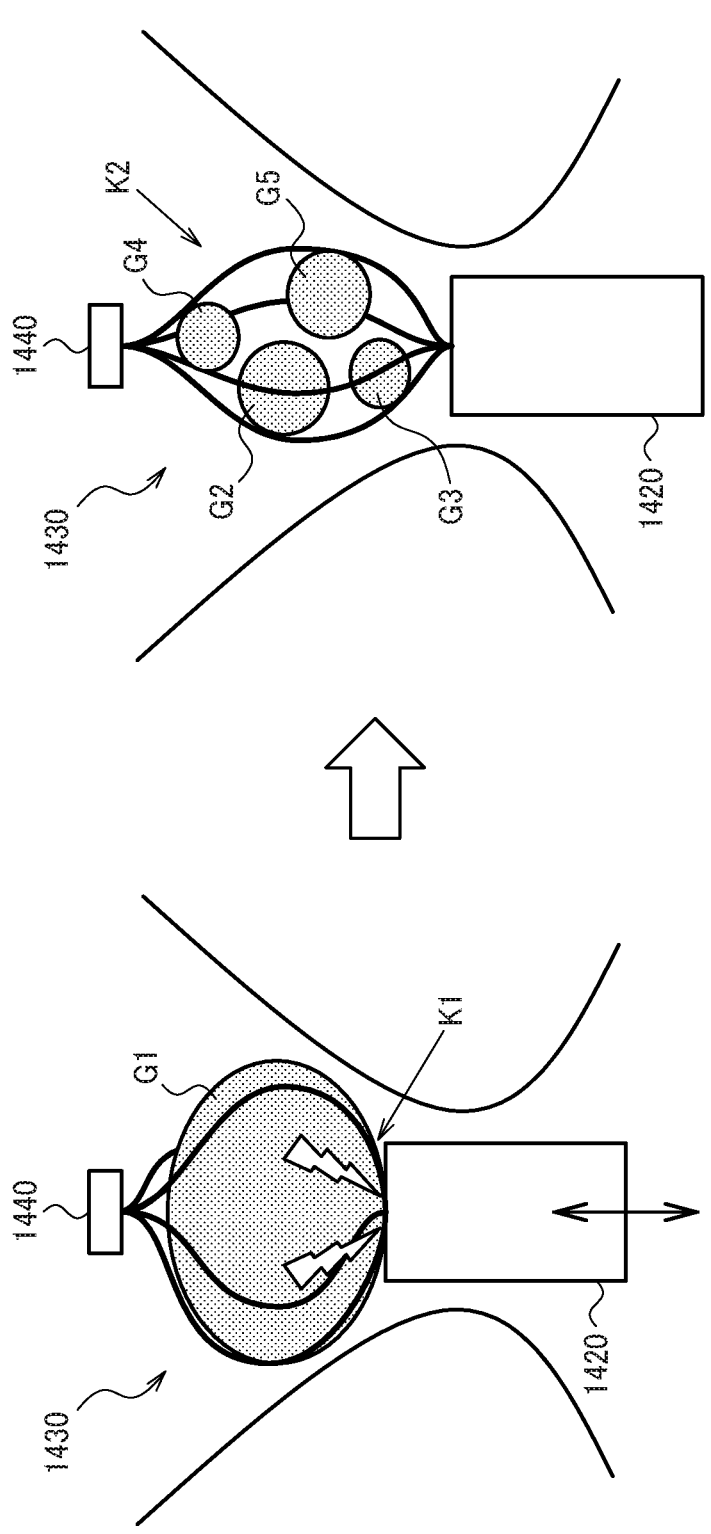
FIG. 16 is a diagram for describing stone crushing processing.

The second determination (step S60) and the stone crushing processing (step S90) are schematically exemplified with reference to FIGS. 15 and 16. Assume that operations in FIGS. 15 and 16 are performed as a processing example in which the first determination (step S50) and step S54 are omitted from the flowchart in FIG. 14. For example, the operator positions the tip of the first sheath 1410 of the basket treatment tool 1400 on the upstream side of the gallstone G in the biliary duct. Thereafter, the control device 600 starts the first predetermined processing. The control device 600 first projects the tip member 1440 from the first sheath 1410. With this operation, the tip member 1440 and the basket 1430 are positioned on the upstream side of a gallstone G1 as indicated, for example, in J1 in FIG. 15. Note that the guide wire passes through an inner cavity of the tip member 1440 in the basket treatment tool 1400 illustrated in FIG. 15. The inner cavity is not illustrated. This allows the tip member 1440 to rotate about the guide wire serving as a central axis.

Thereafter, the control device 600 advances/retreats the first sheath 1410 toward the base end side in accordance with a predetermined operation program. With this operation, the tip member 1440 moves to a downstream portion of the biliary duct along the guide wire as indicated in J2 in FIG. 15, and the gallstone G1 is fetched in the basket 1430. Note that the control device 600 may further perform advancing and retreating of the first sheath 1410 multiple times, additionally perform an opening/closing operation of the basket 1430, or additionally perform an operation of rotating the basket 1430 about the axis of the guide wire, and can perform an operation that is modified in various manners.

The operator then confirms a state where the gallstone G1 has been fetched in the basket 1430, and thereafter gives an instruction for performing the second determination (step S60) to the control device 600. The control device 600 then performs, for example, control for measuring resistance while electrically pulling the first sheath 1410 to the downstream side. In this manner, in the medical system 10 in accordance with the present embodiment, the control device 600 performs control for inserting the basket treatment tool 1400 into the biliary duct to a position at which the basket treatment tool 1400 catches the gallstone G before execution of the second determination (step S60). This operation enables appropriate execution of the second determination (step S60). This is because the value of resistance as a result of measurement in a state where the gallstone G has not been fetched is not always an appropriate value.

In a case where the value of resistance exceeds the predetermined value due to, for example, a large size of the gallstone G1 when the control device 600 pulls the first sheath 1410 to the vicinity of the papillary orifice, the control device 600 determines NO in step S64, and performs the stone crushing processing (step S90).

The control device 600, for example, advances the second sheath 1420 toward the upstream side in the stone crushing processing (step S90), and performs control for bringing the second sheath 1420 into contact with the gallstone G1. The second sheath 1420 is made of a hard material. Accordingly, the control device 600 thereafter repeatedly performs advancing/retreating of the second sheath 1420, and can thereby make an impact on the gallstone G1 as indicated, for example, in K1 in FIG. 16. As a result, the gallstone G1 is crushed into, for example, gallstones G2 to G5 as indicated, for example, in K2 in FIG. 16. Note that FIG. 16 is merely an example, and does not limit a manner of the stone crushing processing (step S90) to the manner of crushing one gallstone G1 into the four gallstones G2 to G5, or the like.

When the value of resistance is less than the predetermined value as a result of the second determination (step S60) performed again (YES in step S64), the whole of the basket treatment tool 1400 is pulled out from the biliary duct by the treatment tool pulling processing (step S80). With this operation, the crushed gallstones G2 to G5 are removed from the biliary duct without application of a load to the vicinity of the papillary orifice, and the gallstone removal processing (step S20) ends. For all these reasons, in the medical system 10 in accordance with the present embodiment, when it is determined in the second determination (step S60) that the value of resistance is less than the predetermined value (YES in step S64), the control device 600 performs control for removing the gallstone G (step S80). This control can prevent a load from being applied to the vicinity of the papillary orifice when the basket treatment tool 1400 is pulled to remove the gallstone G through grasping of the value of resistance.

Figure 17:
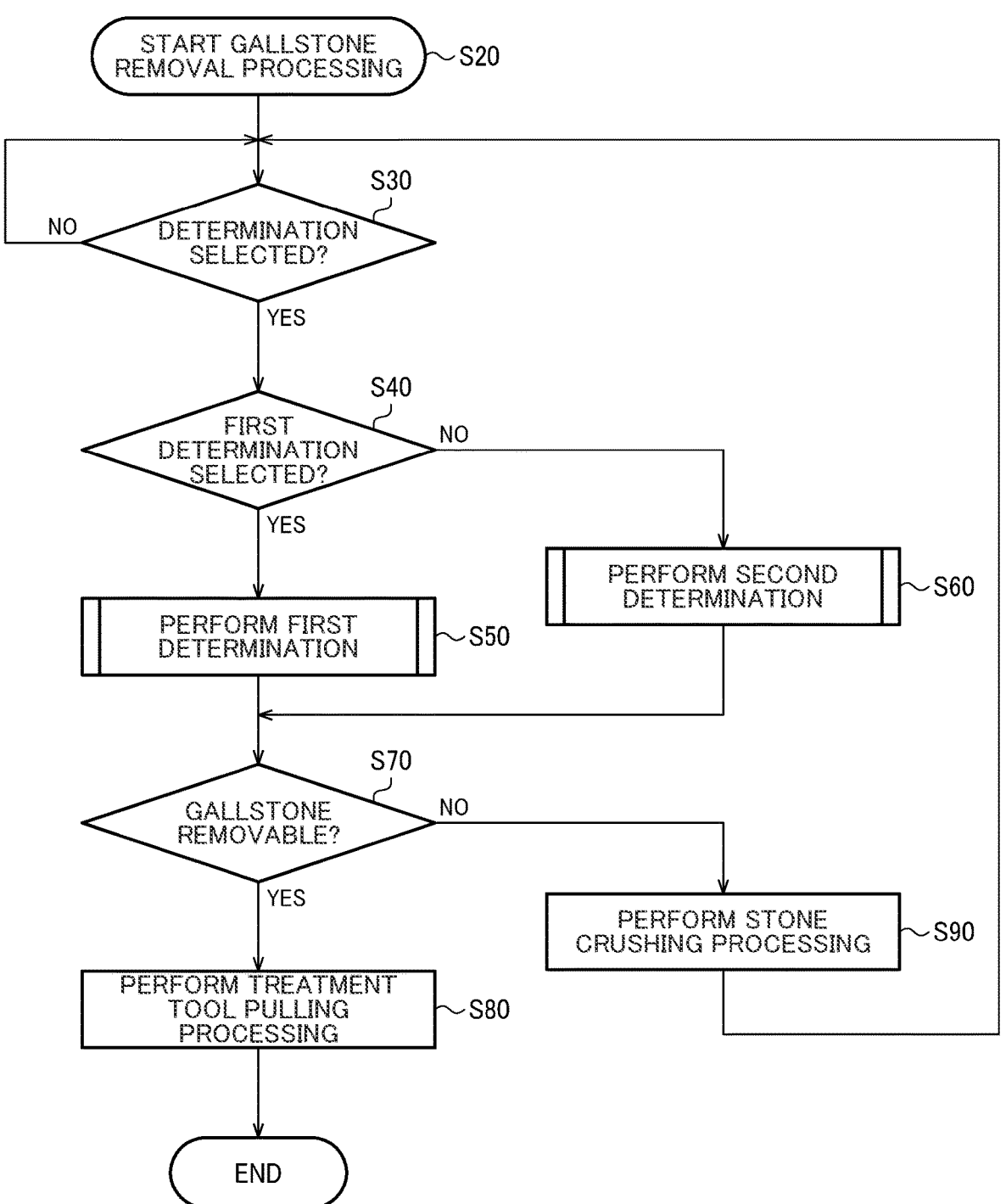
FIG. 17 is a flowchart describing another processing example of the gallstone removal processing.

Note that the stone crushing processing (step S90) can also be added to a modification of the gallstone removal processing (step S20) in FIG. 13. In other words, for example, a processing example in FIG. 13 may be implemented as a processing example indicated in FIG. 17. Note that in FIG. 17, a description of processing overlapping with that in FIG. 13 is omitted as appropriate. The processing example in FIG. 17 is different from that in FIG. 13 in control performed when it is determined that the gallstone G is not removable (NO in step S70). More specifically, when it is determined that the gallstone G is not removable (NO in step S70), the control device 600 performs the stone crushing processing (step S90).

The control device 600 then performs the above-mentioned stone crushing processing (step S90), and thereafter performs step S30 again. That is, the control device 600 performs, after completion of the stone crushing processing (step S90), processing of causing the operator to select the first determination (step S50) or the second determination (step S50) again. For example, the operator may repeatedly perform the first determination (step S50), or may select the second determination (step S60) after performing the first determination (step S50) and the stone crushing processing (step S90). Similarly, for example, the operator may repeatedly perform the second determination (step S60), or may select the first determination (step S50) after performing the second determination (step S60) and the stone crushing processing (step S90). Although not described in the flowchart, for example, the control device 600 may perform control for automatically determining a determination after execution of the stone crushing processing (step S90). As described above, in the medical system 10 in accordance with the present embodiment, the control device 600 performs the first determination (step S50) or the second determination (step S50) after performing control for crushing the gallstone G (step S90). This allows the operator to grasp whether the gallstone G is crushed appropriately.

Note that the method in accordance with the present embodiment is not limited to the above-mentioned method, and can be modified in various manners. For example, when detecting a predetermined abnormality, the control device 600 may further perform control for aborting the above-mentioned gallstone removal processing (step S20).

The predetermined abnormality is, for example, an abnormality regarding vibrations. For example, an acceleration sensor or the like is arranged at a predetermined location of the basket treatment tool 1400, and is connected to the control device 600 through the basket driving device 1200 and the drive control device 200. The predetermined location is, for example, the tip member 1440, but may be the coupling member 1442 or the like. When detecting vibrations exceeding a range that is normally detected by the acceleration sensor due to a predetermined cause at the time of execution of the gallstone removal processing (step S20), the control device 600 performs control for aborting the gallstone removal processing (step S20). The predetermined cause is a disaster such as an earthquake, but may be, for example, an impact erroneously made by the operator or the like on any of constituent elements of the endoscope 100 or the like.

Alternatively, for example, the control device 600 may detect the abnormality regarding vibrations based on a captured image. For example, assume that a cholangioscope is inserted into the papillary orifice, the basket treatment tool 1400 is included in the cholangioscope, and the gallstone removal processing (step S20) is thereby executed. When video images captured by the cholangioscope are disturbed by the cholangioscope, the control device 600 may perform control for aborting the gallstone removal processing (step S20).

Alternatively, the predetermined abnormality may be an abnormality regarding the shape of the basket 1430. For example, the control device 600 periodically captures an image of the shape of the basket 1430 in the contrast-enhancement processing (step S10), and performs processing of determining whether the shape of the basket 1430 is abnormal. More specifically, for example, a plurality of model images regarding possible shapes of the basket 1430 is preliminarily stored in a predetermined memory. After the start of treatment using the basket treatment tool 1400, the control device 600 performs processing of extracting a portion corresponding to the basket 1430 from the transmissive image captured in the contrast-enhancement processing (step S10) and processing of comparing an image of the portion corresponding to the basket 1430 and the stored model images. When it is determined that the image of the basket 1430 in the captured transmissive image is not common to any of the model images, the control device 600 determines that the shape of the basket 1430 is abnormal, and performs control for aborting the gallstone removal processing (step S20).

Note that after performing control for aborting the gallstone removal processing (step S20), the control device 600 may perform, for example, such control as to enable a manual operation of the endoscope 100, the treatment tool 400, or the like constituting the medical system 10.

Alternatively, for example, the control device 600 may change the predetermined speed in the second determination (step S60) in accordance with a position of the basket 1430 in the biliary duct. The position of the basket 1430 in the biliary duct can be estimated by a predetermined method. The predetermined method is, for example, a method of estimating the position from the captured image or the like, and a method of estimating the position based on the number of steps or the like of a motor used for an operation of pushing the first sheath 1410 or the operation wire 1444. For example, when it is determined that the basket 1430 is at a position away from a position of the papillary orifice by a predetermined distance on the upstream side, the control device 600 performs control for pulling the basket treatment tool 1400 toward the base end side at a first speed. Thereafter, when it is determined that a distance between the position of the basket 1430 and the position of the papillary orifice is less than the predetermined distance, the control device 600 performs control for pulling the basket treatment tool 1400 toward the base end side at a second speed that is lower than the first speed.

Note that the method regarding change of the predetermined speed is not limited to the above-mentioned methods. For example, when the basket treatment tool 1400 is positioned in the vicinity of the papillary orifice, the control device 600 may further perform control for pulling the basket treatment tool 1400 at a third speed that is lower than the second speed. This can prevent an excessive load from being applied to the vicinity of the papillary orifice.

For example, when the value of resistance is less than a first predetermined value in the second determination (step S60), or when the basket treatment tool 1400 is pulled toward the base end side at the first speed and the value of resistance is greater than a first resistance value, the control device 600 may perform control for pulling the basket treatment tool 1400 toward the base end side at the second speed.

Alternatively, part or the whole of the above-mentioned method regarding change of the predetermined speed may be applied to the treatment tool pulling processing (step S80).

Figure 18:
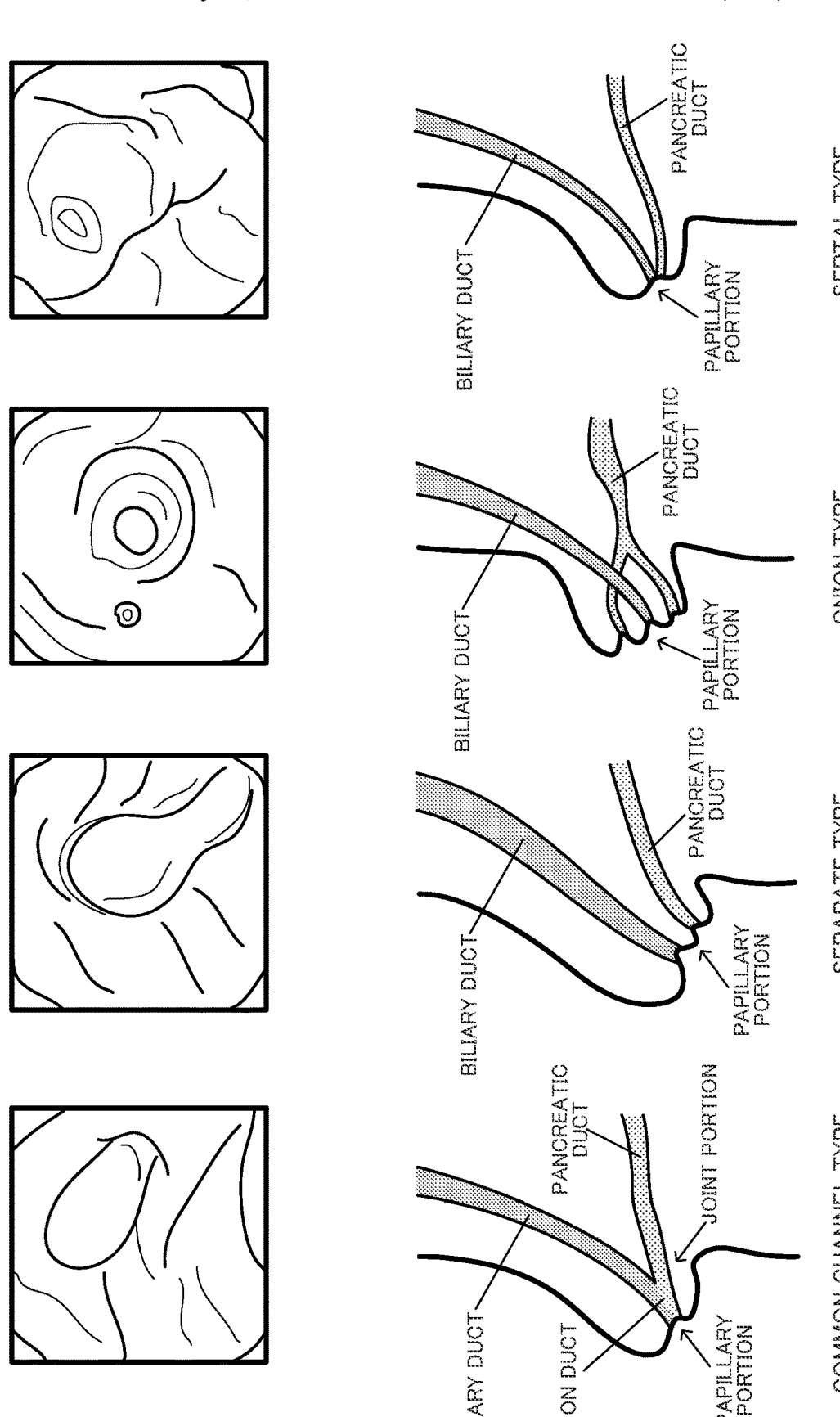
FIG. 18 is a diagram for describing an endoscope image of the papillary portion and a corresponding type of the biliary duct and the pancreatic duct.

Still alternatively, for example, the control device 600 may perform control for estimating a path structure of the biliary duct and the pancreatic duct from the endoscope image of the papillary portion, and determining the predetermined criterion size used for the first determination criterion for the first determination (step S50) based on the estimated structure. For example, there are unique structures called a frenum, a papillary protrusion, an encircling fold, a circular fold, and an oral protrusion in the periphery of the papillary orifice. There is a certain correlation between a combination of these structures and the path structure of the biliary duct and the pancreatic duct, and it is empirically known that the correlation can be classified into some patterns. For example, as illustrated in FIG. 18, as a type of the endoscope image and the path structure of the biliary duct and the pancreatic duct estimated from the endoscope image, there are a common channel type, a separate type, an onion type, and a septal type. Note that types of the path structure of the biliary duct and the pancreatic duct are not limited to those illustrated in FIG. 18.

For example, when estimating that the type of the path structure of the biliary duct and the pancreatic duct is the common channel type based on the captured endoscope image, the control device 600 then performs, for example, control for setting the predetermined criterion size as a first criterion size because there is the joint portion in which the biliary duct and the pancreatic duct join together. In contrast, when estimating that the type of the path structure of the biliary duct and the pancreatic duct is a type other than the common channel type based on the captured endoscope image, the control device 600 then performs, for example, control for setting the predetermined criterion size as a second criterion size that is smaller than the first criterion size because there is no joint portion and the vicinity of the papillary orifice is narrower than that of the common channel type. With this control, the control device 600 can more appropriately set a criterion as to whether the gallstone G is removable in accordance with the path structure of the biliary duct and the pancreatic duct as the first determination criterion in the first determination (step S50).

As described above, the operation of the basket treatment tool 1400 can be an electrically driven operation, and the specification of United States Patent Application Publication No. 2007/0185377 discloses the example of advancing/retreating and opening/closing the basket forceps in accordance with the embedded program. However, when the size of the gallstone is large, it is difficult to pull the basket treatment tool 1400 and remove the gallstone G from the papillary orifice. If each of advancing/retreating, opening/closing, and removal is automatically performed by the embedded program in a mechanical manner, there is a possibility for applying a load to the vicinity of the papillary orifice, and a possibility for failure to remove the gallstone G completely. Addition of treatment for enlarging the vicinity of the papillary orifice complicates the manipulation, and increases a burden on the operator. This increases a burden on the patient. It is difficult for the operator to accurately determine whether the size of the gallstone G fetched in the basket 1430 is a size that allows the gallstone G to easily pass through the papillary orifice.

The medical system 10 in accordance with the present embodiment includes the basket treatment tool 1400 and the control device 600. The basket treatment tool 1400 is inserted into the biliary duct from the papillary orifice and capable of performing driving for opening/closing and advancing/retreating. The control device 600 controls the driving of the basket treatment tool 1400. The control device 600 performs the first determination (step S50) or the second determination (step S60). The first determination (step S50) is to determine, based on the transmissive image including the biliary duct, whether the size of the gallstone G allows the basket treatment tool 1400 to remove the gallstone G from the papillary orifice. The second determination (step S60) is to determine, based on resistance when the basket treatment tool 1400 is pulled, whether the resistance allows the basket treatment tool 1400 to remove the gallstone G from the papillary orifice. When it is determined in the first determination (step S50) or the second determination (step S60) that the gallstone G is removable from the papillary orifice (YES in step S54 or YES in step S64), the control device 600 performs control for removing the gallstone G from the papillary orifice using the basket treatment tool 1400 (step S80).

The present embodiment enables structuring of the medical system 10 capable of determining whether the size of the gallstone G fetched in the basket treatment tool 1400 enables removal of the gallstone G from the papillary orifice. In addition, control for removing the gallstone G from the papillary orifice using the basket treatment tool 1400 is performed only when it is determined that the size of the gallstone G fetched in the basket treatment tool 1400 enables removal of the gallstone G from the papillary orifice, whereby it is possible to perform safe treatment on the patient.

Note that the basket treatment tool 1400 has been described with reference to FIG. 7 and the like. The papillary portion and the biliary duct have been described with reference to FIG. 1 and the like. The first determination (step S50) has been described with reference to FIG. 10 and the like. The second determination (step S60) has been described with reference to FIG. 12 and the like.

Additionally, in the present embodiment, when it is determined in the first determination (step S50) or the second determination (step S60) that the gallstone G is not removable from the papillary orifice (NO in step S54 or NO in step S64), the control device 600 may perform control for crushing the gallstone (step S90).

The present embodiment enables reduction of the size of the gallstone G that is difficult to be removed from the papillary orifice.

Note that the control for crushing the gallstone G has been described with reference to FIG. 14 and the like.

In the present embodiment, the control device 600 may perform control for crushing the gallstone G using the basket treatment tool 1400 (step S90).

The present embodiment can simplify the configuration of the treatment tool for crushing the gallstone G.

Note that the control for crushing the gallstone G using the basket treatment tool 1400 has been described with reference to FIG. 15 and the like.

Additionally, in the present embodiment, the control device 600 may perform the first determination (step S50) or the second determination (step S60) after performing control for crushing the gallstone G (step S90).

The present embodiment allows the operator to grasp whether the gallstone G is crushed appropriately.

Note that the control for performing the first determination (step S50) or the second determination (step S60) after performing the control for crushing the gallstone G (step S90) has been described with reference to FIG. 14 and the like.

Additionally, in the present embodiment, the control device 600 may perform the first determination (step S50) based on the transmissive image, and, when it is determined in the first determination (step S50) that the size of the gallstone G is smaller than or equal to the predetermined criterion size, may perform the second determination (step S60).

The present embodiment enables more appropriate determination as to whether the gallstone G is removable.

Note that the control for performing the second determination (step S60) after performing the first determination (step S50) has been described with reference to FIG. 9 and the like.

Additionally, in the present embodiment, when it is determined in the first determination (step S50) that the size of the gallstone G is larger than the predetermined criterion size (NO in step S54), the control device 600 may perform control for crushing the gallstone G (step S90).

The present embodiment enables grasping of, through the transmissive image, the necessity for crushing of the gallstone G to remove the gallstone G without applying a load to the vicinity of the papillary orifice.

Note that the control for crushing the gallstone G when it is determined in the first determination (step S50) that the size of the gallstone G is larger than the predetermined criterion size has been described with reference to FIG. 14 and the like.

In the present embodiment, when it is determined in the second determination (step S60) that the value of resistance is greater than or equal to the predetermined value (NO in step S64), the control device 600 may perform control for crushing the gallstone G (step S90).

The present embodiment enables grasping of, through the measurement of resistance, the necessity for crushing of the gallstone G to remove the gallstone G without applying a load to the vicinity of the papillary orifice.

Note that the control for crushing the gallstone G (step S90) when it is determined in the second determination (step S60) that the value of resistance is greater than or equal to the predetermined value has been described with reference to FIG. 14 and the like.

In the present embodiment, when it is determined in the second determination (step S60) that the value of resistance is less than the predetermined value (YES in step S64), the control device 600 may perform control for removing the gallstone G (step S80).

The present embodiment can prevent a load from being applied to the vicinity of the papillary orifice when the basket treatment tool 1400 is pulled to remove the gallstone G.

Note that the control for removing the gallstone G when it is determined in the second determination (step S60) that the value of resistance is less than the predetermined value has been described with reference to FIG. 14 and the like.

Additionally, in the present embodiment, the control device 600 may perform control for inserting the basket treatment tool 1400 into the biliary duct to a position at which the basket treatment tool catches the gallstone G before execution of the second determination (step S60).

In accordance with the present embodiment, such control enables appropriate execution of the second determination (step S60).

Note that the control for inserting the basket treatment tool 1400 into the biliary duct to the position at which the basket treatment tool 1400 catches the gallstone G before execution of the second determination has been described with reference to FIG. 15 and the like.

In accordance with the present embodiment, the control device 600 may control the driving of the basket treatment tool 1400 by means of electric driving.

The present embodiment enables structuring of the medical system 10 that electrically drives the basket treatment tool 1400.

Note that the control for electrically driving the basket treatment tool 1400 has been described with reference to FIG. 7 and the like.

In the present embodiment, the transmissive image may be the ERCP image or the MRCP image.

The present embodiment enables structuring of the medical system 10 using the ERCP image or the MRCP image.

Note that the transmissive image has been described with reference to FIG. 2 and the like.

Additionally, the present embodiment may be implemented as the operation method for the medical system 10 as follows. That is, the operation method for the medical system 10 includes the step of causing the basket treatment tool 1400 to perform driving for opening/closing and advancing/retreating. The basket treatment tool 1400 is inserted into the biliary duct from the papillary orifice and capable of performing driving for opening/closing and advancing/retreating. The operation method for the medical system 10 includes the step of performing the first determination or the second determination (step S50 or step S60). The first determination (step S50) is to determine, based on the transmissive image including the biliary duct, whether the size of the gallstone G allows the basket treatment tool 1400 to remove the gallstone G from the papillary orifice. The second determination (step S60) is to determine, based on resistance when the basket treatment tool 1400 is pulled, whether the resistance allows the basket treatment tool 1400 to remove the gallstone G from the papillary orifice. The operation method for the medical system 10 includes the step of, when it is determined in the first determination (step S50) or the second determination (step S60) that the gallstone is removable from the papillary orifice (YES in step S54 or YES in step S64), performing control for removing the gallstone G from the papillary orifice using the basket treatment tool 1400 (step S80). Note that in the operation method for the medical system 10, the medical system 10 plays a main role in performing each step.

Additionally, the present embodiment may be implemented as the non-transitory storage medium as follows. That is, the non-transitory information storage medium stores the program that causes the computer to execute the step of causing the basket treatment tool 1400 to perform driving for opening/closing and advancing/retreating. The basket treatment tool 1400 is inserted into the biliary duct from the papillary orifice and capable of performing driving for opening/closing and advancing/retreating. The non-transitory information storage medium stores the program that causes the computer to execute the first determination or the second determination (step S50 or step S60). The first determination (step S50) is to determine, based on the transmissive image including the biliary duct, whether the size of the gallstone G allows the basket treatment tool 1400 to remove the gallstone G from the papillary orifice. The second determination (step S60) is to determine, based on resistance when the basket treatment tool 1400 is pulled, whether the resistance allows the basket treatment tool 1400 to remove the gallstone G from the papillary orifice. When it is determined in the first determination (step S50) or the second determination (step S60) that the gallstone G is removable from the papillary orifice (YES in step S54 or YES in step S64), the non-transitory information storage medium stores the program that causes the computer to execute the step of performing control for removing the gallstone G from the papillary orifice using the basket treatment tool 1400 (step S80). Note that the medical system 10 plays a main role in performing each step of the programs stored in the non-transitory information storage medium.

Although the embodiments to which the present disclosure is applied and the modifications thereof have been described in detail above, the present disclosure is not limited to the embodiments and the modifications thereof, and various modifications and variations in components may be made in implementation without departing from the spirit and scope of the present disclosure. The plurality of elements disclosed in the embodiments and the modifications described above may be combined as appropriate to implement the present disclosure in various ways. For example, some of all the elements described in the embodiments and the modifications may be deleted. Furthermore, elements in different embodiments and modifications may be combined as appropriate. Thus, various modifications and applications can be made without departing from the spirit and scope of the present disclosure. Any term cited with a different term having a broader meaning or the same meaning at least once in the specification and the drawings can be replaced by the different term in any place in the specification and the drawings.

Known is a medical system that remotely performs electric control of a main body of an endoscope inserted into a body cavity and various types of treatment tools each inserted through a forceps channel. The specification of United States Patent Application Publication No. 2007/0185377 discloses a method of advancing/retreating and opening/closing a basket forceps in accordance with an embedded program.

In accordance with one of some aspect, there is provided a medical system comprising:

an endoscope with a tip portion from which a treatment tool is projectable; and a control device, the control device being configured to perform:

acquiring a body cavity image in which a body cavity including an object of treatment of the treatment tool is captured;

identifying, from the body cavity image, at least one of body cavity shape information indicating a shape of the body cavity or position information indicating a position of the object of the treatment in the body cavity as identification information; and controlling a projection position of the treatment tool from the tip portion of the endoscope based on the identification information.

In accordance with one of some aspect, there is provided a treatment tool control method of controlling a treatment tool projectable from a tip portion of an endoscope, the method comprising:

acquiring a body cavity image in which a body cavity including an object of treatment of the treatment tool is captured;

identifying, from the body cavity image, at least one of body cavity shape information indicating a shape of the body cavity or position information indicating a position of the object of the treatment in the body cavity as identification information; and controlling a projection position of the treatment tool from the tip portion of the endoscope based on the identification information.

In accordance with one of some aspect, there is provided a non-transitory information storage medium that stores a program that causes a computer to execute steps comprising:

acquiring a body cavity image in which a body cavity including an object of treatment of a treatment tool is captured, the treatment tool being projectable from a tip portion of an endoscope;

identifying, from the body cavity image, at least one of body cavity shape information indicating a shape of the body cavity or position information indicating a position of the object of the treatment in the body cavity as identification information; and controlling a projection position of the treatment tool from the tip portion of the endoscope based on the identification information.

The following disclosure provides many different embodiments, or examples, for implementing different features of the provided subject matter. These are, of course, merely examples and are not intended to be limiting. In addition, the disclosure may repeat reference numerals and/or letters in the various examples. This repetition is for the purpose of simplicity and clarity and does not in itself dictate a relationship between the various embodiments and/or configurations discussed. Further, when a first element is described as being "connected" or "coupled" to a second element, such description includes embodiments in which the first and second elements are directly connected or coupled to each other, and also includes embodiments in which the first and second elements are indirectly connected or coupled to each other with one or more other intervening elements in between.

1. Basket Treatment Tool

The present embodiment is directed to automatic control of an electrically driven basket treatment tool based on an image to assist treatment. First, a configuration example of an electrically driven basket treatment tool 3400 is described with reference to FIG. 19.

Figure 19:
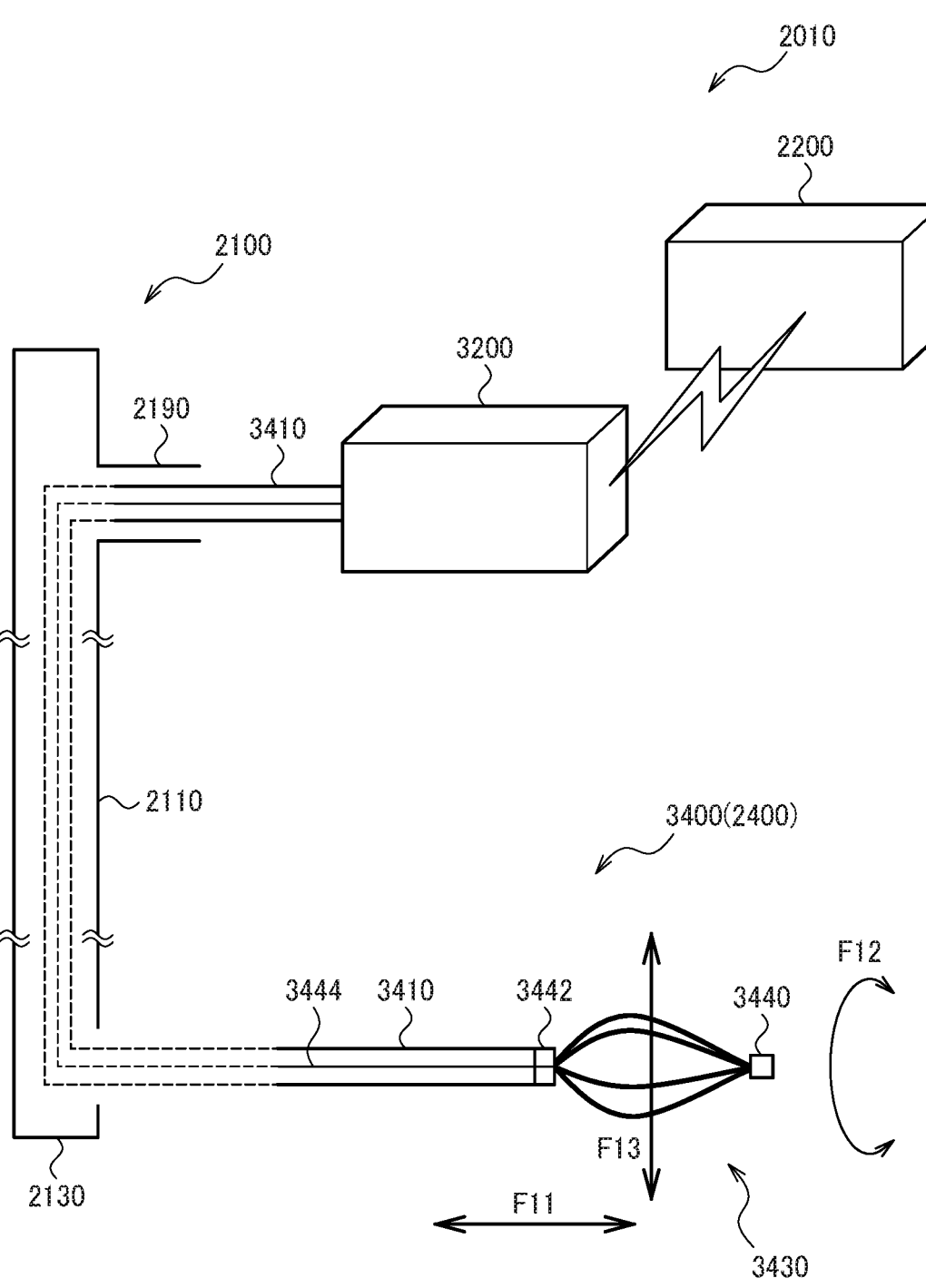
FIG. 19 illustrates a configuration example of an electrically driven basket treatment tool.

FIG. 19 illustrates an overview of a medical system 2010 including the basket treatment tool 3400 and the configuration example of the basket treatment tool 3400. The medical system 2010 includes an endoscope 2100, a drive control device 2200, a basket driving device 3200, and the basket treatment tool 3400. Note that the basket treatment tool 3400 corresponds to a treatment tool 2400 in a detailed configuration example of the medical system 2010, which will be described later with reference to FIG. 30 and the like. Details of the endoscope 2100 and the drive control device 2200, the flow of manipulation using endoscopic retrograde cholangiopancreatography (ERCP), to which the medical system 2010 is applied, and the like will be described later.

Figure 25:
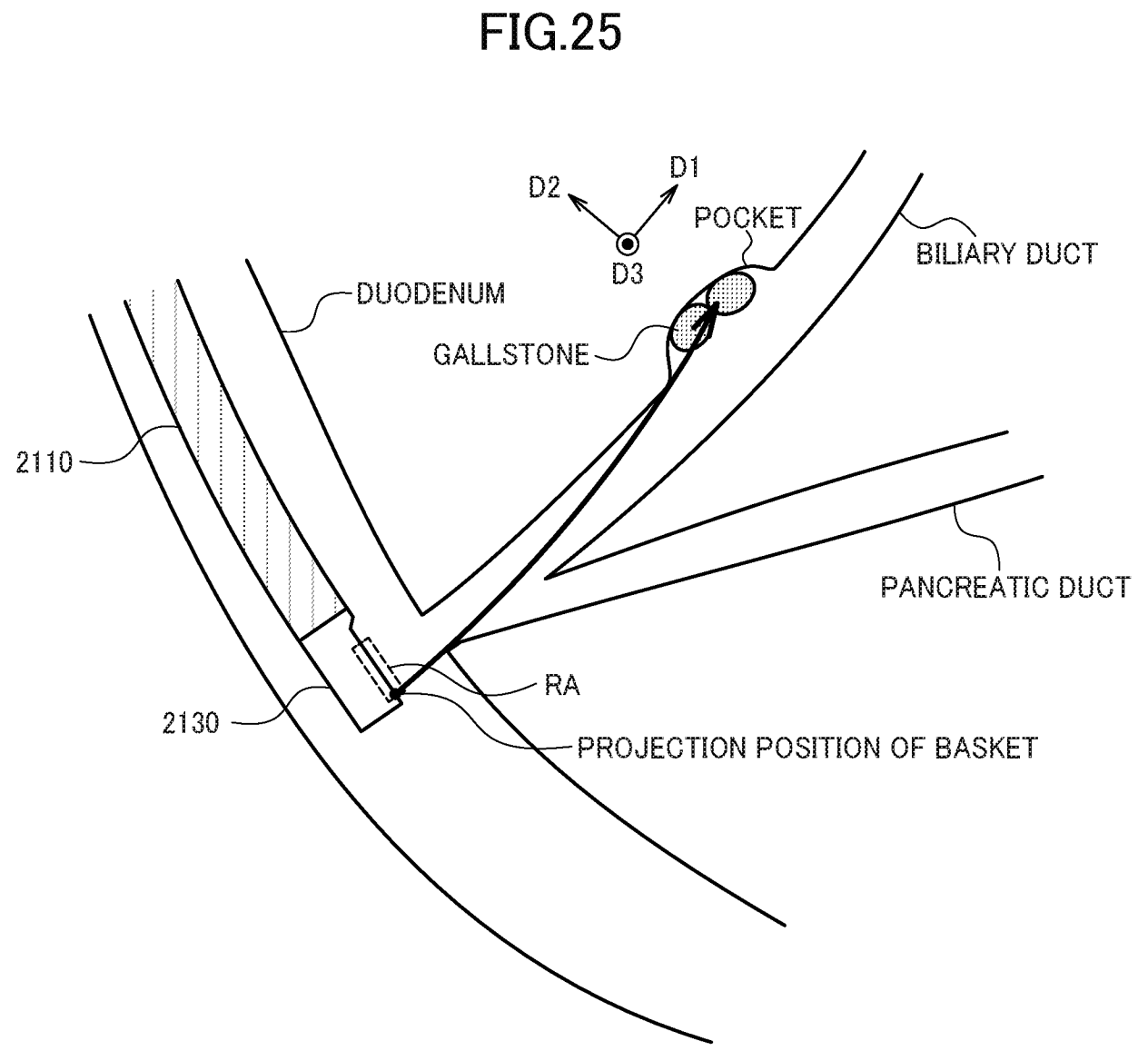

Note that in the endoscope 2100 in FIG. 19, a configuration other than an insertion opening 2190, an insertion portion 2110, and a tip portion 2130 is not illustrated. The endoscope 2100 in FIG. 25 is illustrated for conceptually indicating the insertion opening 2190, the insertion portion 2110, and the tip portion 2130, and does not limit a structure or the like of the endoscope 2100 in any way. For example, FIG. 19 illustrates that a rising angle of the treatment tool 2400 serving as the basket treatment tool 3400 is 90 degrees, but this does not limit the rising angle of the treatment tool 2400 in accordance with the present embodiment to 90 degrees.

The basket treatment tool 3400 includes, for example, a first sheath 3410, a basket 3430, and an operation wire 3444, and is electrically driven by the basket driving device 3200. Note that the basket treatment tool 3400 may be configured to, for example, include a plurality of sheathes, and details thereof will be described later. For example, a basket treatment tool 3400 for a purpose of extraction of a stone and a basket treatment tool 3400 for a purpose of crushing of a stone may be configured to be used differently, and the respective basket treatment tools 3400 may be projectable from the tip portion 2130.

The basket treatment tool 3400, which will be described later, may be manually operable in a predetermined case.

The predetermined case is a case where an unexpected malfunction occurs in the basket driving device 3200 or other cases.

The basket driving device 3200 includes an operation wire driving section for advancing/retreating an operation wire 3444. A tip of the operation wire 3444 is connected to a base end of the basket 3430, and the operation wire driving section advances/retreats the base end side of the operation wire 3444, whereby the basket 3430 is projected from the first sheath 3410 or is accommodated in the first sheath 3410. The operation wire driving section includes, for example, a mechanism such as a motor and a rack-and-pinion. This enables a configuration of a slide mechanism for advancing/retreating the operation wire 3444 or the like using rotative force of the motor.

The basket driving device 3200 may include a sheath driving section for advancing/retreating the first sheath 3410 in a direction indicated in F11. The sheath driving section advances/retreats the first sheath 3410, whereby the first sheath 3410 and the basket 3430 advances/retreats in the biliary duct or the like. The sheath driving section includes, for example, a mechanism such as a motor and a rack-and-pinion similarly to the operation wire driving section.

In addition, an operation input section with which an operator can operate the basket treatment tool 3400 may be connected to the drive control device 2200 through wired or wireless communication. The operation input section includes, for example, a dial, a joy stick, an arrow key, a button, and a switch, a touch panel, and/or the like. This allows, for example, the operator to advance/retreat the operation wire 3444 at a predetermined distance. The operation input section of the basket treatment tool 3400 may be integrated with an operation device 2300 in FIG. 31, which will be described later, or may be configured as another controller aside from the operation device 2300. The operation input section of the basket treatment tool 3400 may be arranged in the basket driving device 3200.

Figure 32:
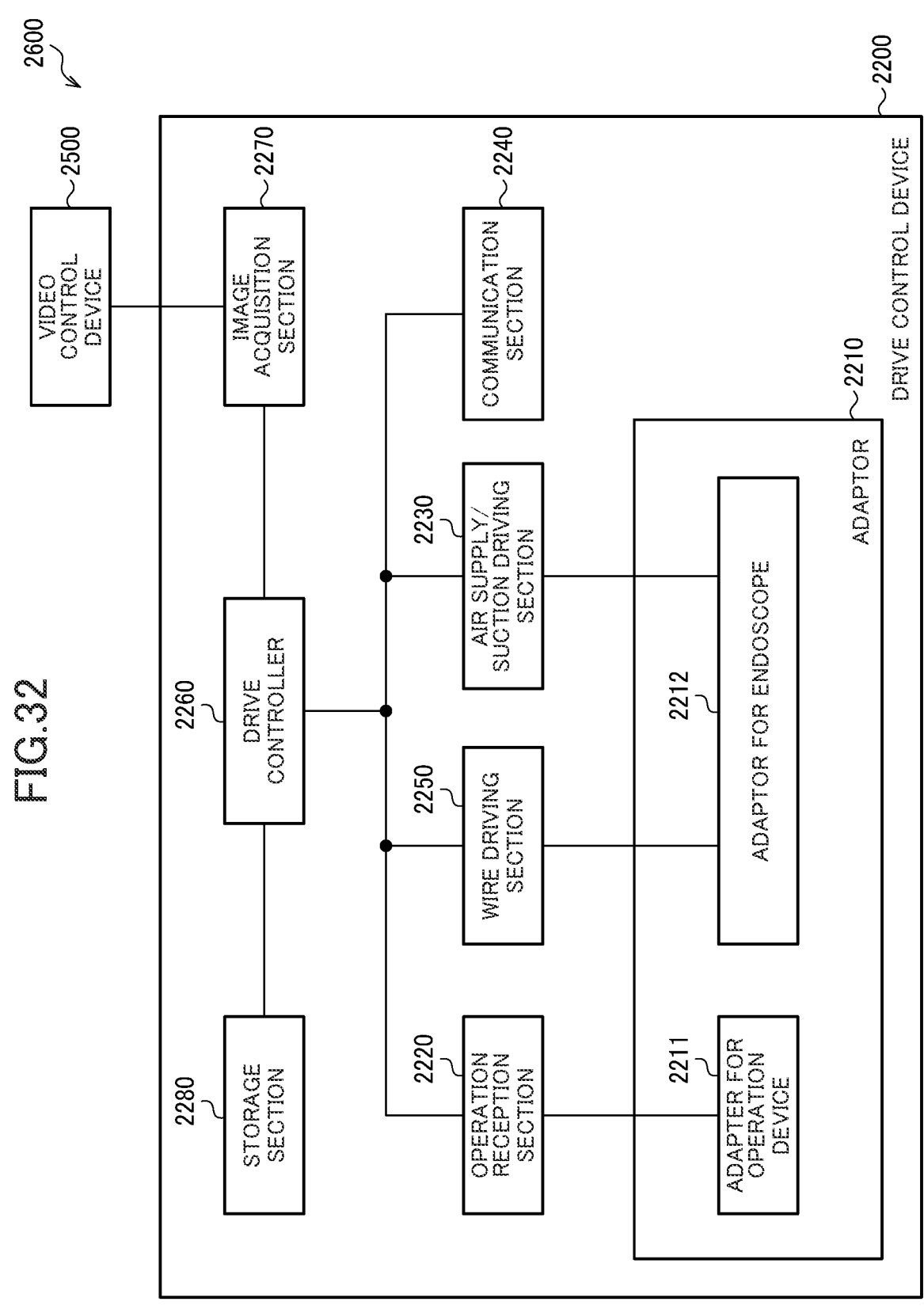
FIG. 32 is a block diagram illustrating a detailed configuration example of a drive control device.

The basket driving device 3200 has a wireless communication connection with the drive control device 2200 through a communication section 2240 illustrated in FIG. 32. The drive control device 2200 controls an operation of the basket driving device 3200 through the communication connection. The drive control device 2200 automatically controls crushing or pulling of a gallstone by the basket treatment tool 3400 or controls an operation of the basket driving device 3200 based on an operation from the operator using the above-mentioned operation input section. Note that the basket driving device 3200 may have a wired communication connection with the drive control device 2200.

The basket 3430 includes a plurality of elastic wires. The elastic wires on the tip side are tied together by a tip member 3440, and the elastic wires on the base end side are tied together by a coupling member 3442. The number of elastic wires is not limited to four, and is determined as appropriate. For example, the number of elastic wires of the basket treatment tool 3400 for the purpose of extraction of the stone can be made larger than the number of elastic wires of the basket treatment tool 3400 for the purpose of crushing of the stone.

The elastic wires of the basket 3430 are self-urged so as to be bending outward in substantially identical shapes. In addition, the elastic wires are arranged at equal angular intervals when viewed from a direction from the tip member 3440 toward the first sheath 3410. With this configuration, the basket 3430 is formed in a contracted state while being pulled into the first sheath 3410, and is formed in a substantially basket shape in a state of projecting from the first sheath 3410.

The coupling member 3442 is arranged at the tip of the operation wire 3444. For example, the operator inserts the first sheath 3410 into the biliary duct at a desired position through the tip portion 2130 in a state where the basket 3430 is pulled into the first sheath 3410. The operator then performs an operation of pushing the operation wire 3444 toward the tip side. With this operation, the basket 3430 is projected from the first sheath, and the basket 3430 is formed in the substantially basket shape.

Note that the basket 3430 is illustrated in FIG. 19 in a substantially basket shape formed of bending lines, but the shape is not limited thereto. The basket 3430 may be, for example, in a substantially basket shape formed of folding points and straight lines. Various shapes have been proposed as publicly known shapes. Note that in the present embodiment, the shape of the basket 3430 is assumed to be optimized for extraction or the like of a gallstone.

Note that the basket driving device 3200 may further include a mechanism of, after projection of the basket 3430 from the first sheath 3410, further contracting the substantially basket shape and expanding the basket 3430 again. For example, sliding the operation wire 3444 toward the base end side and partially fetching the coupling member 3442 and part of the basket 3430 in the inside of the first sheath 3410 enables contraction/expansion of the basket 3430 in a direction indicated in F13.

In addition, the basket driving device 3200 may be provided with, for example, a mechanism for rotating the coupling member 3442 and the operation wire 3444 about an axis of the guide wire. For example. the tip member 3440 is inserted through the guide wire, which is not illustrated in FIG. 19, and a handle or the like that rotates the operation wire 3444 about the guide wire is arranged, whereby the basket 3430 can be rotated in a direction indicated in F12. This configuration facilitates fetching of a gallstone in the basket 3430.

Additionally, the basket treatment tool 3400 in accordance with the present embodiment may couple part of the plurality of elastic wires to a rotary shaft of the coupling member 3442. The rotary shaft is not illustrated. With this configuration, for example, rotating the operation wire 3444 temporarily changes the shape of the basket 3430, and can facilitate fetching of the gallstone.

Figure 31:
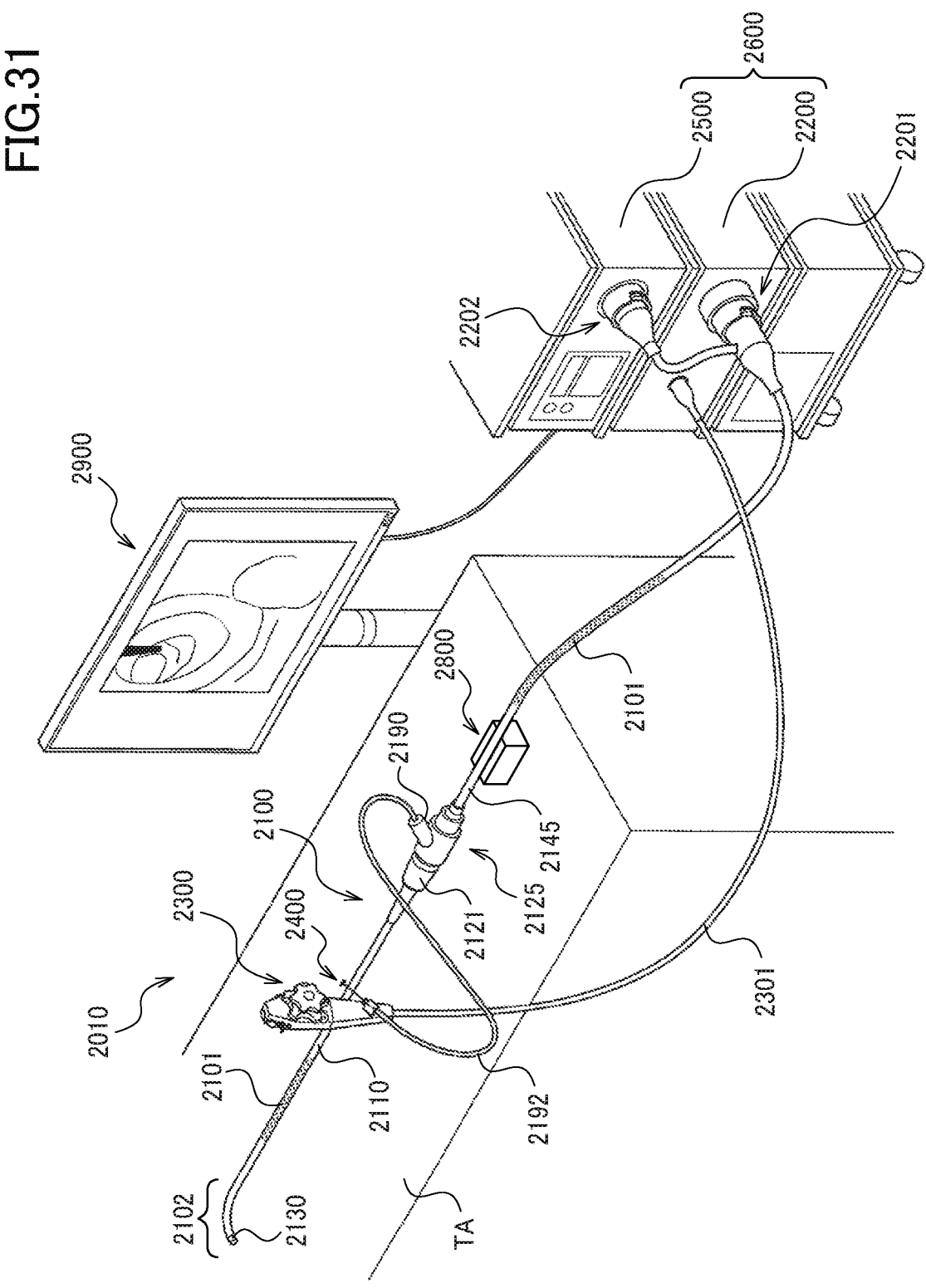
FIG. 31 illustrates a more detailed configuration example of the medical system.

For example, the operator uses the basket driving device 3200 to perform advancing/retreating, opening/closing, rotation, or the like of the basket 3430 until the gallstone is fetched in the basket 3430, while observing an endoscope image or a transmissive image displayed on a display device 2900 illustrated in FIG. 31. After the gallstone is fetched in the basket 3430, the operator uses the basket driving device 3200 to perform an operation of pulling out the basket treatment tool 3400 from the biliary duct, and can thereby remove the gallstone from the papillary orifice.

The operation of the basket treatment tool 3400 is not limited to a manual operation. That is, the drive control device 2200 may control the electrically driven basket driving device 3200 to automate the operation of the basket treatment tool 3400. For example, the drive control device 2200 may advance/retreat and open/close the basket 3430 in accordance with an embedded program to remove the gallstone from the biliary duct to the duodenum. Note that a connection between the drive control device 2200 and the basket driving device 3200 is not limited to a wireless connection, but may be a wired connection.

In addition, part of functions of the basket driving device 3200 may be integrated with those of the drive control device 2200. For example, a wire driving section 2250 in FIG. 32 may be capable of controlling drive of the operation wire 3444 of the basket treatment tool 3400. Similarly, a function as the operation input section of the basket driving device 3200 may be implemented by the operation device 2300 in FIG. 31.

2. Method of Controlling Insertion Direction and Projection Position of Basket

In a conventional endoscope, a position of a channel opening serving as a projection position of a treatment tool is fixed, and the projection position cannot be changed. However, there is an issue that the projection position of the treatment tool from the tip portion of the endoscope is desired to be controlled appropriately depending on a content of treatment. The following description will be given using an example of extraction of a gallstone from the biliary duct. Note that an example of removal of a kidney stone will be described with reference to FIG. 37 or subsequent drawings.

Figure 20:
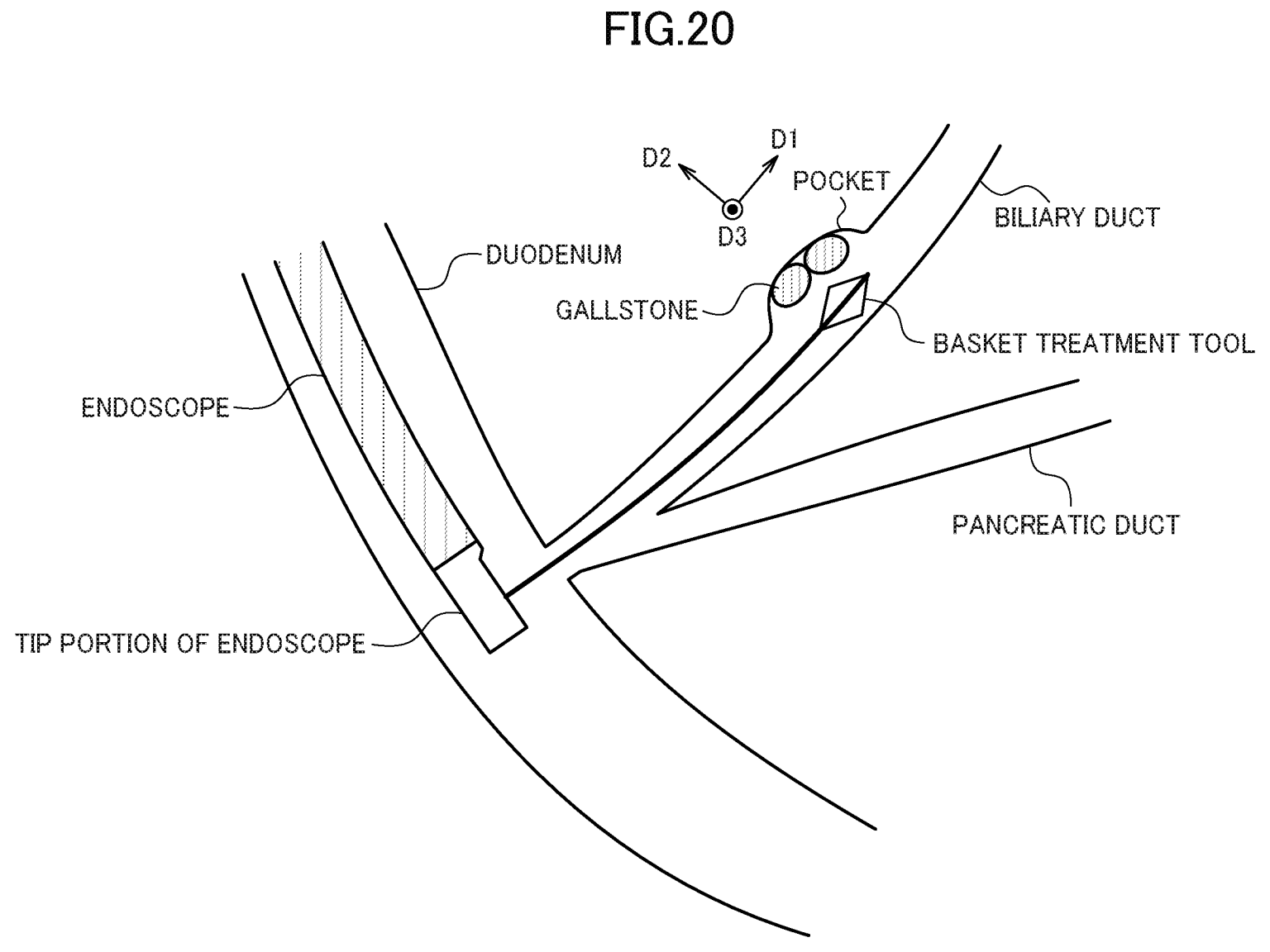

FIG. 20 is a diagram for describing a pocket case of a gallstone. FIG. 20 illustrates an example of a transmissive image in the gallstone is captured. Assume that a direction along the biliary duct is a direction D1, a direction orthogonal to the direction D1 in a plane of the transmissive image is D2, and a direction orthogonal to the directions D1 and D2 is a direction D3.

The gallstone is a calculus generated in the biliary duct. There is a case where a dent in a pocket shape is formed in a duct line of the biliary duct, and the gallstone is stuck in the pocket. This is referred to as a pocket case. FIG. 20 illustrates an example in which a pocket is generated on the direction D2 side of the biliary duct. Since the basket treatment tool is inserted along the direction D1, which is a longitudinal axis of the duct line, the basket treatment tool is hard to be inserted in the direction D2, in which the pocket is present. Thus, in manipulation of removal of the gallstone using the basket treatment tool, there is an issue that the basket treatment tool is difficult to be inserted so as to fetch a calculus in the pocket. The specification of United States Patent Application Publication No. 2007/0185377 described above discloses robot assistance for manipulation of extraction of a stone using a basket, but discloses neither a assistance method dedicated to the pocket case nor a specific control method for changing an insertion direction of the basket.

FIG. 21 is a diagram illustrating a method of removing the gallstone in the pocket in accordance with the present embodiment. Assume that a positional relationship between the papillary orifice and the tip portion of the endoscope is not changed. In the normal ERCP method, since manipulation is performed, for example, in a state where a camera is set at the correct position with respect to the papillary orifice and the papillary orifice is located at the center of an image, the positional relationship between the papillary orifice and the tip portion of the endoscope basically stays constant.

In the present embodiment, the insertion direction and projection position of the basket treatment tool in/at which the basket treatment tool is easily inserted into the pocket is determined based on the transmissive image in which the biliary duct is captured, and the basket treatment tool is projected in the insertion direction at the projection position. In an example in FIG. 21, the basket treatment tool is projected in a direction leaning from a side closer to the tip of the tip portion of the endoscope toward the base end side of the endoscope. With this configuration, the basket treatment tool is inserted into the biliary duct while the tip of the basket treatment tool is pressed against the inner wall of the biliary duct on the direction D2 side, whereby the basket treatment tool becomes easy to be inserted into the pocket.

Figure 22:
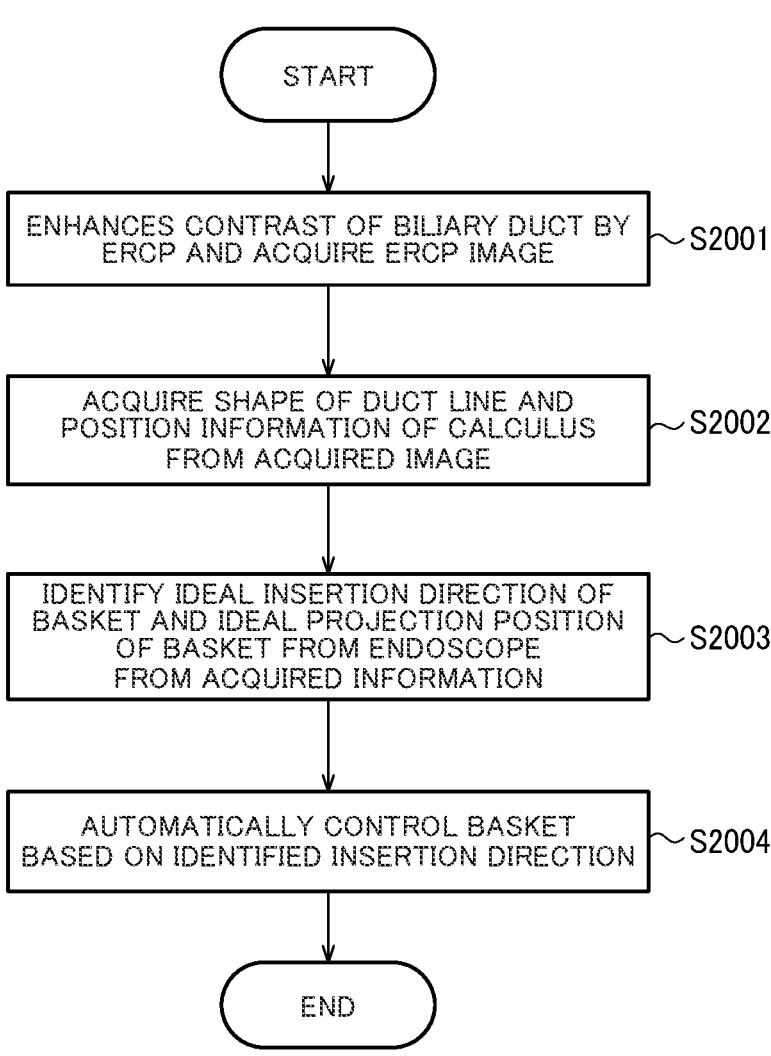
FIG. 22 illustrates the flow of processing of controlling an insertion direction and projection position of a basket treatment tool in the pocket case.

FIG. 22 illustrates the flow of processing of controlling the insertion direction and projection position of the basket treatment tool in the pocket case. In step S2001, the drive control device 2200 acquires image data of the transmissive image in which the abdomen of a patient is seen. The transmissive image is an image in which at least the biliary duct is captured, and furthermore, at least one of the duodenum, the papillary portion, the biliary duct, the pancreatic duct, the endoscope, or the treatment tool may be seen. For example, the biliary duct is contrast-enhanced by the ERCP, an ERCP image is captured by an X-ray imaging device or a computed tomography (CT) device, and the drive control device 2200 acquires image data of the captured ERCP image. Alternatively, a magnetic resonance cholangiopancreatography (MRCP) image is captured by a magnetic resonance imaging (MRI) device, and the drive control device 2200 acquires image data of the captured MRCP image.

Figure 23:
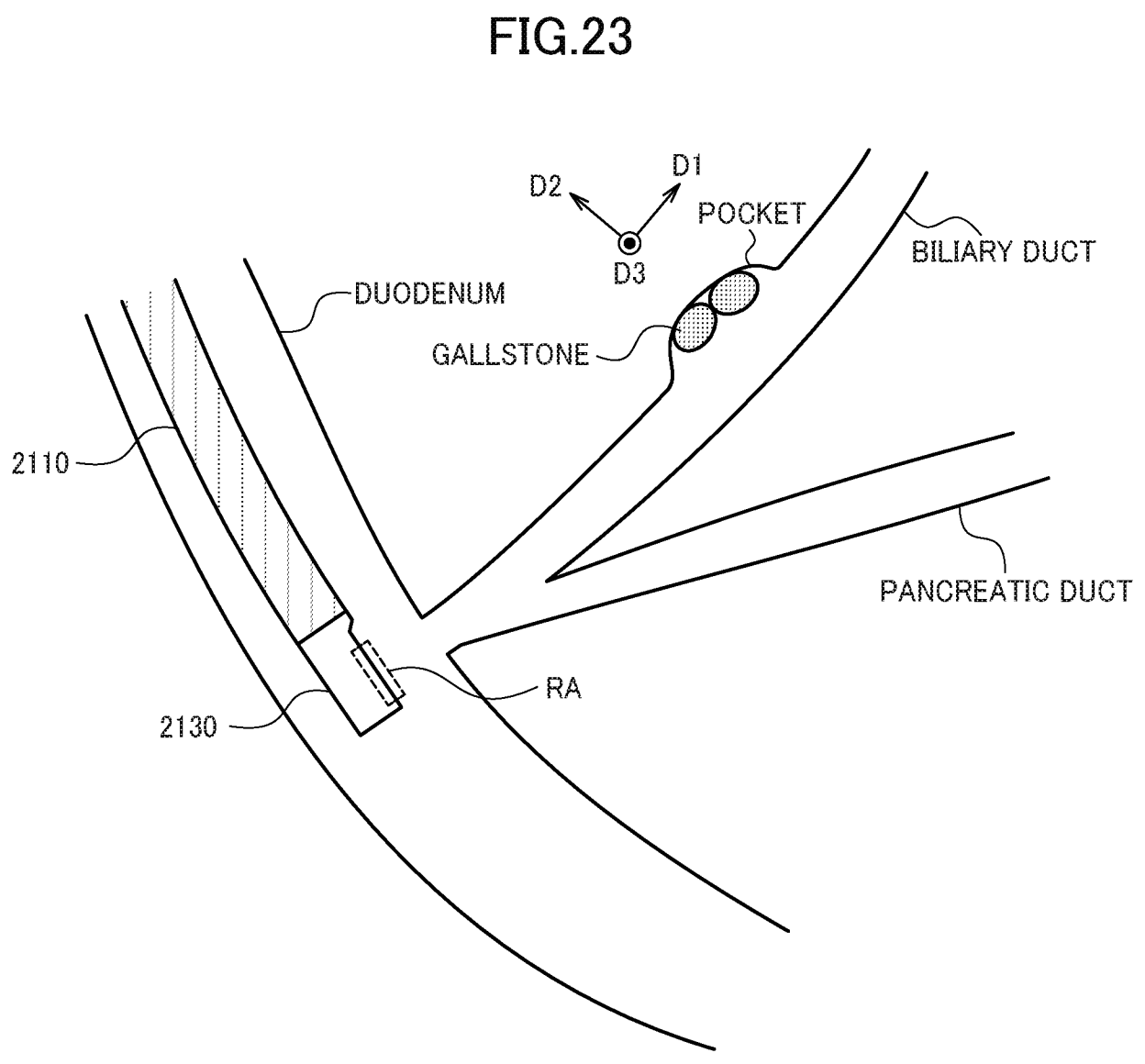

In step S2002, the drive control device 2200 acquires the shape of the duct line of the biliary duct and position information of the calculus from the transmissive image. FIG. 23 is a diagram for describing step S2002. In the ERCP, since the biliary duct is contrast-enhanced, the image of the biliary duct is captured in high luminance or low luminance in the transmissive image in comparison with images of surrounding tissues. In addition, since the gallstone is not contrast-enhanced, an image of the gallstone is captured in different luminance. The drive control device 2200, for example, recognizes an image of a duct line region in high luminance or low luminance, and thereby acquires shape information indicating the shape of the biliary duct such as a traveling direction, thickness, pocket, or the like of the biliary duct. Alternatively, the drive control device 2200 recognizes an image of a region in luminance that is different from the luminance of the biliary duct on the duct line, and thereby acquires position information indicating the position of the gallstone in the biliary duct. The above-mentioned image recognition may be implemented by image processing using machine learning.

In step S2002, the drive control device 2200 acquires information of a basket projectable range RA in which the basket treatment tool 3400 can be projected from the tip portion 2130 of the endoscope. For example, the endoscope includes a memory that is not illustrated and that stores therein information of the basket projectable range RA, and the drive control device 2200 reads out the information of the basket projectable range RA from the memory. Alternatively, the drive control device 2200 may store the information of the basket projectable range RA. For example, a storage section 2280 in FIG. 32 may store the information of the basket projectable range RA.

Figure 24:
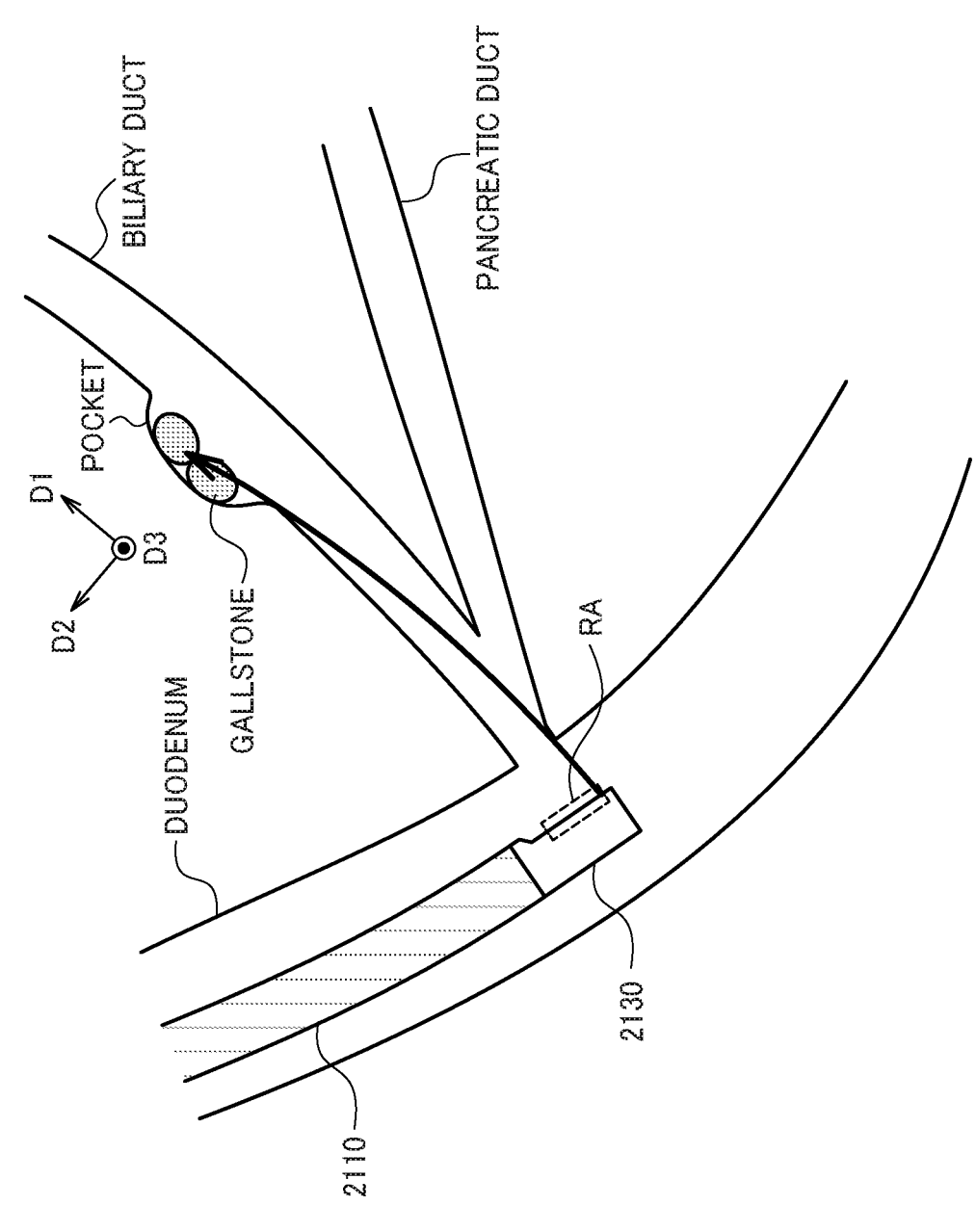
FIG. 24 is a diagram for describing identification of the insertion direction.

In step S2003, the drive control device 2200 identifies a direction in which the basket treatment tool 3400 is projected from the tip portion 2130 of the endoscope, based on the shape information of the duct line, the position information of the gallstone, and the information of the basket projectable range RA, each of which is acquired in step S2002. FIG. 24 is a diagram for describing identification of the insertion direction. In FIG. 24, there is the pocket on the direction D2 side of the duct line of the biliary duct. In this case, the drive control device 2200 identifies the insertion direction of the basket treatment tool 3400 as a direction inclined toward the direction D2 with respect to a direction parallel to the direction D1.

Subsequently, the drive control device 2200 determines the projection position of the basket treatment tool 3400 based on the identified insertion direction. FIG. 25 is a diagram for determining the projection position. In a case where the insertion direction is inclined toward the direction D2 side, the drive control device 2200 determines the projection position to be a position in the tip direction of the endoscope, which is the opposite direction of the inclination direction. The projection position is set in the basket projectable range RA.

Figure 26:
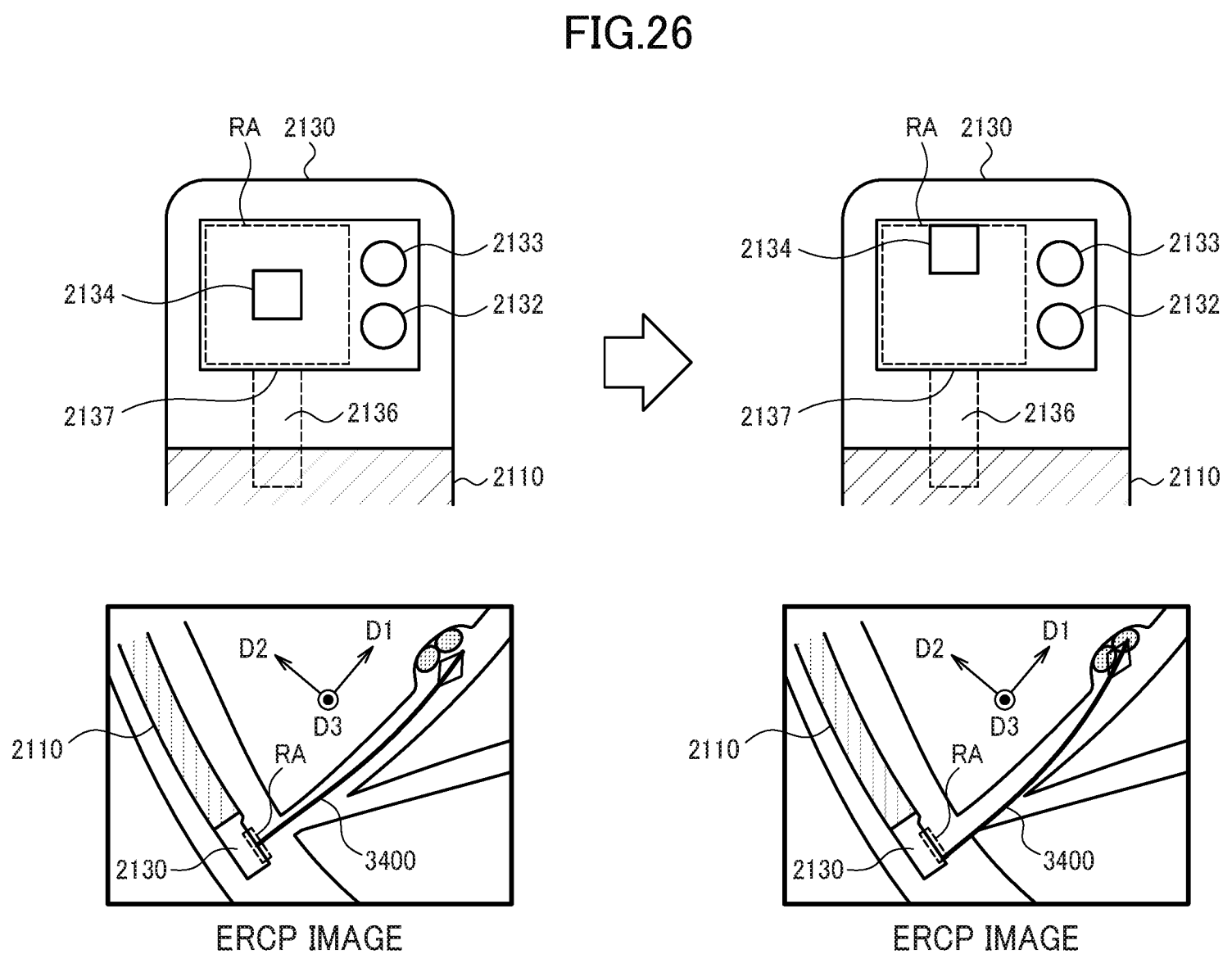

In step S2004, the drive control device 2200 automatically controls the endoscope and the basket treatment tool 3400 based on the insertion direction and the projection position that are identified in step S2003. FIG. 26 illustrates a first example of automatic control. The tip portion 2130 of the endoscope includes a camera 2132, an illumination lens 2133, a raising base 2134, a channel 2136, and a channel opening 2137.

The raising base 2134 raises the treatment tool, which passes through the channel 2137 and extends from the channel opening 2138 toward the direction of the raising base 2134, in a side surface direction of the tip portion 2130. The raising base 2134 is arranged in the tip portion 2130 so as to be slidable in a plane that is parallel with a sensor surface of the camera 2132. Specifically, the raising base 2134 is arranged so as to be slidable in the tip direction and base end direction of the endoscope. FIG. 26 illustrates an example of automatic control when the insertion direction and the projection position are determined as illustrated in FIGS. 24 and 25. The drive control device 2200 moves the raising base 2134 in the tip direction of the endoscope, and also increases a rising angle of the raising base 2134. In the transmissive image, the rising angle of the raising base 2134 is changed so that the insertion direction is rotated in a counterclockwise direction when viewed from the front side. Note that a movable range of the raising base 2134 corresponds to the basket projectable range RA in FIG. 26, and FIG. 27 that will be described later.

Subsequently, the basket treatment tool 3400 is inserted into the biliary duct, and the gallstone is removed from the biliary duct. The drive control device 2200 automatically controls the electrically driven basket treatment tool 3400 to perform an operation of removal of the gallstone. Alternatively, the operator may manually operate the electrically driven basket treatment tool 3400 using the operation input section or manually operate a non-electrically driven basket treatment tool 3400 to perform the operation of removal of the gallstone.

FIG. 27 illustrates a second example of automatic control. In this example, there is a pocket on the direction D3 side of the biliary duct, that is, on the front side of a plane of paper. In this case, the insertion direction and the projection position are determined so that the basket treatment tool 3400 is pressed against an inner wall of the biliary duct on the direction D3 side and projects from the opposite direction side of the direction D3 to the direction D3 side, that is, from the rear side of the plane of paper to the front side of the plane of paper. The raising base 2134 is arranged so as to be slidable not only in the tip direction and the base end direction, but also in left-and-right directions orthogonal to these directions. In the example in FIG. 27, the drive control device 2200 moves the raising base 2134 in a left direction when viewed from a side surface of the tip portion 2130 side, that is, the rear side of the plane of paper in the transmissive image. The drive control device 2200 rolls the tip portion 2130 so that the basket treatment tool 3400 projects in the counterclockwise direction when viewed from the tip in the base end direction, that is, from the rear side of the plane of paper to the front side of the plane of paper in the transmissive image.

In the present embodiment, the medical system 2010 includes the endoscope 2100 in which the treatment tool 2400 is projectable from the tip portion 2130, and a control device 2600. The control device 2600 acquires a body cavity image in which a body cavity including an object of treatment of the treatment tool 2400 is captured. The control device 2600 identifies, from the body cavity image, at least one of body cavity shape information indicating a shape of the body cavity or position information indicating a position of the object of the treatment in the body cavity as identification information. The control device 2600 controls a projection position of the treatment tool 2400 from the tip portion 2130 of the endoscope 2100 based on the identification information.

In accordance with the present embodiment, the projection position of the treatment tool 2400 from the tip portion 2130 of the endoscope 2100 is controlled in consideration of at least one of the shape of the body cavity or the position of the object of the treatment. This enables control of the projection position of the treatment tool 2400 to be a projection position appropriate for treatment using the treatment tool 2400 relative to at least one of the shape of the body cavity or the position of the object of the treatment. For example, in FIGS. 19 to 27, the projection position is controlled so as to allow the basket treatment tool 3400 to remove the gallstone appropriately with respect to the shape of the gallstone and the position of the gallstone in the biliary duct.

Note that the drive control device 2200 in FIGS. 19 to 27 corresponds to the control device 2600. As described later with reference to FIG. 30 and the like, the control device 2600 includes the drive control device 2200. In FIGS. 19 to 27, the transmissive image corresponds to the body cavity image. However, the body cavity image is not limited thereto, and is, for example, an endoscope image in FIG. 37 or subsequent drawings. In FIGS. 19 to 27, information indicating the shape of the biliary duct corresponds to the body cavity shape information, and the position of the gallstone in the biliary duct corresponds to the position information. However, each of the body cavity shape information and the position information is not limited thereto. For example, in FIG. 37 or subsequent drawings, the body cavity shape information is information indicating a shape of an inner cavity of the kidney, and the position information is information indicating a position of a kidney stone in the inner cavity of the kidney.

In the present embodiment, the treatment tool 2400 is the basket treatment tool 3400 projectable from the side surface of the tip portion 2130 of the endoscope 2100. In the present embodiment, the body cavity is the biliary duct. The object of the treatment is the gallstone in the biliary duct.

The present embodiment enables control of the projection position of the basket treatment tool 3400 so as to allow the basket treatment tool 3400 to remove the gallstone appropriately relative to the shape of the biliary duct or the position of the gallstone in the biliary duct.

In the present embodiment, in the tip portion 2130 of the endoscope 2100, the position at which the basket treatment tool 3400 is projected from the side surface is variable. The control device 2600 controls the position at which the basket treatment tool 3400 is projected from the side surface.

In accordance with the present embodiment, the position at which the basket treatment tool 3400 is projected from the side surface of the tip portion 2130 of the endoscope 2100 being variable allows the control device 2600 to control the projection position of the treatment tool 2400 from the tip portion 2130 of the endoscope 2100 based on the identification information.

In the present embodiment, the tip portion 2130 of the endoscope 2100 includes the raising base 2134 that controls the projection direction, in which the treatment tool 2400 is projected from the tip portion 2130. The control device 2600 controls a position of the raising base 2134 in the tip portion 2130, and thereby controls the projection position of the treatment tool 2400.

The raising base 2134 raises an orientation of the treatment tool 2400 from an axis line direction of the endoscope 2100 to the side surface direction, and thereby projects the treatment tool 2400 from the side surface of the tip portion 2130. That is, changing the position of the raising base 2134 can change the projection position of the treatment tool 2400. In accordance with the present embodiment, the control device 2600 controls the position of the raising base 2134 in the tip portion 2130 based on the identification information, and can thereby control the projection position of the treatment tool 2400 based on the identification information.

In accordance with the present embodiment, the control device 2600 performs control to move the position of the raising base 2134 in the tip portion 2130 in a direction crossing the projection direction of the treatment tool 2400, and thereby controls the projection position of the treatment tool 2400.

In accordance with the present embodiment, the control device 2600 moves the position of the raising base 2134 in the tip portion 2130 to the direction crossing the projection direction of the treatment tool 2400 based on the identification information, and can thereby control the projection position of the treatment tool 2400 based on the identification information.

Note that the projection direction of the treatment tool 2400 is the side surface direction of the tip portion 2130. The direction crossing the projection direction is the axis line direction of the endoscope 2100 or the direction orthogonal to the axis line direction and the side surface direction. Alternatively, when a consideration is given based on a visual field of the camera 2132, the direction crossing the projection direction can be said as an up-and-down direction and left-and-right direction of the visual field of the camera 2132.

The present embodiment may be implemented as a treatment tool control method as follows. That is, the treatment tool control method is a method of controlling the treatment tool 2400 projectable from the tip portion 2130 of the endoscope 2100. The treatment tool control method includes a step of acquiring the body cavity image in which the body cavity including the object of treatment of the treatment tool 2400 is captured. The treatment tool control method includes a step of identifying, from the body cavity image, at least one of the body cavity shape information indicating the shape of the body cavity or the position information indicating the position of the object of the treatment in the body cavity as the identification information. The treatment tool control method includes a step of controlling the projection position of the treatment tool 2400 from the tip portion 2130 of the endoscope 2100 based on the identification include information.

The present embodiment may be implemented as an operation method for the medical system 2010 as follows. The medical system 2010 plays a main role in performing each step. The operation method includes the step of acquiring the body cavity image in which the body cavity including the object of treatment of the treatment tool 2400 is captured. The operation method includes the step of identifying, from the body cavity image, at least one of the body cavity shape information indicating the shape of the body cavity or the position information indicating the position of the object of the treatment in the body cavity as the identification information. The operation method includes the step of controlling the projection position of the treatment tool 2400 from the tip portion 2130 of the endoscope 2100 based on the identification information.

The present embodiment may be implemented as a program or a non-transitory storage medium that stores the program as follows. The program causes a computer to execute the step of acquiring the body cavity image in which the body cavity including the object of treatment of the treatment tool 2400 is captured. The program causes the computer to execute the step of identifying, from the body cavity image, at least one of the body cavity shape information indicating the shape of the body cavity or the position information indicating the position of the object of the treatment in the body cavity as the identification information. The program causes the computer to execute the step of controlling the projection position of the treatment tool 2400 from the tip portion 2130 of the endoscope 2100 based on the identification information.

2. ERCP and Medical System

A configuration example of the medical system including the basket treatment tool 3400 will be described below. First, manipulation of the ERCP using the medical system is described. The ERCP is an abbreviation for endoscopic retrograde cholangiopancreatography.

Figure 28:
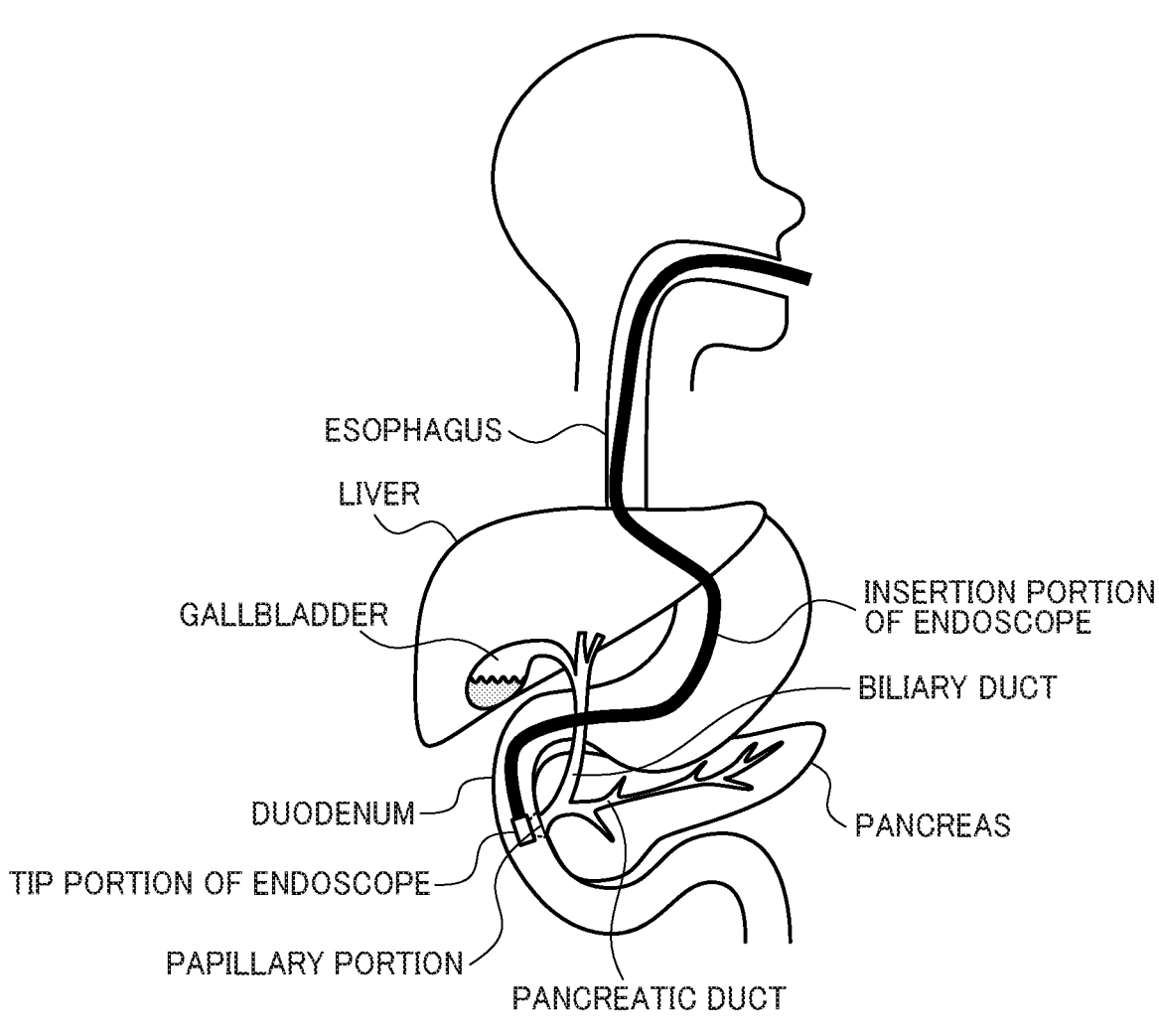
FIG. 28 illustrates organs and tissues that are related to manipulation of endoscopic retrograde cholangiopancreatography (ERCP).

FIG. 28 illustrates organs and tissues that are related to the manipulation of the ERCP. Note that an organ has a unique structure in which a plurality of types of tissues gathers together, and has a specific function. In FIG. 28, the liver, the gallbladder, the pancreas, the esophagus, the stomach, and the duodenum correspond to the organs. The tissues are formed by related cells being coupled to each other, such as blood vessels, muscles, and skin. In FIG. 28, the biliary duct and the pancreatic duct correspond to the tissues.

The object of the treatment by the ERCP is the biliary duct. The biliary duct is a duct line for flowing biliary created by the liver to the duodenum. To approach the biliary duct with the endoscope, the treatment tool that is inserted through a channel of the endoscope is inserted from the papillary portion of the duodenum to the biliary duct while the endoscope remains to be held at a position of the duodenum. The papillary portion of the duodenum is hereinafter simply referred to as the papillary portion. The papillary portion is a region including an orifice in which luminal tissues open to the duodenum, and not only the orifice but also a structure in the periphery of the orifice is referred to as the papillary portion. The orifice of the luminal tissues is a portion, in which a common duct in which the biliary duct and the pancreatic duct join together, opens to the duodenum. However, the papillary portion varies among different individuals, and there is a case where, for example, the biliary duct and the pancreatic duct do not join together and the biliary duct opens directly to the duodenum. In such a case, the orifice of the luminal tissues is the orifice of the biliary duct.

Figure 29:
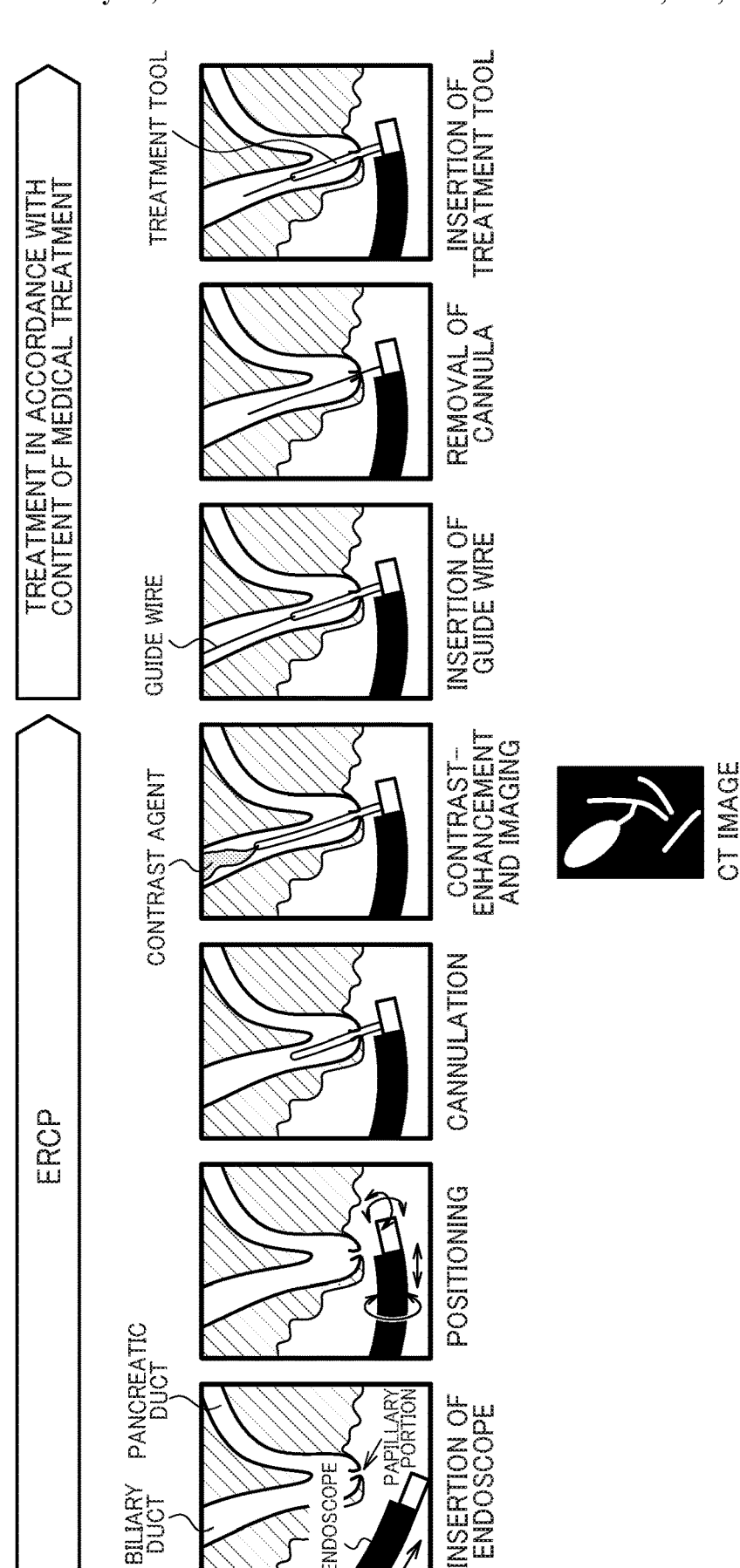
FIG. 29 illustrates the flow of treatment in accordance with the ERCP and a content of medical treatment.

FIG. 29 illustrates the flow of treatment in accordance with the ERCP and a content of medical treatment. A side-view-type endoscope provided with a camera, a illumination lens, and an opening of a treatment tool channel on the side surface of the tip portion of the endoscope is used for the ERCP. Note that the camera is also referred to as an imaging device.

In an endoscope insertion step, an insertion portion of the endoscope is inserted from the mouth, by way of the esophagus and the stomach, into the duodenum. At this time, the insertion portion is inserted to a position where the papillary portion is roughly seen in a visual field of the endoscope. Subsequently, in an positioning step, the endoscope is aligned with the papillary portion. Specifically, the position of the tip portion of the endoscope is adjusted so that the papillary portion is within an imaging range of the camera of the endoscope. Alternatively, the position of the tip portion of the endoscope is adjusted so that the camera of the endoscope is at a correct position with respect to the papillary portion and is seen at the center of the field view.

Subsequently, in a cannulation step, a cannula is inserted from the papillary portion to the biliary duct. Specifically, the cannula is inserted into the treatment tool channel of the endoscope to project the cannula from a channel opening in the tip portion of the endoscope, a tip of the cannula is put in an orifice of the common duct and inserted into the common duct, and furthermore, the cannula is inserted from a joint portion of the biliary duct and the pancreatic duct toward a direction of the biliary duct. Note that the cannulation is insertion of the cannula into the body. The cannula is a medical tube that is inserted into the body and used for a medical purpose.

Subsequently, in a contrast-enhancement and imaging step, a contrast agent is injected into the cannula and is poured from the tip of the cannula into the biliary duct. X-ray imaging or CT imaging is performed in this state, whereby an X-ray image or a CT image, in which the biliary duct, the gallbladder, and the pancreatic duct are seen, is acquired. This is the manipulation of the ERCP, and thereafter various kinds of treatment are performed in accordance with results of diagnosis based on the X-ray image or the CT image. One example of the treatment will be described below.

In a guide wire insertion step, a guide wire is inserted into the cannula to project the guide wire from the tip of the cannula, and the guide wire is inserted into the biliary duct. In a cannula removal step, the cannula is removed while the guide wire is left inside the biliary duct. This leads to a state where only the guide wire projects from the tip of the endoscope and is left inside the biliary duct. Subsequently, in a treatment tool insertion step, the treatment tool is inserted into the biliary duct along the guide wire. The treatment tool is, for example, the basket treatment tool exemplified in the present embodiment, but may be a stent or the like. Note that the stent is a treatment tool that is inserted into a narrowed part of the biliary duct to expand the narrowed part, and is left after insertion to maintain an expanded state of the narrowed part.

Figure 30:
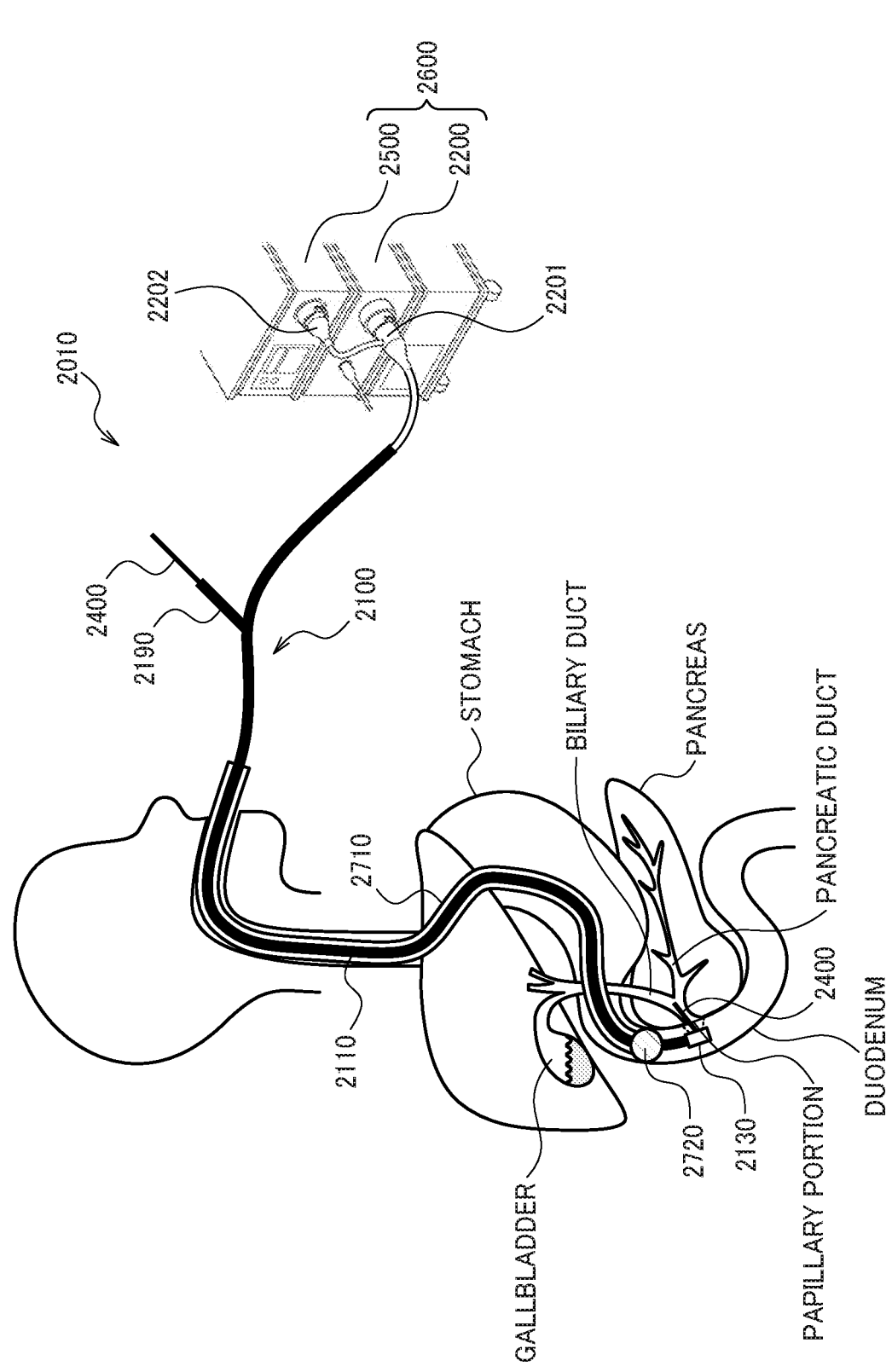
FIG. 30 illustrates a configuration example of a medical system.

FIG. 30 illustrates a configuration example of the medical system 2010 in accordance with the present embodiment. The medical system 2010 includes the endoscope 2100, the treatment tool 2400, and the control device 2600. The control device 2600 includes the drive control device 2200 to which a connector 2201 is connected, and a video control device 2500 to which a connector 2202 is connected. The endoscope 2100 is detachably connected to the control device 2600 by the connectors 2201 and 2202.

Note that the medical system 2010 is also referred to as an endoscope system. Additionally, in a case where the endoscope 2100 is of a electrically driven type, the medical system 2010 can be also referred to as an electrically driven endoscope system. While FIG. 30 exemplifies the medical system 2010 using the endoscope 2100 of the electrically driven type, the endoscope 2100 may be of a non-electrically driven, manual type regarding a portion that is not related to electric driving of the basket treatment tool. For example, advancing/retreating, rolling, and angling of the endoscope 2100 may be non-electrically driven operations, and position change of the raising base and angling of the rising angle may be electrically driven operations.

The electric driving mentioned herein means that the endoscope or the treatment tool is driven by a motor or the like based on an electric signal for controlling an operation of the endoscope or the treatment tool. For example, in a case where the electric driving is manually operated, an operation input to an operation device is converted to an electric signal, and the endoscope or the treatment tool is driven based on the electric signal.

The control device 2600 controls each section of the drive control device 2200, the video control device 2500, and the like, and plays a main role in performing the processing flow that has been described with reference to FIG. 22 and the like. The control device 2600 includes the following hardware. The hardware can include at least one of a circuit that processes a digital signal or a circuit that processes an analog signal. For example, the hardware can include one or more circuit devices mounted on a circuit board, or one or more circuit elements. The one or more circuit devices are, for example, integrated circuits (ICs), field-programmable gate array (FPGA) circuits, or the like. The one or more circuit elements are, for example, resistors, capacitors, or the like.

In addition, the control device 2600 may include one or more processors described below. The control device 2600 includes a memory that stores information, and a processor that operates based on the information stored in the memory. The information is, for example, a program, various kinds of data, and the like. The processor includes hardware. Note that various kinds of processors such as a central processing unit (CPU), a graphics processing unit (GPU), and a digital signal processor (DSP) can be used. The memory may be a semiconductor memory such as a static random-access memory (SRAM) and a dynamic random-access memory (DRAM). The memory may be a register. The memory may be a magnetic storage device such as a hard disk drive (HDD). The memory may be an optical storage device such as an optical disk device. For example, the memory stores a computer-readable instruction. The instruction is executed by the processor, whereby part or all of functions of each section of the control device 2600 is implemented as processing. The instruction mentioned herein may be an instruction of an instruction set that is included in a program, or may be an instruction that instructs a hardware circuit included in the processor to operate. Furthermore, all or part of each section of the control device 2600 can be implemented by cloud computing, and each processing described with reference to FIG. 22 or the like can be executed on the cloud computing. The above-mentioned program can be stored in a non-transitory information storage medium, which is a computer readable storage medium. The information storage medium is implemented by, for example, an optical disk, a memory card, an HDD, a semiconductor memory, or the like. The semiconductor memory is, for example, a read-only memory (ROM) or a non-volatile memory.

The drive control device 2200 controls electric driving of the endoscope 2100 through the connector 2201. The drive control device 2200 can be implemented by including a processor similar to the above-mentioned processor. Although not illustrated in FIG. 30, an operation device for manually operating electric driving may be connected to the drive control device 2200.

The video control device 2500 receives an image signal from the camera arranged in the tip portion 2130 of the endoscope 2100 through the connector 2202, generates a display image from the image signal, and performs processing of displaying the display image on a display device, which is not illustrated. The video control device 2500 can be implemented by including a processor similar to the above-mentioned processor.

Note that the drive control device 2200 and the video control device 2500 are illustrated as individual devices in FIG. 30, but may be configured as an integrated device. In this case, the connectors 2201 and 2202 may be integrated as one connector. The following description will be given assuming that the control device 2600, the drive control device 2200, the video control device 2500 each include an individual processor, but the configuration is not limited thereto. For example, a processor or the like of the control device 2600 may fulfill a function as the drive control device 2200, and a processor or the like of the control device 2600 may fulfill a function as the drive control device 2200 and the video control device 2500.

The endoscope 2100 includes the insertion portion 2110. The insertion portion 2110 is a portion inserted into a lumen of the patient, and is configured to be flexible in a long and thin shape. Note that details of the endoscope 2100 including a configuration other than the insertion portion 2110 will be described later. The insertion opening 2190 of the treatment tool is arranged on the base end side of the insertion portion 2110, and the treatment tool channel for passing the treatment tool 2400 from the insertion opening 2190 to the opening of the tip portion 2130 is arranged inside the insertion portion 2110. The insertion opening 2190 of the treatment tool is also referred to as a forceps opening, but the treatment tool to be used is not limited to a forceps.

Note that a configuration example of the medical system 2010 in accordance with the present embodiment is limited to the above-mentioned examples, and the medical system 2010 may further include, for example, an overtube 2710 and a balloon 2720 as illustrated in FIG. 30.

The overtube 2710 is a tube that covers the insertion portion 2110 of the endoscope 2100 and that is variable in hardness. In a state where the endoscope 2100 and the overtube 2710 are inserted into the body, at least a bending portion of the insertion portion 2110 is in an exposed state from a tip of the overtube 2710. The bending portion is a portion configured to be bent at an angle in accordance with a bending operation in the vicinity of the tip of the insertion portion 2110. In addition, a base end of the overtube 2710 is outside the body, and the base end side of the insertion portion 2110 is exposed from the base end of the overtube 2710.

The balloon 2720 is arranged in the vicinity of the outside tip of the overtube 2710. For example, the operator performs an operation of inflating the balloon 2720 arranged in the vicinity of the tip of the overtube 2710 to fix the tip of the overtube 2710 to the duodenum with the balloon 2720. This can fix the position of the tip of the overtube 2710.

The operator then performs, for example, an operation of hardening the overtube 2710. With this operation, the insertion portion 2110 is held and an insertion path of the insertion portion 2110 is thereby fixed. As a result, the insertion path of the insertion portion 2110 can be held. Note that a method of hardening the overtube 2710 is publicly known and thus a description thereof is omitted.

FIG. 31 illustrates a more detailed configuration example of the medical system 2010. FIG. 31 illustrates the medical system 2010 for observing or performing treatment on the inside of the body of a patient lying on an operating table TA. The medical system 2010 in FIG. 31 includes the endoscope 2100, the control device 2600, the operation device 2300, the treatment tool 2400, an advancing/retreating driving device 2800, and the display device 2900.

The endoscope 2100 is a device that is inserted into the lumen of the patient for observation of a diseased part. In addition, the treatment tool 2400 can be inserted through the endoscope 2100. The treatment tool 2400 is projected from the tip portion 2130, whereby treatment on the lumen can be performed with the treatment tool 2400. In the present embodiment, an insertion side of the endoscope 2100 and the treatment tool 2400 into the lumen of the patient is referred to as a "tip side", and a mounting side of the endoscope 2100 and the treatment tool 2400 to the control device 2600 is referred to as a "base end side". Movement of the endoscope 2100 and the treatment tool 2400 toward the tip side is referred to as "advancing", and movement thereof toward the base end side is referred to as "retreating". These are also collectively referred to as "advancing/retreating".

The endoscope 2100 includes the insertion portion 2110 described above with reference to FIG. 30, a coupling element 2125, an extracorporeal flexible portion 2145, and the connectors 2201 and 2202. The insertion portion 2110, the coupling element 2125, the extracorporeal flexible portion 2145, and the connectors 2201 and 2202 are connected to one another in this order from the tip side.

The insertion portion 2110 includes a bending portion 2102, an extracorporeal flexible portion that connects a base end of the bending portion 2102 and the coupling element 2125 to each other, and the tip portion 2130 arranged at the tip of the bending portion 2102. An internal path 2101 is arranged inside the insertion portion 2110, the coupling element 2125, and the extracorporeal flexible portion 2145, and a bending wire that passes through the internal path 2101 is connected to the bending portion 2102. The drive control device 2200 drives the wire through the connector 2201 to perform a bending operation of the bending portion 2102. A wire for the raising base to be connected to the raising base arranged in the tip portion 2130 passes through the internal path 2101 and is connected to the connector 2201. The drive control device 2200 drives the wire for the raising base to change a rising angle of the treatment tool 2400 that projects from the side surface of the tip portion 2130. The camera, the illumination lens, and the opening of the treatment tool channel are arranged on the side surface of the tip portion 2130. An image signal line that connects the camera and the connector 2202 to each other is arranged on the internal path 2101, and an image signal is transmitted from the camera to the video control device 2500 through the image signal line. The video control device 2500 displays an endoscope image generated from the image signal on the display device 2900.

The insertion opening 2190 of the treatment tool and a roll operating portion 2121 are arranged in the coupling element 2125. The treatment tool channel is arranged on the internal path 2101, one end of the treatment tool channel opens in the tip portion 2130, and the other end thereof opens in the insertion opening 2190 of the treatment tool. An extension tube 2192 that extends from the insertion opening 2190 to the operation device 2300 is connected to the insertion opening 2190. The treatment tool 2400 is inserted from an opening of the extension tube 2192 on the operation device 2300 side, passes through the insertion opening 2190 and the treatment tool channel, and projects from the opening of the tip portion 2130. Note that the extension tube 2192 may be omitted and the treatment tool 2400 may be inserted from the insertion opening 2190. The roll operating portion 2121 is attached to the coupling element 2125 to be rotatable about an axis line direction of the insertion portion 2110. A rotating operation of the roll operating portion 2121 rolls the insertion portion 2110. Note that the roll operating portion 2121 may be driven by a manual operation, or may be capable of being electrically driven.

The advancing/retreating driving device 2800 is a driving device that electrically drives the insertion portion 2110 to advance/retreat the insertion portion 2110. For example, the extracorporeal flexible portion 2145 is detachable from the advancing/retreating driving device 2800, and the advancing/retreating driving device 2800 slides the extracorporeal flexible portion 2145 in the axis line direction in a state where the extracorporeal flexible portion 2145 is mounted on the advancing/retreating driving device 2800, whereby the insertion portion 2110 advances/retreats. While FIG. 31 illustrates an example in which the extracorporeal flexible portion 2145 and the advancing/retreating driving device 2800 are detachable, the configuration is not limited thereto, and the coupling element 2125 and the advancing/retreating driving device 2800 may be configured to be detachable.

The operation device 2300 is detachably connected to the drive control device 2200 through an operation cable 2301. The operation device 2300 may perform wireless communication with the drive control device 2200 instead of wired communication. When the operator operates the operation device 2300, a signal of the operation input is transmitted to the drive control device 2200 through the operation cable 2301, and the drive control device 2200 electrically drives the endoscope 2100 so as to perform an endoscope operation in accordance with the operation input based on the signal of the operation input. The operation device 2300 includes five or more channels of operation input sections corresponding to advancing/retreating of the endoscope 2100, a bending operation in two directions, rolling, and an operation of the raising base. Note that in a case where there is a non-electrically driven operation among these operations, an operation input section for the operation may be omitted. Each operation input section includes, for example, a dial, a joy stick, an arrow key, a button, and a switch, a touch panel, and/or the like.

The drive control device 2200 drives a built-in motor based on an operation input to the operation device 2300 to electrically drive the endoscope 2100. Alternatively, in a case where the motor is an external motor outside the drive control device 2200, the drive control device 2200 transmits a control signal to the external motor based on the operation input to the operation device 2300 and controls electric driving. In addition, the drive control device 2200 may drive a built-in pump or the like based on the operation input to the operation device 2300 and cause the endoscope 2100 to perform air supply/suction. The air supply/suction is performed through an air supply/suction tube arranged on the internal path 2101. One end of the air supply/suction tube opens in the tip portion 2130 of the endoscope 2100, and the other end thereof is connected to the drive control device 2200 through the connector 2201. Note that the treatment tool channel may be extended to the connector 2201, and the treatment tool channel may also serve as the air supply/suction tube.

A block diagram in FIG. 32 illustrates a detailed configuration example of the drive control device 2200. The drive control device 2200 includes an image acquisition section 2270, the storage section 2280, a drive controller 2260, an operation reception section 2220, the wire driving section 2250, an air supply/suction driving section 2230, the communication section 2240, and an adaptor 2210.

The adaptor 2210 includes an adaptor for the operation device 2211 to which the operation cable 2301 is detachably connected and an adaptor for the endoscope 2212 to which the connector 2201 of the endoscope 2100 is detachably connected.

The wire driving section 2250 performs driving for the bending operation of the bending portion 2102 of the endoscope 2100 or the operation of the raising base of the treatment tool 2400, based on a control signal from the drive controller 2260. The wire driving section 2250 includes a motor unit for the bending operation that drives the bending portion 2102 of the endoscope 2100 and a motor unit for the raising base that drives the raising base. The adaptor for the endoscope 2212 has a coupling mechanism for the bending operation for coupling to the bending wire on the endoscope 2100 side. The motor unit for the bending operation drives the coupling mechanism, whereby driving force of the driving is transmitted to the bending wire on the endoscope 2100 side. The adaptor for the endoscope 2212 has a coupling mechanism for the raising base for coupling to the wire for the raising base on the endoscope 2100 side. The motor unit for the raising base drives the coupling mechanism, whereby driving force of the driving is transmitted to the wire for the raising base on the endoscope 2100 side.

The air supply/suction driving section 2230 performs driving for air supply/suction of the endoscope 2100 based on the control signal from the drive controller 2260. The air supply/suction driving section 2230 is connected to the air supply/suction tube of the endoscope 2100 through the adaptor for the endoscope 2212. The air supply/suction driving section 2230 is provided with a pump or the like, supplies the air to the air supply/suction tube, and sucks the air from the air supply/suction tube 2172.

The communication section 2240 performs communication with a driving device arranged outside the drive control device 2200. Communication may be either wireless communication or wired communication. The driving device arranged outside is the basket driving device that drives the basket treatment tool, the advancing/retreating driving device 2800 that advances/retreats the endoscope, a roll driving device that rolls the endoscope, an overtube driving device that changes hardness of the overtube 2710, a balloon driving device that changes a diameter of the balloon 2720, or the like.

The drive controller 2260 controls the advancing/retreating of the endoscope 2100, the bending operation and the rolling, the rising angle of the treatment tool 2400 formed by the raising base, the projection position of the treatment tool 2400, the operation of the treatment tool 2400, and the air supply/suction by the endoscope 2100. The operation of the treatment tool 2400 is advancing/retreating, opening/closing, or the like of the basket in the basket treatment tool 3400 illustrated in FIG. 19. In a case where control of the hardness of the overtube 2710 or the diameter of the balloon 2720 is performed by means of electric driving, the drive controller 2260 performs the control.

The image acquisition section 2270 is a communication interface that receives image data of the endoscope image from the video control device 2500 through wired communication or wireless communication. The image acquisition section 2270 outputs the received image data of the endoscope image to the drive controller 2260. In addition, the image acquisition section 2270 acquires image data of the transmissive image of the abdomen of the patient. The image data is used for the processing described with reference to FIG. 22 and the like. The transmissive image is, for example, an ERCP image captured by an X-ray imaging device for surgery or a CT device, or an MRCP image captured by an MRI device. MRCP is an abbreviation for magnetic resonance cholangiopancreatography. The transmissive image is captured at least when the processing described with reference to FIG. 22 and the like is performed, but may be captured in real time after the contrast-enhancement illustrated in FIG. 29.

The storage section 2280 stores information of a program and the like regarding drive control of the endoscope 2100. The storage section 2280 can be implemented by the storage device such as the semiconductor memory and the optical storage device that have been described above. Note that the storage section 2280 may store part or the whole of the program regarding the flow described in FIG. 22.

Additionally, the drive controller 2260 may be capable of performing control in a plurality of types of operation modes. Examples of the operation modes include a manual mode in which the operator manually operates electric driving of the endoscope 2100 or the like, and an automatic mode in which electric driving of the endoscope 2100 or the like is automatically controlled based on the endoscope image. For example, the positioning step described above with reference to FIG. 29 may be performed in the automatic mode. This enables automation of the positioning step.

Figure 33:
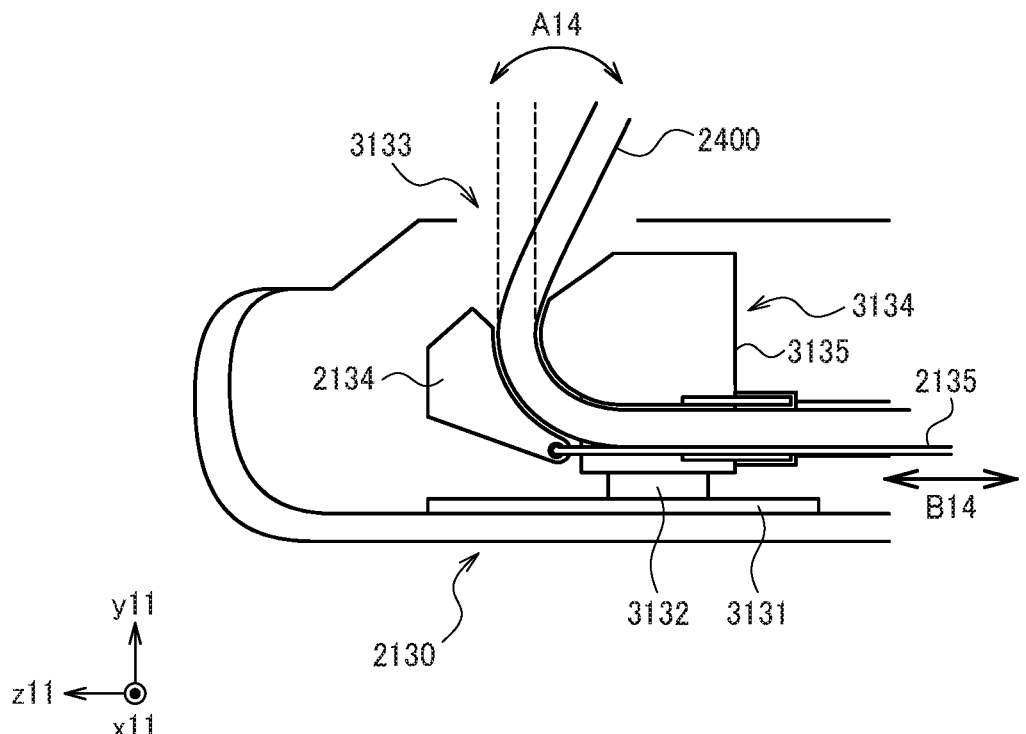
FIG. 33 illustrates a detailed configuration example of a tip portion of an endoscope, the tip portion including a raising base.

FIG. 33 illustrates a detailed configuration example of the tip portion 2130 of the endoscope including the raising base 2134. FIG. 33 omits illustration of the camera 2132 and the illumination lens 2133. As illustrated in FIG. 33, assume that a direction that is parallel to the axis line direction of the tip portion 2130 is a z11-direction, a direction that is parallel to a line-of-sight direction of the camera 2132 is a y11-direction, and a direction orthogonal to the z11- and y11-directions is an x11-direction. FIG. 33 is a cross-sectional view of the tip portion 2130 in a plane that is parallel to a y11-z11 plane of the treatment tool channel and that passes through an opening 3133 of the treatment tool channel.

The tip portion 2130 includes the raising base 2134 and a wire for the raising base 2135. The raising base 2134 can pivotally move about an axis that is parallel to the x11-direction. One end of the wire for the raising base 2135 is connected to the raising base 2134, and the other end thereof is connected to the drive control device 2200 through the connector 2201. The wire driving section 2250 of the drive control device 2200 presses/pulls the wire for the raising base 2135 as indicated in B14, whereby the raising base 2134 pivotally moves, and the rising angle of the treatment tool 2400 changes as indicated in A14. The rising angle is an angle of the treatment tool 2400 that projects from an opening 2131, and can be defined by, for example, an angle formed between the treatment tool 2400 that projects from the opening 2131 and the z11-direction.

Figure 34:
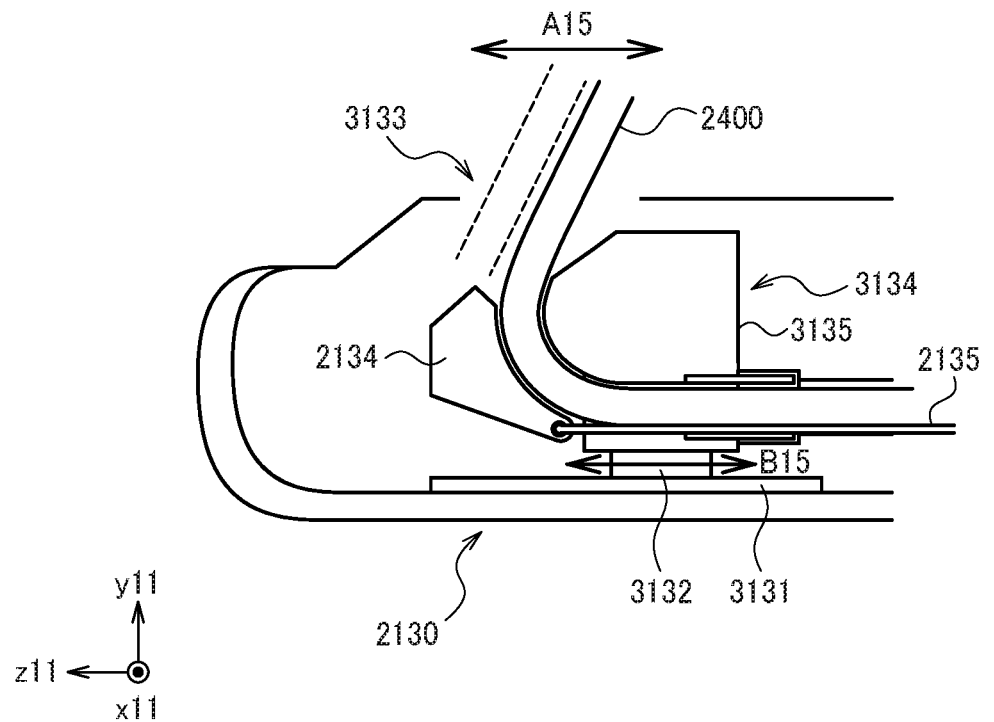
FIG. 34 is a diagram for describing a slide mechanism of the raising base.

FIG. 34 is a diagram for describing the slide mechanism of the raising base 2134. The tip portion 2130 includes a slider rail 3131 and a slider base 3132 that is connected to the slider rail 3131 so as to be slidable with respect to the slider rail 3131. A raising base portion 3134 including at least the raising base 2134 is connected to the slider base 3132. The raising base portion 3134 includes a base portion of the raising base 3135 arranged to face the raising base 2134. The treatment tool 2400 is inserted between the raising base 2134 and the raising base portion 3135. As indicated in B15, the slider base 3132 slides with respect to the slider rail 3131 in the z11-direction or a −z11-direction, whereby the raising base portion 3134 moves in the tip direction or the base end direction. With this movement, the projection position of the treatment tool 2400 moves in the tip direction or the base end direction as indicated in A15.

The above-mentioned slide mechanism is connected to the adaptor for the endoscope 2212 in FIG. 32 by the wire, which is not illustrated. The drive controller 2260 transmits a control instruction for a slide operation to the wire driving section 2250, and the wire driving section 2250 drives the wire through the adaptor for the endoscope 2212 based on the control instruction to drive the slide mechanism. Alternatively, the base end portion of the endoscope is provided with a motor that drives the slide mechanism, the motor and the slide mechanism are connected to each other by a wire or the like, the drive controller 2260 transmits a control instruction to the motor through the communication section 2240, and the motor drives the slide mechanism through the wire based on the control instruction.

While FIGS. 33 and 34 illustrate the slide mechanism that moves the projection position of the treatment tool 2400 in the tip direction or the base end direction, a slide mechanism that moves the projection position of the treatment tool 2400 in the left-and-right direction, that is, the x11-direction or a −x11-direction has a similar configuration.

Figure 35:
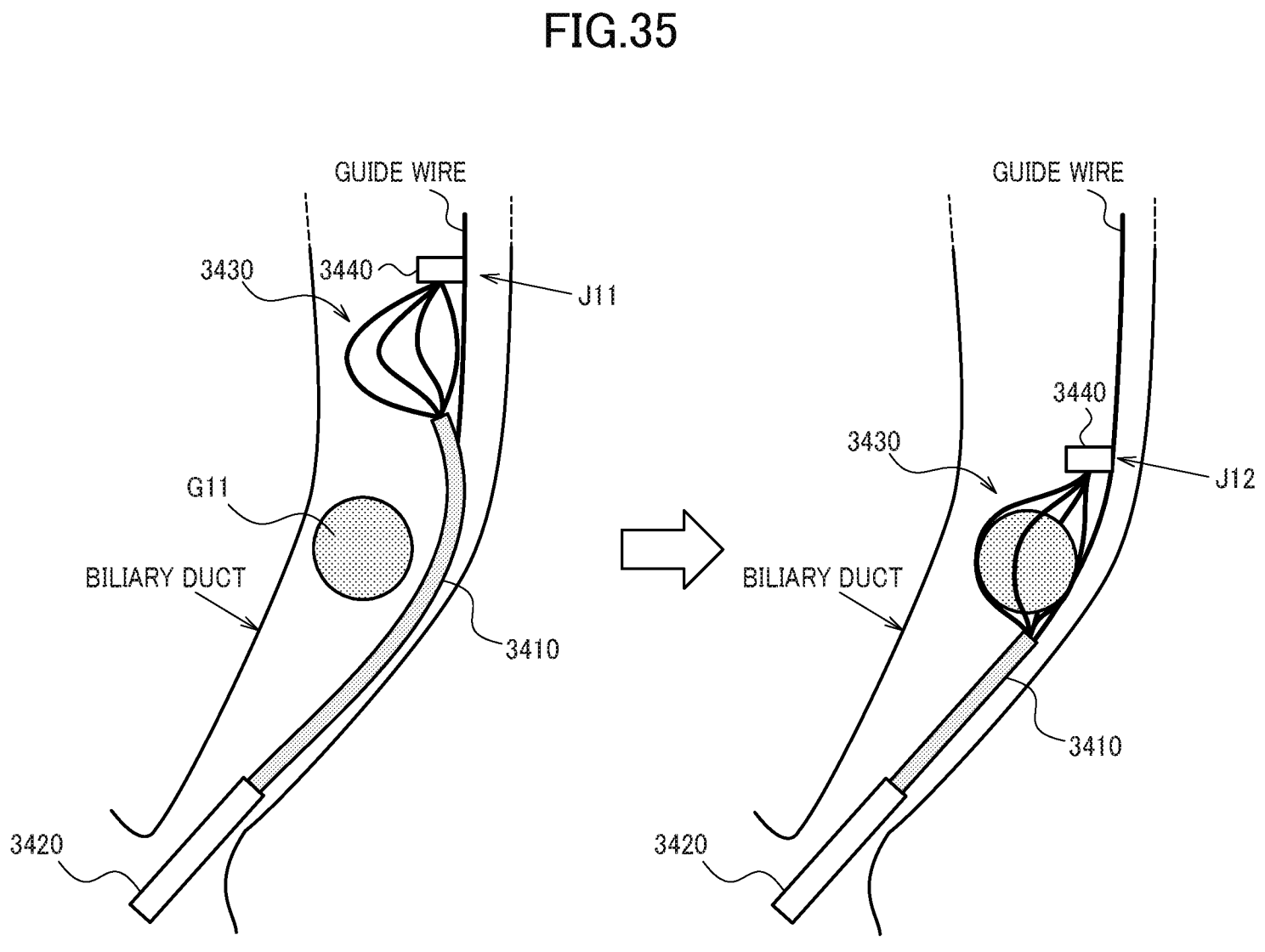
Figure 36:
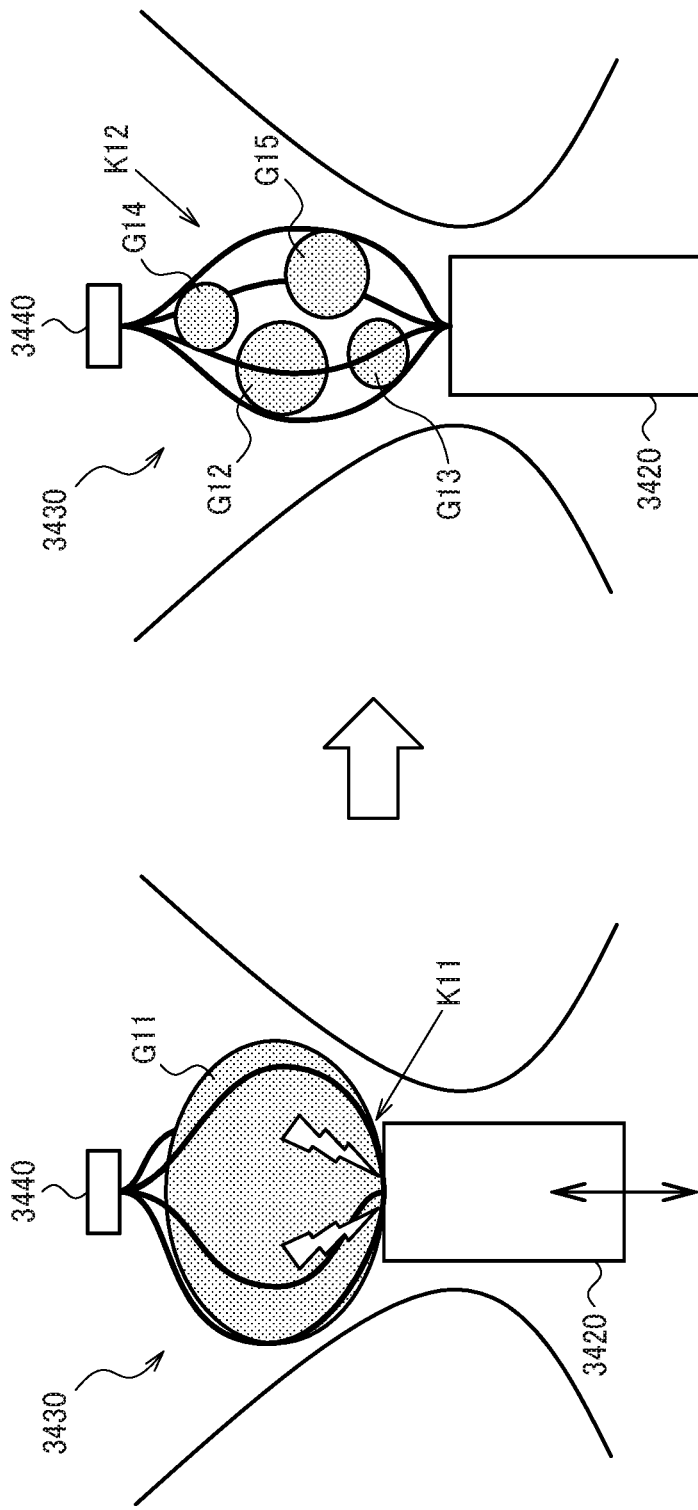
FIG. 36 is a diagram for describing crushing of a stone using the basket treatment tool.

FIG. 35 is a diagram for describing extraction of the stone using the basket treatment tool 3400. FIG. 36 is a diagram for describing crushing of the stone using the basket treatment tool 3400. The manipulation of removal of the stone and the manipulation of crushing of the stone described below may be performed under automatic control of the drive control device 2200, may be performed by a manual operation of the electrically driven basket by the operator, or may be performed by a manual operation of the non-electrically driven basket by the operator.

As illustrated in FIG. 35, in a case where a gallstone G11 is extracted by the basket treatment tool 3400, the tip of the first sheath 3410 of the basket treatment tool 3400 is positioned on an upstream side of the gallstone G11 in the biliary duct, and thereafter the tip member 3440 is projected from the first sheath 3410. For example, the advancing/retreating of the first sheath 3410 may be controlled by the operator while watching the transmissive image displayed on the display device 2900 or may be electrically controlled by the drive control device 2200 based on the image data of the transmissive image. With this control, the tip member 3440 and the basket 3430 are positioned on the upstream side of the gallstone G11 as indicated in J11.

The guide wire passes through an inner cavity, which is not illustrated, in the tip member 3440. This allows the tip member 3440 to move along the guide wire toward the upstream side or the downstream side, and also allows the tip member 3440 to rotate about the guide wire serving as a central axis.

The operator or the drive control device 2200 performs an operation of pulling the first sheath 3410 toward the base end side to fetch the gallstone G11 in the basket 3430 while moving the tip member 3440 along the guide wire toward a downstream portion of the biliary duct as indicated in J12. Note that the operator or the drive control device 2200 may advance/retreat the first sheath 3410 multiple times during a period of time until the gallstone G11 is fetched in the basket 3430, may open/close the basket 3430 multiple times, or may rotate the basket treatment tool 3400 about the guide wire.

As illustrated in FIG. 36, after the gallstone G11 is fetched in the basket 3430, the operator or the drive control device 2200 performs control of advancing a second sheath 3420 toward the upstream side. The second sheath 3420 is made of a hard material. Repetition of advancing/retreating of the basket 3430 to collide the gallstone G11 against the second sheath 3420 can make an impact on the gallstone G11 as indicated in K11. As a result, the gallstone G11 is crushed into, for example, gallstones G12 to G15 as indicated in K12.

3. Application to Removal of Kidney Stone

The above-mentioned medical system 2010 can also be applied to manipulation of removing a kidney stone. While the configuration of the medical system 2010 is as described above, an endoscope is not the above-mentioned side-view-type endoscope but is a direct-view-type endoscope. In the direct-view-type-endoscope, the camera, the illumination lens, and the opening of the treatment tool channel face the axis line direction and are arranged on a tip surface. Manipulation of extraction of the kidney stone or crushing of the kidney stone using the basket treatment tool is performed not based on the transmissive image, but on an endoscope image.

Figure 37:
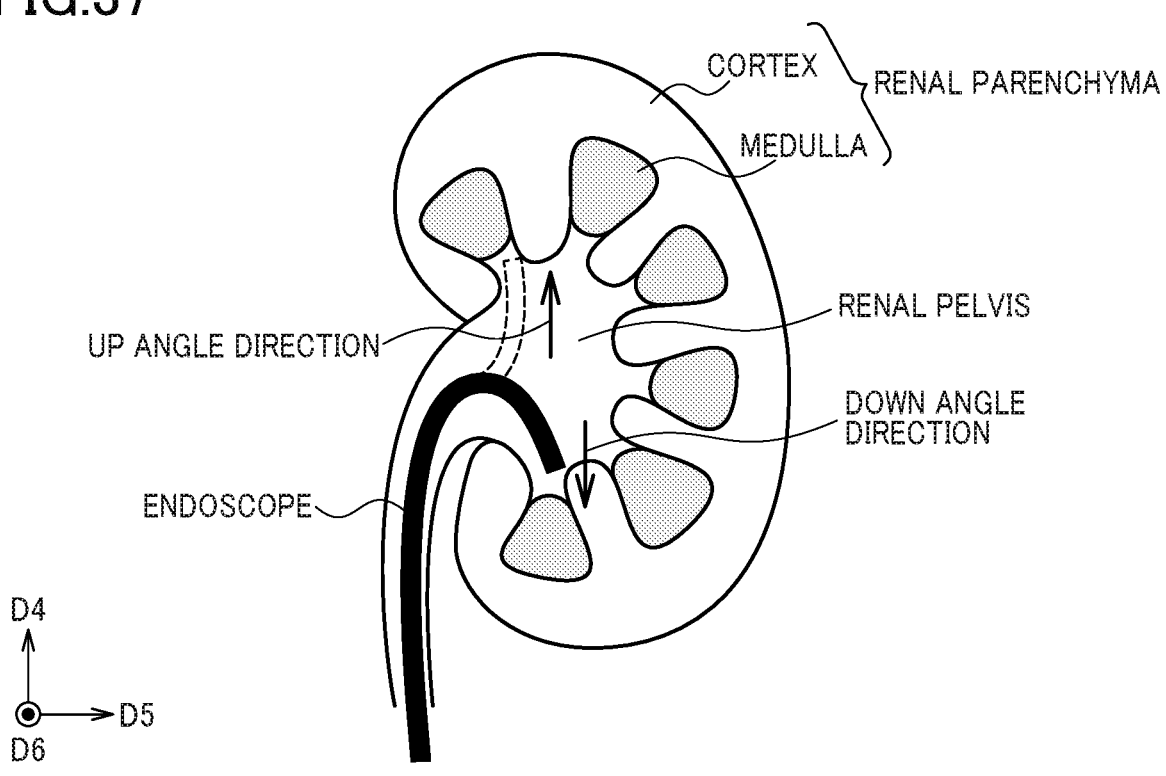
FIG. 37 is a cross-sectional view of the left kidney as an example of the kidney.

FIG. 37 is a cross-sectional view of the left kidney as an example of the kidney. Assume that the head direction is a direction D4, a direction that is orthogonal to the direction D4 and that is the left hand direction of the patient is a direction D5, and a direction orthogonal to the directions D4 and D5 and that is the front direction of the patient is a direction D6. In a case where the patient lies on his/her back on the operating table, the direction D6 is a vertical upward direction. An endoscope for the kidney can perform an angle operation upward and downward. In a state where the tip of the endoscope is inserted from the ureter to the renal pelvis, an up angle is an angle toward the direction D4, and a down angle is an angle toward the opposite direction of the direction D4.

Figure 38:
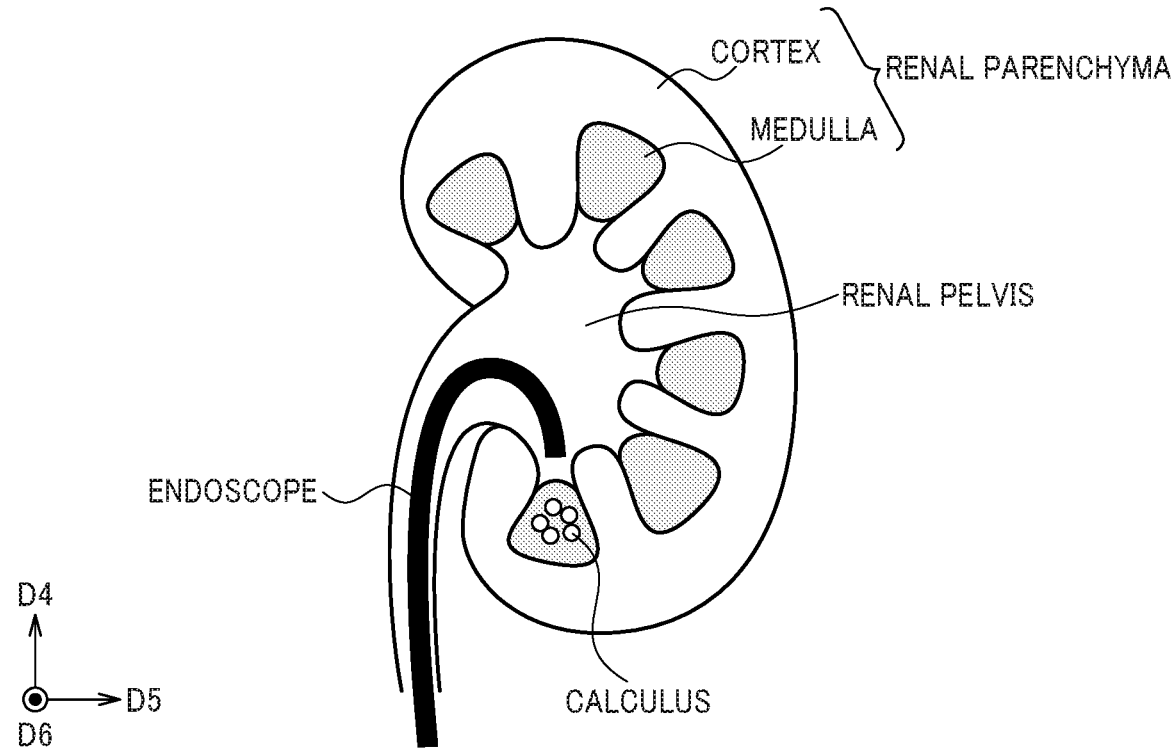
FIG. 38 is a diagram for describing an issue in manipulation of removing a kidney stone.
Figure 39:
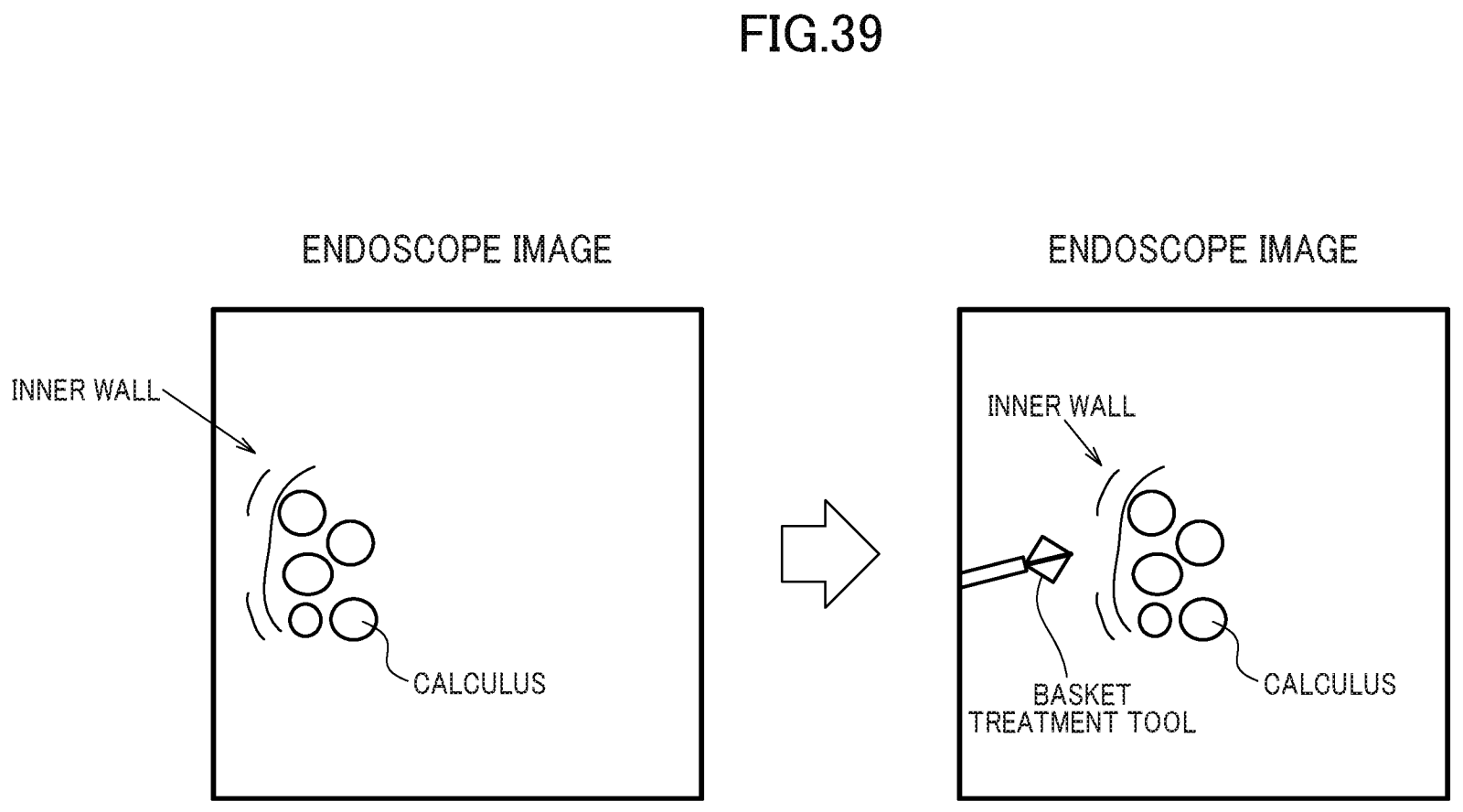

FIGS. 38 and 39 are diagrams for describing an issue in the manipulation of removal of the kidney stone. As illustrated in FIG. 38, calculi are accumulated on the foot down side of the patient, that is, on the opposite side of the direction D4. Since the patient takes a supine posture on the operating table in treatment, the calculi are accumulated in a vertical downward direction, that is, on the opposite side of the direction D6. As illustrated in FIG. 39, the calculi are in a state of being lopsidedly inclined toward to the inner wall of the kidney on the left side of a screen when viewed in the endoscopic image. Since the operator wants to perform the treatment while watching the calculi as a target of manipulation around the center of the screen, the basket treatment tool is projected while the tip of the endoscope is pressed against the inner wall of the kidney, whereby the calculi are arranged at the center of the endoscope image while the inner wall of the kidney is pressed toward the left side by the tip of the endoscope and the basket treatment tool.

However, there is an issue that pressing the tip of the endoscope against the inner wall of the kidney in the above-mentioned manipulation causes the tip of the endoscope to be embedded in the inner wall, causes an objective lens of the camera to be covered with the inner wall, and narrows or loses the visual field of the camera.

Figure 40:
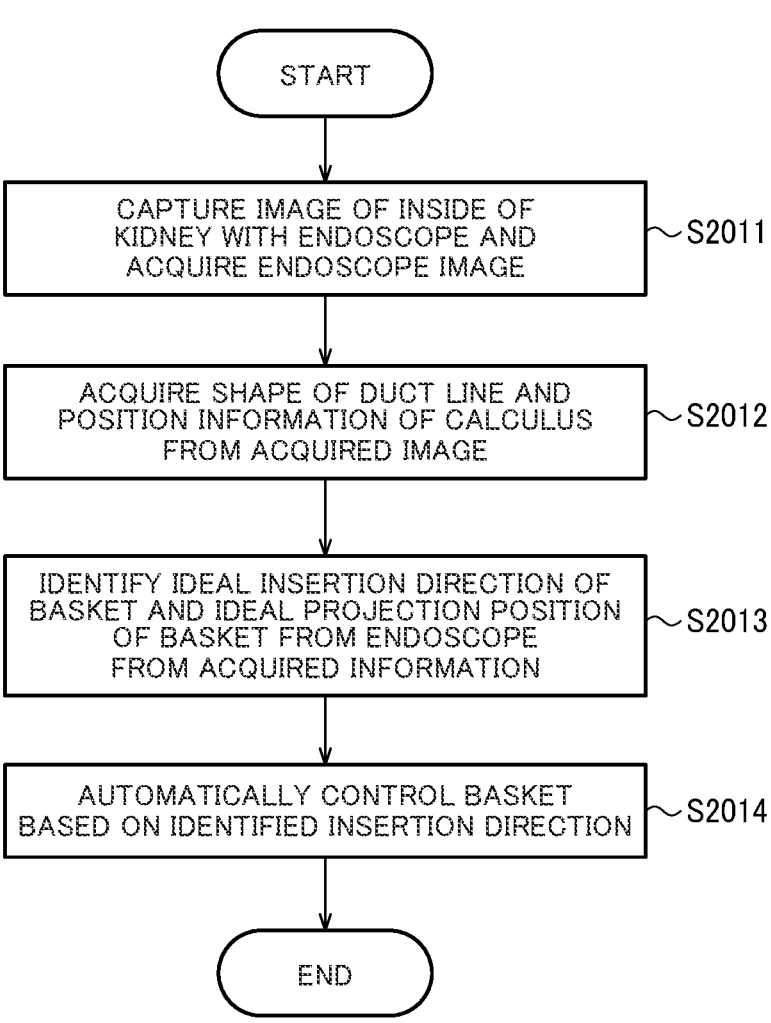
FIG. 40 illustrates the flow of processing of controlling a projection position of the basket treatment tool in removal of the kidney stone.

FIG. 40 illustrates the flow of processing of controlling a projection position of the basket treatment tool in removal of the kidney stone. A description of parts similar to those in FIG. 22 is omitted.

In step S2011, the endoscope captures an image of the inner cavity of the kidney, and the drive control device 2200 acquires image data of the endoscope image.

In step S2012, the drive control device 2200 acquires the shape of the duct line of the kidney and position information of the calculus from the endoscope image. The drive control device 2200 performs image recognition processing on the endoscope image to recognize the shape of the duct line of the kidney and the position information of the calculus. This image recognition may be implemented by image processing using machine learning.

In step S2012, the drive control device 2200 acquires information of the basket projectable range RA, which is the range of positions at which the basket treatment tool 3400 is projectable from the tip portion 2130 of the endoscope.

In step S2013, the drive control device 2200 determines a position at which the basket treatment tool 3400 is projected from the tip portion 2130 of the endoscope, based on the shape information of the duct line, the position information of the calculus, and the information of the basket projectable range RA, each of which is acquired in step S2012. In the example in FIG. 38, the projection position is determined on the opposite side of the direction D6 at the tip of the endoscope provided with the channel opening. This corresponds to determination of the projection position at which the basket treatment tool 3400 is projected from the left side of the screen in FIG. 39.

Figure 41:
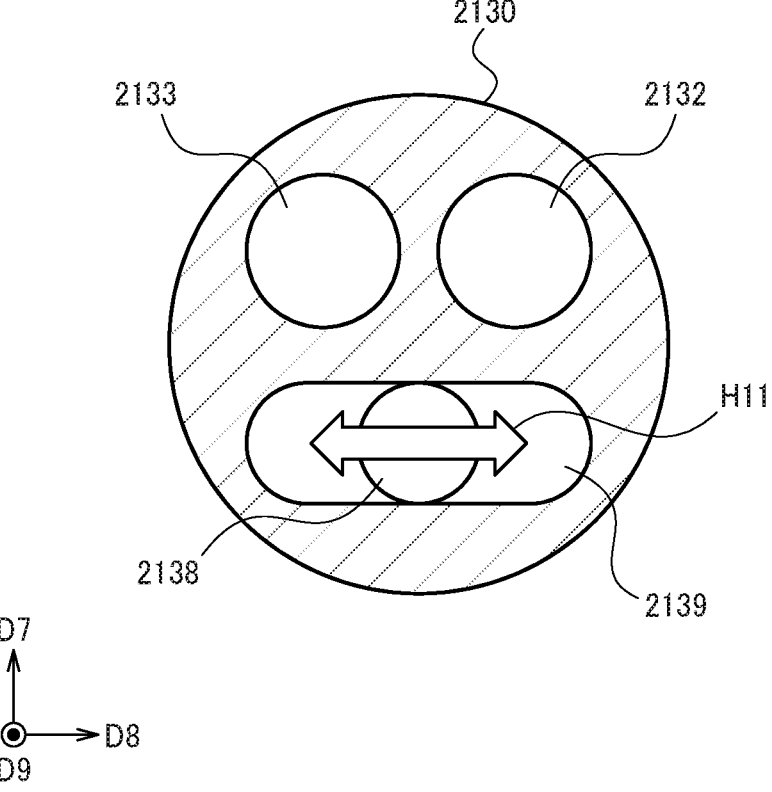
FIG. 41 illustrates a third example of automatic control.

In step S2014, the drive control device 2200 automatically controls the endoscope and the basket treatment tool 3400 based on the projection position determined in step S2013. FIG. 41 illustrates a third example of automatic control. FIG. 41 is a front view of an end surface of the tip portion 2130. The tip portion 2130 of the endoscope includes the camera 2132, the illumination lens 2133, a channel opening 2138, and an opening 2139. Assume that an up angle direction is a direction D7, an axis line direction is a direction D9, and a direction orthogonal to the directions D7 and D9 is a direction D8.

As indicated in H11, the opening 2139 is an opening that makes the channel opening 2138 slidable in the direction D8 or the opposite direction of the direction D8. Sliding of the channel opening 2138 is implemented by a slide mechanism that is similar to the slider rail 3131 and the slider base 3132 described with reference to FIGS. 33 and 34. In the example illustrated in FIGS. 38 and 39, the position of the channel opening 2138 is determined on the direction D8 side in the opening 2139. With this configuration, since the basket treatment tool 3400 that projects from the left side of the screen of the camera 2132 retains the inner wall of the kidney on the left side of the screen, it becomes hard for the inner wall to cover the objective lens of the camera 2132, and the visual field of the camera 2132 becomes easily secured.

Figure 42:
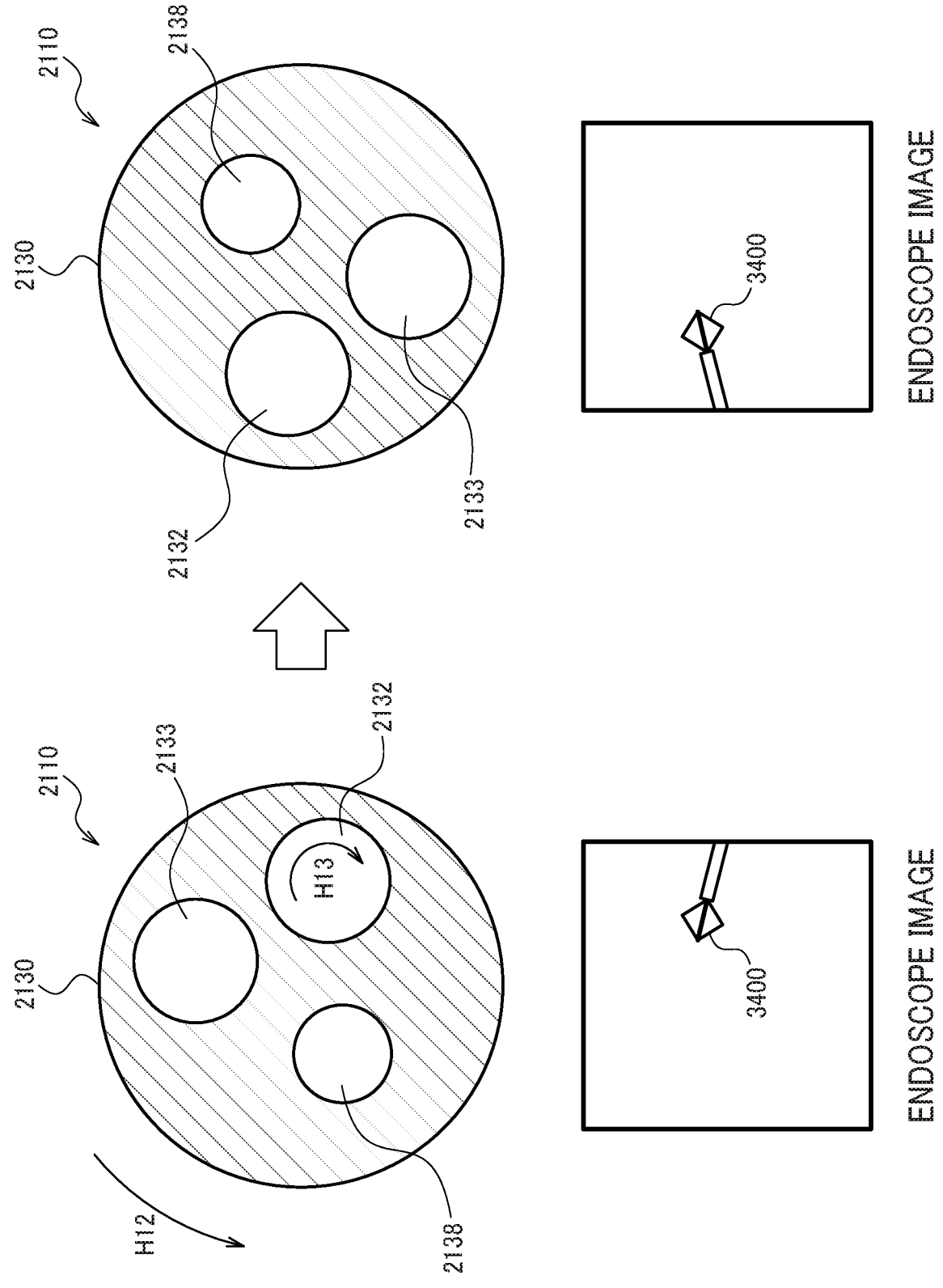
FIG. 42 illustrates a fourth example of automatic control.

FIG. 42 illustrates a fourth example of automatic control. The tip portion 2130 of the endoscope includes the camera 2132, the illumination lens 2133, and the channel opening 2138. As indicated in H12, the drive control device 2200 rolls the tip portion 2130 of the endoscope to move the position of the channel opening 2138. FIG. 42 illustrates rolling toward the tip in the counterclockwise direction, but may be in a clockwise direction. For example, with the arrangement of a motor that rotates the roll operating portion 2121 in the coupling element 2125, the motor rotates the roll operating portion 2121 to rotate the whole of the insertion portion 2110, and thereby rolls the tip portion 2130. The drive control device 2200 controls the motor through wired communication or wireless communication to roll the tip portion 2130. Alternatively, instead of the whole of the insertion portion 2110, only the tip portion 2130 may be configured to roll.

Rolling the tip portion 2130 of the endoscope also rotates the camera 2132, and thereby rotates the visual field. For example, in a case where the tip portion 2130 of the endoscope rolls toward the tip of the endoscope in the counterclockwise direction as illustrated in the left drawing of FIG. 42, the visual field of the camera 2132 rotates in the counterclockwise direction. Rotating the camera 2132 toward the tip of the endoscope in the clockwise direction as indicated in H13 prevents rotation of the visual field of the camera 2132. A rotation angle of the camera is identical to a rotation angle of the rolling in the opposite direction. A mechanism for rotating the camera 2132 can be configured with, for example, a wire, a motor that pushes/pulls the wire, a gear mechanism that converts pushing/pulling of the wire into rotation, and the like. The motor is arranged in, for example, the coupling element 2125 or the wire driving section 2250 of the drive control device 2200.

Note that instead of mechanical rotation of the camera 2132, an image may be rotated by image processing to keep the visual field constant. For example, in a case where the visual field of the camera 2132 is rotated in the counterclockwise direction by the rolling, the image is rotated by the image processing in the clockwise direction. A rotation angle in the image processing is identical to the rotation angle of the rolling.

In the present embodiment, the treatment tool 2400 is the basket treatment tool 3400 projectable from the side surface of the tip portion 2130 of the endoscope 2100. In the present embodiment, the body cavity is the inner cavity of the kidney. The object of the treatment is the calculus in the kidney.

In the present embodiment, the projection position of the basket treatment tool 3400 can be controlled to be a projection position at which the basket treatment tool 3400 can remove the calculus appropriately relative to the shape of the inner cavity of the kidney or the position of the calculus in the inner cavity of the kidney.

In the present embodiment, the tip portion 2130 of the endoscope 2100 has an opening portion, from which the treatment tool 2400 is projected. The control device 2600 controls a position of the opening portion in the tip portion 2130, and thereby controls the projection position of the treatment tool 2400.

In accordance with the present embodiment, the control device 2600 controls the position of the opening portion in the tip portion 2130 based on the identification information, which is at least one of the body cavity shape information indicating the shape of the body cavity or the position information indicating the object of treatment in the body cavity, and can thereby control the projection position of the treatment tool 2400 based on the identification information.

Note that in FIG. 41, the channel opening 2138 corresponds to the opening portion from which the treatment tool is projected. Movement of the channel opening 2138 in the opening 2139 changes the position of the opening portion in the tip portion 2130.

In the present embodiment, the tip portion 2130 of the endoscope 2100 has the opening from which the treatment tool 2400 is projected. The control device 2600 controls the rotation of the tip portion 2130, and thereby controls the projection position of the treatment tool 2400.

In accordance with the present embodiment, rotating the tip portion 2130 changes the position of the opening portion arranged in the tip portion 2130. With this configuration, the control device 2600 controls the rotation of the tip portion 2130 based on the identification information, and can thereby control the projection position of the treatment tool 2400 based on the identification information.

Note that in FIG. 42, the channel opening 2138 corresponds to the opening portion from which the treatment tool is projected. As indicated in H12, rolling of the tip portion 2130 changes the position of the channel opening 2138.

In accordance with the present embodiment, the endoscope 2100 includes an imaging device. The imaging device is arranged in the tip portion 2130 so as to be independent from the rotation of the tip portion 2130. The control device 2600 controls the rotation of the tip portion 2130 to prevent the rotation of the visual field of the imaging device.

In accordance with the present embodiment, the imaging device is independent from the rotation of the tip portion 2130, and thus can be configured not to rotate even when the tip portion 2130 rotates. This can prevent the rotation of the visual field of the imaging device while controlling the projection position of the treatment tool 2400 with the rotation of the tip portion 2130, and thereby allows the operator to execute manipulation with a constant visual field.

Note that in FIG. 42, the camera 2132 corresponds to the imaging device. While FIG. 42 illustrates the example in which the camera 2132 rotates in the opposite direction of that of the rolling of the tip portion 2130, the method of preventing the rotation of the visual field of the imaging device is not limited thereto. For example, the camera 2132 is arranged at a fixed position at the center of the tip portion 2130, and only the tip portion 2130 around the camera 2132 may be configured to roll. With this configuration, while the camera 2132 is fixed and remains not to rotate, the rolling of the tip portion 2130 can change the projection position of the treatment tool 2400.

Although the embodiments to which the present disclosure is applied and the modifications thereof have been described in detail above, the present disclosure is not limited to the embodiments and the modifications thereof, and various modifications and variations in components may be made in implementation without departing from the spirit and scope of the present disclosure. The plurality of elements disclosed in the embodiments and the modifications described above may be combined as appropriate to implement the present disclosure in various ways. For example, some of all the elements described in the embodiments and the modifications may be deleted. Furthermore, elements in different embodiments and modifications may be combined as appropriate. Thus, various modifications and applications can be made without departing from the spirit and scope of the present disclosure. Any term cited with a different term having a broader meaning or the same meaning at least once in the specification and the drawings can be replaced by the different term in any place in the specification and the drawings.

According to some aspects of the present embodiment, the following are provided.

1. A medical system comprising:
an endoscope with a tip from which a treatment tool is projectable; and
a controller configured to:

acquire a body cavity image data in which a body cavity including an object of treatment of the treatment tool is captured;
identify, from the body cavity image data, at least one of body cavity shape information indicating a shape of the body cavity or position information indicating a position of the object of the treatment in the body cavity as identification information; and
control a projection position of the treatment tool from the tip of the endoscope based on the identification information.

2. The medical system as defined in item 1, wherein the treatment tool is a basket treatment tool projectable from a side surface of the tip of the endoscope.

3. The medical system as defined in item 2, wherein
the tip of the endoscope is variable in position at which the basket treatment tool is projected from the side surface, and
the controller is configured to control the position at which the basket treatment tool is projected from the side surface.

4. The medical system as defined in item 1, wherein
the tip of the endoscope includes a raising base that controls a projection direction in which the treatment tool is projected from the tip, and
the controller is configured to control a position of the raising base in the tip, and thereby controls the projection position.

5. The medical system as defined in item 4, wherein the controller performs control to move the position of the raising base in the tip in a direction crossing the projection direction, and thereby controls the projection position.

6. The medical system as defined in item 1, wherein
the tip of the endoscope includes an opening from which the treatment tool is projected, and
the controller controls a position of the opening in the tip, and thereby controls the projection position.

7. The medical system as defined in item 1, wherein
the tip of the endoscope includes an opening from which the treatment tool is projected, and
the controller controls a rotation of the tip, and thereby controls the projection position.

8. The medical system as defined in item 7, wherein
the endoscope includes an imaging sensor arranged in the tip portion so as to be independent from the rotation of the tip, and
the controller controls the rotation of the tip to prevent rotation of a visual field of the imaging sensor.

9. The medical system as defined in item 1, wherein
the body cavity is a biliary duct, and
the object of the treatment is a gallstone in the biliary duct.

10. The medical system as defined in item 1, wherein
the body cavity is a lumen in a kidney, and
the object of the treatment is a calculus in the kidney.

11. A treatment tool control method of controlling a treatment tool projectable from a tip of an endoscope, the method comprising:
acquiring a body cavity image in which a body cavity including an object of treatment of the treatment tool is captured;
identifying, from the body cavity image, at least one of body cavity shape information indicating a shape of the body cavity or position information indicating a position of the object of the treatment in the body cavity as identification information; and controlling a projection position of the treatment tool from the tip portion of the endoscope based on the identification information.

12. A non-transitory information storage medium that stores a program that causes a computer to at least perform:

acquiring a body cavity image in which a body cavity including an object of treatment of a treatment tool is captured, the treatment tool being projectable from a tip portion of an endoscope;

identifying, from the body cavity image, at least one of body cavity shape information indicating a shape of the body cavity or position information indicating a position of the object of the treatment in the body cavity as identification information; and controlling a projection position of the treatment tool from the tip portion of the endoscope based on the identification information.

What is claimed is:

1. A medical system comprising:

a basket treatment tool configured to be inserted into a biliary duct from a papillary orifice and to be driven to open/close and advance/retreat; and a processor comprising hardware, the processor being configured to:

determine, when the basket treatment tool is coupled with a gallstone and retreated, a retraction resistance corresponding to an amount of force used to retreat the basket treatment tool;

determine, based on the retraction resistance, whether the basket treatment tool is able to remove the gallstone via the papillary orifice; and responsive to determining that the basket treatment tool is able to remove the gallstone via the papillary orifice, control the basket treatment tool to retreat to remove the gallstone via the papillary orifice.

2. The medical system of claim 1, wherein the processor is configured to control crushing the gallstone responsive to determining that the basket treatment tool is unable to remove the gallstone via the papillary orifice.

3. The medical system of claim 2, wherein the processor is configured to control the crushing of the gallstone using the basket treatment tool.

4. The medical system of claim 2, wherein the processor is configured to determine whether the basket treatment tool is able to remove the gallstone via the papillary orifice responsive to controlling the crushing of the gallstone.

5. The medical system of claim 2, wherein the processor is configured to determine that the basket treatment tool is unable to remove the gallstone via the papillary orifice based on the retraction resistance being equal to or greater than a predetermined value.

6. The medical system of claim 1, wherein the processor is configured to determine that the basket treatment tool is able to remove the gallstone via the papillary orifice based on the retraction resistance being less than a predetermined value.

7. The medical system of claim 1, wherein the processor is configured to control an insertion of the basket treatment tool into the biliary duct effective to catch the gallstone prior to determining whether the basket treatment tool is able to remove the gallstone via the papillary orifice.

8. The medical system of claim 1, wherein the processor is configured to drive the basket treatment tool via electric driving.

9. The medical system of claim 1, wherein:

the processor is configured to determine, based on a transmissive image including the biliary duct, a size of the gallstone; and the determination of whether the basket treatment tool is able to remove the gallstone via the papillary orifice is responsive to a determination that the size of the gallstone is smaller than or equal to a predetermined size.

10. The medical system of claim 9, wherein the transmissive image is an endoscopic retrograde cholangiopancreatography (ERCP) image or a magnetic resonance cholangiopancreatography (MRCP) image.

11. The medical system of claim 1, further comprising a motor configured to drive the opening/closing and advancing/retreating of the basket treatment tool, wherein the processor is configured to control the motor so that the basket treatment tool crushes the gallstone or the basket treatment tool is inserted.

12. The medical system of claim 1, wherein the retraction resistance is based on one or more of: information from a strain gauge within the basket treatment tool or a motor or motor controller used to retreat the basket treatment tool.

13. A control apparatus comprising:

a processor comprising hardware, wherein the processor is configured to:

determine, when a basket treatment tool is inserted into a biliary duct via a papillary orifice, coupled with a gallstone, and retreated, a retraction resistance corresponding to an amount of force used to retreat the basket treatment tool;

determine, based on the retraction resistance, whether the basket treatment tool is able to remove the gallstone via the papillary orifice; and responsive to determining that the basket treatment tool is able to remove the gallstone via the papillary orifice, control the basket treatment tool to remove the gallstone via the papillary orifice.

14. The control apparatus of claim 13, wherein the processor is configured to control crushing the gallstone responsive to determining that the basket treatment tool is unable to remove the gallstone via the papillary orifice.

15. The control apparatus of claim 14, wherein the processor is configured to control the crushing of the gallstone using the basket treatment tool.

16. The control apparatus of claim 14, wherein the processor is configured to determine whether the basket treatment tool is able to remove the gallstone via the papillary orifice after controlling the crushing of the gallstone using the basket treatment tool.

17. The control apparatus of claim 13, wherein the processor is configured to:

determine, based on a transmissive image including the biliary duct, whether a size of the gallstone is smaller than or equal to a predetermined size; and determine that the basket treatment tool is able to remove the gallstone via the papillary orifice responsive to a determination that the size of the gallstone is smaller than or equal to the predetermined size.

18. The control apparatus of claim 14, wherein the processor is configured to determine that the basket treatment tool is unable to remove the gallstone via the papillary orifice based on the retraction resistance being equal to or greater than a predetermined value.

* * * * *